US012638438B2

(12) United States Patent
Gibbs et al.

(10) Patent No.: US 12,638,438 B2
(45) Date of Patent: May 26, 2026

(54) SCREENING METHODS USING CANINE T2R RECEPTORS AND PET FOOD PRODUCTS AND COMPOSITIONS IDENTIFIED USING THE SAME

(71) Applicant: MARS, INCORPORATED, McLean, VA (US)

(72) Inventors: Matthew Ronald Gibbs, Leicestershire (GB); Neil George Desforges, Leicestershire (GB); Andrew John Taylor, Leicestershire (GB); Scott Joseph McGrane, Leicestershire (GB); Boris Klebansky, Demarest, NJ (US); Richard Masten Fine, Ridgewood, NJ (US)

(73) Assignee: MARS, INCORPORATED, McLean, VA (US)

( * ) Notice: Subject to any disclaimer, the term of this patent is extended or adjusted under 35 U.S.C. 154(b) by 434 days.

(21) Appl. No.: 17/569,251

(22) Filed: Jan. 5, 2022

(65) Prior Publication Data

US 2022/0120734 A1 Apr. 21, 2022

Related U.S. Application Data

(63) Continuation of application No. 16/885,102, filed on May 27, 2020, now abandoned, which is a continuation of application No. 15/746,658, filed as application No. PCT/US2016/044540 on Jul. 28, 2016, now abandoned.

(60) Provisional application No. 62/197,983, filed on Jul. 28, 2015.

(51) Int. Cl.

| | |
|---|---|
| ***G01N 33/50*** | (2006.01) |
| ***A23K 20/147*** | (2016.01) |
| ***A23K 50/40*** | (2016.01) |
| ***A23L 27/00*** | (2016.01) |
| ***C07K 14/72*** | (2006.01) |
| ***G01N 33/566*** | (2006.01) |

(52) U.S. Cl.

CPC ....... *G01N 33/5008* (2013.01); *A23K 20/147* (2016.05); *A23K 50/40* (2016.05); *A23L 27/84* (2016.08); *C07K 14/723* (2013.01); *G01N 33/502* (2013.01); *G01N 33/566* (2013.01); *G01N 2333/726* (2013.01)

(58) Field of Classification Search

CPC ............. G01N 33/5008; G01N 33/502; G01N 33/566; G01N 2333/726; A23K 20/147; A23K 50/40; A23L 27/84; C07K 14/723

See application file for complete search history.

(56) References Cited

U.S. PATENT DOCUMENTS

| | | | |
|---|---|---|---|
| 8,597,896 | B2 | 12/2013 | Brune et al. |
| 9,347,934 | B2 | 5/2016 | Shekdar et al. |
| 2014/0273001 | A1 | 9/2014 | Sandau et al. |
| 2016/0069860 | A1 | 3/2016 | Radhakrishna et al. |
| 2018/0372721 | A1 | 12/2018 | Gibbs et al. |

FOREIGN PATENT DOCUMENTS

| | | | |
|---|---|---|---|
| WO | WO 01/77676 | A1 | 10/2001 |
| WO | WO 2008/119195 | A1 | 10/2008 |
| WO | WO 2013/059836 | A1 | 4/2013 |
| WO | WO 2013/072332 | A1 | 5/2013 |
| WO | WO 2014/176336 | A1 | 10/2014 |

OTHER PUBLICATIONS

U.S. Appl. No. 15/746,658, filed Jan. 22, 2018.
U.S. Appl. No. 16/885,102, filed May 27, 2020, U.S. 2020/0292527, Sep. 17, 2020.
U.S. Appl. No. 15/746,658, filed Oct. 22, 2018 Restriction Requirement.
U.S. Appl. No. 15/746,658, filed Dec. 14, 2018 Response to Restriction Requirement.
U.S. Appl. No. 15/746,658, filed Mar. 25, 2019 Non-Final Rejection.
U.S. Appl. No. 15/746,658, filed Jun. 21, 2019 Response to Non-Final Rejection.
U.S. Appl. No. 15/746,658, filed Aug. 28, 2019 Final Rejection.
U.S. Appl. No. 15/746,658, filed Nov. 15, 2019 Response to Final Rejection with a Request for Continued Examination.
U.S. Appl. No. 15/746,658, filed Mar. 27, 2020 Final Rejection.
U.S. Appl. No. 15/746,658, filed May 4, 2020 Response to Final Rejection.
U.S. Appl. No. 15/746,658, filed May 12, 2020 Advisory Action.
U.S. Appl. No. 15/746,658, filed Oct. 23, 2020 Notice of Abandonment.
U.S. Appl. No. 16/885,102, filed Oct. 7, 2021 Non-Final Office Action.
U.S. Appl. No. 16/885,102, filed Jun. 21, 2021 Request for Continued Examination (RCE).
U.S. Appl. No. 16/885,102, filed Jun. 15, 2021 Advisory Action.
U.S. Appl. No. 16/885,102, filed May 18, 2021 Response after Final Action.
U.S. Appl. No. 16/885,102, filed May 18, 2021 Amendment and Request for Continued Examinaton (RCE).

(Continued)

*Primary Examiner* — Olga N Chernyshev
(74) *Attorney, Agent, or Firm* — Baker Botts L.L.P.

(57) ABSTRACT

The presently disclosed subject matter relates to methods of screening raw materials and pet food products to manufacture a palatable pet food product. The presently disclosed subject matter also relates to methods for identifying compounds that modulate the activity and/or expression of a bitter taste receptor.

11 Claims, 44 Drawing Sheets

Specification includes a Sequence Listing.

(56) References Cited

OTHER PUBLICATIONS

U.S. Appl. No. 16/885,102, filed Mar. 29, 2021 Final Office Acton.

U.S. Appl. No. 16/885,102, filed Jan. 13, 2021 Response to Non-Final Office Action.

U.S. Appl. No. 16/885,102, filed Oct. 15, 2020 Non-Final Office Action.

Brockhoff et al., "Structural requirements of bitter taste receptor activation," Proceedings of the National Academy of Sciences 107(24):11110-11115 (2010).

Dipizio et al., "Promiscuity and selectivity of bitter molecules and their receptors," Bioorganic & Medicinal Chemistry 23(14):4082-4091 (2015).

International Search Report mailed Oct. 21, 2016 in International Application No. PCT/US2016/044540.

Stables et al., "A Bioluminescent Assay for Agonist Activity at Potentially Any G-Protein-Coupled Receptor," Analytical Biochemistry 252:115-126, Article No. AB972308 (1997).

Canine Bitter Receptor Nucleotide Sequences and Corresponding Amino Acid Sequences cT2R1 nucleotide sequence (SEQ ID NO:1)

atgttagagttttaccttattatccattttcttttcacagtgatgcaatttctcatcggggttttagc
aaatggcatcattgtggtggtgaatggcactgagttgatcaagcagagaaagatgattcccttggctc
tccttctttgctgtctggcgatttccaggatttgtctacaattgatcatcttcttcatgaatctgggt
actctcttcttgattgaagtcccccctacttgctgataattttgtaattttcgtgtttgtaaatgaatt
gggactttggttcgccacatggcttggggtttactactgtgccaagatcgcccccataactcactcat
tctttttctggttgaagataaggatatccaagtggatgccatggctgatcctcgggtccatgatgtat
gcatccgtcccttctgttttctgcagcaaacagatatgggtttattcccaaaacgttttgtccagcct
tttttccccaaacgcaactcaaatcaaagaaacatctgctttacagattgcctttcttattaggttat
tattgccactgcttatctttctcggttccaccctacttttgatattttccctggggagacacacctgg
cagatgagaaacacagcaacaggccccagggaccctagcacaggtgtccacgtgagcacgatcctgtc
cgttctatccttcctggtcctctgcctctcccactacatggcagctgctttgctctcttttcagatct
ttcagctcagaagcctcgtctttctgatctgtctctgggtgtttgggtcctatccttctggacactct
atgatcttaattttaggaaatcctaaattgaaacaaaatgcaaagaagctcctcctccacgggaagtg
ctgccagtga cT2R1 amino acid sequence (SEQ ID NO:17)

MLEFYLIIHFLFTVMQFLIGVLANGIIVVVNGTELIKQRKMIPLALLLCCLAISRICLQLIIFFMNLG
TLFLIEVPLLADNFVIFVFVNELGLWFATWLGVYYCAKIAPITHSFFFWLKIRISKWMPWLILGSMMY
ASVPSVFCSKQIWVYSQNVLSSLFSPNATQIKETSALQIAFLIRLLLPLLIFLGSTLLLIFSLGRHTW
QMRNTATGPRDPSTGVHVSTILSVLSFLVLCLSHYMAAALLSFQIFQLRSLVFLICLWVFGSYPSGHS
MILILGNPKLKQNAKKLLLHGKCCQ*

FIG. 1A cT2R2 nucleotide sequence (SEQ ID NO:2)

atgatctccttttgtcagctcttcctcatgttattgttatgtcagcagaatttatcacagggattac
agtaaatggatttcttatcatcatgaactgtaaagaattgatcaaaagcagaaagccaacaccagtgc
aactccttttcatatgtatagggatgtcgagatttggtctgctcatggtgttaatgatacaaagtttt
ttctctgtgttatttccactcttttataaggtaaacattttggtacagcaatgttgttcttttggat
gtttttagctctgtcagtttctggtttgccacctgcctttctgtattttactgcctcaagatagcag
gcttcactcaatcctgttttctttggctgaaattcaggatctcgaagttaatgccttggctacttctg
ggaagtttgctggcctccatgagcattgcagctctgtgtattgaagcagattaccctaaaaaggtgga
tgatgatgccctcaagaatgccacattgaagaggactgaacccaagataaggcaaattagtgaaatgc
tgcttgtcaacttggcattactatttcctctagccatatttgtgatgtgcacttttatgttattcatt
tctctctataagcacactcatcggatgcaaaatggatctcatggtgttagaaatgccagcacaaaagc
ccatataaatgcattaaaaacagtgataacattcttttgcttctttatttcttattttgctgccttca
tggcaaatatgacattcagtattccttatggaagtcattgcttctttgtagtaaaggacataatggca
gcatttccctctggtcattcaattataatcctcctgagtaattctaaataccaacaacctttcaggag
acttctctgcttcaaaaagaatcaatga cT2R2 amino acid sequence (SEQ ID NO:18)

MISFLSALPHVIVMSAEFITGITVNGFLIIMNCKELIKSRKPTPVQLLFICIGMSRFGLLMVLMIQSF
FSVLFPLFYKVNIFGTAMLFFWMFFSSVSFWFATCLSVFYCLKIAGFTQSCFLWLKFRISKLMPWLLL
GSLLASMSIAALCIEADYPKKVDDDALKNATLKRTEPKIRQISEMLLVNLALLFPLAIFVMCTFMLFI
SLYKHTHRMQNGSHGVRNASTKAHINALKTVITFFCFFISYFAAFMANMTFSIPYGSHCFFVVKDIMA
AFPSGHSIIILLSNSKYQQPFRRLLCFKKNQ*

FIG. 1B

<u>cT2R3 nucleotide sequence</u> (SEQ ID NO:3)

atgtcagggctggggaaatccgtgttcctggttctgtctgtcactcagttcattctggggatgctggg
gaatggtttcatagtgttggtcaatggcagcagctggttcaagaacaagacagtctctttgtctgacg
ttatcatcactaacctggctctctccaggattgttctgctgtggattctcttggttgatggtgtttta
atggtcttcttttccaaagtacatgatgaagggacagtaatggaaattattgatattttctggacatt
tacgaaccacctgagcatttggcttgccacctgtctcagtgtcctctactgcctgaaattgccagtt
tctcccatccgacgttcctctggctcaagtggagagtttccagagtggtcgtacagatgattttgggt
gcactgctcttatcgtgtgccagtgccatgtctctggtccatgaatttaagatctattctattctcag
tggaattgctggtacagggaatgtgaccgagcactttagaaagaagagaaatgactataaagtggccc
atgttcttgggactctgtggaacctccctcccctaattgtttctctggcctcctactttctgctcatc
ttctccctgggaaggcacacacagcagatgaagcacagtggcaccagctccagagatctgagcacgga
ggcccaccagagagccatcaaaatcatcgtctctttcctctttctcttcctgctttactttcttgcct
ttttaattacatcatccagttatttcataccagaaactgagatggttaagagagttggagtagttgtt
acaatgttttaccctgccagccactcattcgttatcattctgggaaacaataagctgaagcagatgtt
tacggagatgctgtgctgtgagcctggttatctgaagcctggattcaaaagaccttttgccccataa

<u>cT2R3 amino acid sequence</u> (SEQ ID NO:19)

MSGLGKSVFLVLSVTQFILGMLGNGFIVLVNGSSWFKNKTVSLSDVIITNLALSRIVLLWILLVDGVL
MVFFSKVHDEGTVMEIIDIFWTFTNHLSIWLATCLSVLYCLKIASFSHPTFLWLKWRVSRVVVQMILG
ALLLSCASAMSLVHEFKIYSILSGIAGTGNVTEHFRKKRNDYKVAHVLGTLWNLPPLIVSLASYFLLI
FSLGRHTQQMKHSGTSSRDLSTEAHQRAIKIIVSFLFLFLLYFLAFLITSSSYFIPETEMVKRVGVVV
TMFYPASHSFVIILGNNKLKQMFTEMLCCEPGYLKPGFKRPFAP*

FIG. 1C

<u>cT2R4 nucleotide sequence</u> (SEQ ID NO:4)

atgcttcagatattctttttatctgccattattttctcagcaattttgaattttgtgggactcattgt
aaatctgtttattgcagtggtcagttataggacttggctcaaaagccatagaatttcctcttctaatt
ggatcctcttcagcttgggcatcaccagatttcttatgctgggactgtttctactcaacatcatctac
ttcttcatctctccaaaaatggaaaggtcggtgcacctatcccacttttttcctgtcgtgttggatgtt
tttggactctaatagtctctggtttgtaaccttgctcaatgccttgtactgcgtgaagattacggact
tccaacttggagtatttctcctgctgaagcgaaatctctccccaaagatccccaggctgttgctagcc
tgtgtactgatttctgccttcaccactctcctgtatgttgtgctcaaacagacatcatcccttcctga
atttgtgactcagagaaatggtacaggatgtggcatccatgggagtgtcttgtctttggtgacctctt
tggtcttgcgctcagttctccagtttatcattaatgtgacttctgcttccttgttgatacattccttg
aggagacatatacagaagatgcagaaaaacaccactatttttttggaatcctcagactgaagctcatgt
gggcgctatgaagctgatgatctgtttcctcatcctgtacattccttactcagttgctaccttgctac
attatttcccttatggtgggatggatttgagaaccagatccatctgtttggttatttccagcttttac
cctccaggacattctattctcattatcctcacacatcctaaactgaaaacaaaagcaaagaagattct
ttgtttcaacaaatag

<u>cT2R4 amino acid sequence</u> (SEQ ID NO:20)

MLQIFFLSAIIFSAILNFVGLIVNLFIAVVSYRTWLKSHRISSSNWILFSLGITRFLMLGLFLLNIIY
FFISPKMERSVHLSHFFLSCWMFLDSNSLWFVTLLNALYCVKITDFQLGVFLLLKRNLSPKIPRLLLA
CVLISAFTTLLYVVLKQTSSLPEFVTQRNGTGCGIHGSVLSLVTSLVLRSVLQFIINVTSASLLIHSL
RRHIQKMQKNTTIFWNPQTEAHVGAMKLMICFLILYIPYSVATLLHYFPYGGMDLRTRSICLVISSFY
PPGHSILIILTHPKLKTKAKKILCFNK*

FIG. 1D

<u>cT2R5 nucleotide sequence</u> (SEQ ID NO:5)

atgctgactgctgccctaccactgctgatggtggtggcagtggttgaatttctcattggctt
ggtgggaaatggagtccttatggtctggagttttggtgaatgggtcagaaaattcaacgggt
cctcatacaacctcattgtcctgggcctggctgtctgccgatttctcctgcagtgtctgatt
atgatggacttaagcctgtttccatttttccagagtagccgttggcttcactatctcagtat
cttctggatcctggtaagccaggccagcctgtggtttgccactttcctcagcgtcttctact
gcaggaagatcatgacccttgaacatcctgtctgcttgtggctgaagcagagggcctattgc
ctgagtctctggtgccttctggtgtacctcatgatcagtttgttacttgtagcacacattgg
cttaaagccctataatccttctcaaggcaacagcagcattctgtacccccttaaaagctggc
actacctgtatatagtaaagctcaacgcaggaagtggattgcctctcatggtgtttcttgtt
tcttctgggatgctgattgtctctttgtatagacaccacaagaagatggaggtacatacagc
tggtaggagagatgctcaggccaaggctcacatcactgtactgaagtccttgggctgcttcc
ttatccttcatgtgatttatatcctggccagcccttttccattacctccaagtcttctgct
gatctcctcgttgtcttcatctctgagacagtcatggctgcctatccttctcttcattctgt
cattctgatcctggggaatcccaggatgaagcagacttgtcagagaattctgtggaagacag
tgtgtgcttggaaatcctag

<u>cT2R5 amino acid sequence</u> (SEQ ID NO:21)

MLTAALPLLMVVAVVEFLIGLVGNGVLMVWSFGEWVRKFNGSSYNLIVLGLAVCRFLLQCLI
MMDLSLFPFFQSSRWLHYLSIFWILVSQASLWFATFLSVFYCRKIMTLEHPVCLWLKQRAYC
LSLWCLLVYLMISLLLVAHIGLKPYNPSQGNSSILYPLKSWHYLYIVKLNAGSGLPLMVFLV
SSGMLIVSLYRHHKKMEVHTAGRRDAQAKAHITVLKSLGCFLILHVIYILASPFSITSKSSA
DLLVVFISETVMAAYPSLHSVILILGNPRMKQTCQRILWKTVCAWKS*

FIG. 1E cT2R7 nucleotide sequence (SEQ ID NO:6)

atgccggataaagtggagagcatcttaatgctcgtagcagctggagaattttcaatggggattttagg
gaatacattcattggattggtaaactgcataggctggatcaagaagaggaagattgcctccattgatt
taatcctcacaagtctggccatatccagaatttgtctattatgtataatactattagattgttttata
ttggtgctgtatccagatgtctatgctaccggtaaacaaatgagaataattgacttcttctggacact
aaccaaccatttaagtgtctggtttgccacctgtctcagcattttctatttcctcaagattgcgaatt
tcttccatcccctttttcctctggatgaagtggagaattgacagtgcgattcctaggatcctgctggga
tgcttggccctttctgtgtttattagccttgttgtcactgagaatttgaatgatgatttcagatgttg
tgttaggacaaagaagaaaacaaacttaactgtgagatgcagagtaaagaaagctaaatattcttcca
tcaagatttgcctcaacctgttaacgctattcccctttttctgtgtccctgatctcatttctcctcttg
atcctctccctctggagacataccaggcagatgaagttcaatgccacagggtgtagagacttcagcat
agaagcccacatgggagccatgaaagctgtcatctcctttctcctcctttttcatcgcctactatttgg
cctttcttgtagccacctctagctactttatgccagagactgaattagctgtgatcattggtgagttg
atagctctaatctatccctcgagccattcgtttatcctaattctggggagcaataaattaagacaggc
atctctaagggtactatggaaagtaaaatatgtcttaaaaagaagaaacttctaa cT2R7 amino acid sequence (SEQ ID NO:22)

MPDKVESILMLVAAGEFSMGILGNTFIGLVNCIGWIKKRKIASIDLILTSLAISRICLLCIILLDCFI
LVLYPDVYATGKQMRIIDFFWTLTNHLSVWFATCLSIFYFLKIANFFHPLFLWMKWRIDSAIPRILLG
CLALSVFISLVVTENLNDDFRCCVRTKKKTNLTVRCRVKKAKYSSIKICLNLLTLFPFSVSLISFLLL
ILSLWRHTRQMKFNATGCRDFSIEAHMGAMKAVISFLLLFIAYYLAFLVATSSYFMPETELAVIIGEL
IALIYPSSHSFILILGSNKLRQASLRVLWKVKYVLKRRNF*

FIG. 1F cT2R10 nucleotide sequence (SEQ ID NO:7)

atgctaagcatactggaaggcctcctcattttttatagctgttagtgaatcaatactgggagttttagg
gaatggatttattggacttgtcaattgtattgactgtgtgaagaacaaaaagttttctatggttggct
ttattctcactggcttagctacttccagaatttgtctgatattgataataattacagatggatttata
aagatattctctccagatatgtattcctctggtaacttaattgattatattagttacctatgggtaat
tatcaatcaatcaagtatctggtttgccaccagcctcagcatcttctatttcctgaagatagcaaatt
tttcccaccacatttttctctggctgaagggtagaatcaatagcgttcttccccttctgatgggatcc
ttgtttatttcatggttatttacttttccacaaattgtgaagattattaatgataatagaatgaagag
tagaaatacaacctggcagctcaacatgcagaaaagtgaattctttactaagcagatttactcaacc
taggagtcattcttctctttactctatgcctgattacatgtttcttgctaatcgtttccctttggaga
cacaacaggcacatgcaattgaatgtcactggactccgagaccccagtacagaagcacatgtgaaagc
aatgaaaattttggtatcttttatcatcctctttatcttgtattttataggcattgccatagaaatat
catgtttcattctgccagaaaacaaactgctgtttattttggtatgatgaccacagccatctatccc
tggggtcattcatttatcctaattctaggaaacagcaagctaaagcaagcttctttgaagaccctgca
gcaactcaagtgcgaggcaaggagactgctcacagctgcacagatccatgtgggggaaatggatgtt
ccaggagaataatctag cT2R10 amino acid sequence (SEQ ID NO:23)

MLSILEGLLIFIAVSESILGVLGNGFIGLVNCIDCVKNKKFSMVGFILTGLATSRICLILIIITDGFI
KIFSPDMYSSGNLIDYISYLWVIINQSSIWFATSLSIFYFLKIANFSHHIFLWLKGRINSVLPLLMGS
LFISWLFTFPQIVKIINDNRMKSRNTTWQLNMQKSEFFTKQILLNLGVILLFTLCLITCFLLIVSLWR
HNRHMQLNVTGLRDPSTEAHVKAMKILVSFIILFILYFIGIAIEISCFILPENKLLFIFGMMTTAIYP
WGHSFILILGNSKLKQASLKTLQQLKCEARRLLTAAQIHVGGNGCSRRII*

FIG. 1G

<u>cT2R12 nucleotide sequence</u> (SEQ ID NO:8)

atggcaggcacaatgaagaatgtatttatgatgatttttgccggagaattcataatagggattttggg
aaatggattcattatattggttaactgtatcgattggatcaggagctggaagttcttcctgattgact
ttattcttacctgcttagccatttccaggatatttctgctgtgcataataatgttaggcataggtcta
gatataatttgtaaggaaatatggtacaatgataatcaactgataacctttgaagtcctctggacagg
atgcaattatttctgcacaatctgtactgtgtgcctcagtgtcttctacttcctcaagatagccaact
cttccaatcccatttcttctggctaaaacggagaattcacagactgcttctcattattgtcctggga
gcagtcttctatttctgcttgtccctgcttttgaaggatatagtatttaagaacatgatcaaaaccaa
ggtaaacactgaaagcaatgtgacattaaatttcacagcgagaaaatatgatttactaacttctaata
tattcctgaacatgctattcgtcatcccctttgcagtgtctctggcttcctttgtccttttgatccat
tccttatggaaccataccaggcggatgaagggcattgattctggggatcttatcacagaggcccatgt
aagagccatgaagtttatgatttcattcctgctattcttctttatatactatttgagcaatattataa
tatattttgcctatgttgttctggatagtctggtggcaaaaatttttgctaatatattagtattttcc
tatccttctggccatccatttcttctgattttatggaactgcaaattgaaacaggcttctctctatgt
cctgaggaagctgaagtggtgcatgaatctaaggaaacccgcatacataaagcatacctga

<u>cT2R12 amino acid sequence</u> (SEQ ID NO:24)

MAGTMKNVFMMIFAGEFIIGILGNGFIILVNCIDWIRSWKFFLIDFILTCLAISRIFLLCIIMLGIGL
DIICKEIWYNDNQLITFEVLWTGCNYFCTICTVCLSVFYFLKIANSSNPIFFWLKRRIHRLLLIIVLG
AVFYFCLSLLLKDIVFKNMIKTKVNTESNVTLNFTARKYDLLTSNIFLNMLFVIPFAVSLASFVLLIH
SLWNHTRRMKGIDSGDLITEAHVRAMKFMISFLLFFFIYYLSNIIIYFAYVVLDSLVAKIFANILVFS
YPSGHPFLLILWNCKLKQASLYVLRKLKWCMNLRKPAYIKHT*

FIG. 1H

<u>cT2R38 nucleotide sequence</u> (SEQ ID NO:9)

atgttggctctgactcctgttataactgtgtcctatgaagtcaagagtgcatttatgttcctttcagt
actggagctcgcagtggggatcctgaccaatgccttcattttcttggtgaattttgggatgtggtga
ggaggcagccactgagcaactgcgatcttatccttctgagtctcagcctcactcgacttttcctgcat
gggctgctgtttctggatgccatccagcttacatacttccagcggatgaaagacccactgagcctcag
ctaccagaccatcatcatgctctggatgatcacaaaccaagctgggctctggctcaccacctgtctca
gtcttttctactgctccaagattgtccgtttctctcatacctccttctctgcttggcaaactgggtc
tccaggaaggcaccccagatgctcctgggtgccatgcttttctcttctgcctgcactctcctctgttt
ggggacttctttagtagatctggctttgcattcacaactgtgctactcatgaataatacagaattta
attcacaaattgtaaaactcaatttctattattcctccatcttctgtaccctggggtcaatccctcct
ttcatgtttttctggtttcttctggggtgctgattatctctctgggaaggcacatgagaacaatgaa
ggccaacaccaaagactccggtgaccccagcctggaggcccatatcaaagcactcatatctctcatct
cctttctctgcctctatgtggtgtcattctgtgttgcccttatctcagtgcctttaaccatggtgtgg
cacaacaagatcggggtaatgatctgtgtagggatcctagcagcttgtccctctatacatgcagccat
cctgatctcaggcaatgccaagctgaggagagctgtggagaccattctactctgggttcagagcagcc
ttaaggtaagggcaggccacagggcagatctcaggactccagatctatgttga

<u>cT2R38 amino acid sequence</u> (SEQ ID NO:25)

MLALTPVITVSYEVKSAFMFLSVLELAVGILTNAFIFLVNFWDVVRRQPLSNCDLILLSLSLTRLFLH
GLLFLDAIQLTYFQRMKDPLSLSYQTIIMLWMITNQAGLWLTTCLSLFYCSKIVRFSHTLLLCLANWV
SRKAPQMLLGAMLFSSACTLLCLGDFFSRSGFAFTTVLLMNNTEFNSQIVKLNFYYSSIFCTLGSIPP
FMFFLVSSGVLIISLGRHMRTMKANTKDSGDPSLEAHIKALISLISFLCLYVVSFCVALISVPLTMVW
HNKIGVMICVGILAACPSIHAAILISGNAKLRRAVETILLWVQSSLKVRAGHRADLRTPDLC*

FIG. 1I cT2R39 nucleotide sequence (SEQ ID NO:10)

atgatggaaacctgcaatcccccagaaaatgaattgtcaccatttggcatcctctcgatttt
aacaattacaggcactgaatgcatcgttggtatcattgcaaatgggttcatcatggctataa
atgcggctgaatggattaaaaataagacagtttccacaagtggcagagtcctgtttttcttg
agtgcatccagaatagctctccaaagcttcacaatgctagaaattaccttcagttcaacatc
cccacgtttttataatgaagatgttatgtatgacacattcaaagtaagtttcatgttcttaa
atcattgtagcctctggtttgctgcttggctcagtttcttctacttcgtgaagattgctgat
ttctcccacccccttttttctcaagctgaagtggagaatttccagactgatgccctggcttct
gtggctttcagtgcttatttccttgggctacagtatgctcctctccaatgacatctacactg
tgtattgtaacaattcttctatcccctcttccaactccactaagaaaaaatacttcactaag
accaatgtggtcaacctggttcttctctataacctggggatcttcattcctctaatcatgtt
catcctttcggccaccctgctgatcatctctctcaagagacatacactacacatggaaagca
atgccactggctgcagggaccccagcatggaggctcacataggggccatcagagcgaccagc
tactttctcattctctatattttcaattcagttgctctatttctctatatgtccaacatctt
tgatatcaacagctcctggaatattttgtgcaaattcatcatggctgcctaccctgctggtc
actccattctgctgattcaggacaaccctgggttgagaagagcctggaagcggcttcagcct
caagttcatttttacctaaaagagcagactccatga cT2R39 amino acid sequence (SEQ ID NO:26)

MMETCNPPENELSPFGILSILTITGTECIVGIIANGFIMAINAAEWIKNKTVSTSGRVLFFLSASRIA
LQSFTMLEITFSSTSPRFYNEDVMYDTFKVSFMFLNHCSLWFAAWLSFFYFVKIADFSHPLFLKLKWR
ISRLMPWLLWLSVLISLGYSMLLSNDIYTVYCNNSSIPSSNSTKKKYFTKTNVVNLVLLYNLGIFIPL
IMFILSATLLIISLKRHTLHMESNATGCRDPSMEAHIGAIRATSYFLILYIFNSVALFLYMSNIFDIN
SSWNILCKFIMAAYPAGHSILLIQDNPGLRRAWKRLQPQVHFYLKEQTP*

FIG. 1J

<u>cT2R40 nucleotide sequence</u> (SEQ ID NO:11)

atggccacagtgagcacagatgccacggatagagacatgtccaggtttaaaatcgtcctcaccttggt
ggtccccggaatagagtgcctcactggcatcgttgggaatggcttcatcacaatcatccatggggcca
agtgggccagaggcaaaaggctcccggtcactgactgcattctgctgatgctcagcttttccaggctc
ttactgcagatctggatgatgctggagaatatttacagtctactattccgggtcacttacaaccaaag
cacagtgtttatagtcttcaaagtcactgtcattttcctgaactatttcaacctctggcttgctgcct
ggctcaacatcttctattgtctgagaatcacaaacttggctcaccatgtgttcttcatgatgaagagg
aaaatcacggagctgatgcctcggcttctgggactgtcactgttcatctccttatgcttcagctttcc
tttctctacagatatcttccatgtgtacgtaaacagttccatccctatccgttcctccaataccaccg
agaagaagtacttctctgagaccaatgtggtcaacctggttcttctctataacctggggatcttcatt
cctctgatcatgttcatcctttcggccaccctgctgatcatctctctcaagagacacacactacacat
ggaaagcaatgccactggctgcagggaccccagcatggaggctcactttggggccatcagagcgacca
gctactttctcattctctacattttcaatgcagttgctctatttctttccatgtccaacatcttcgac
atcaacagctcctggaatattttgtgcaaaattgtcatggccgcctacccagctagccactcagtgct
actgatcttgggtaaccctgggctgagaagagcctggaagaggtttcagcaccatgttcctcttcacc
tgtaa

<u>cT2R40 amino acid sequence</u> (SEQ ID NO:27)

MATVSTDATDRDMSRFKIVLTLVVPGIECLTGIVGNGFITIIHGAKWARGKRLPVTDCILLMLSFSRL
LLQIWMMLENIYSLLFRVTYNQSTVFIVFKVTVIFLNYFNLWLAAWLNIFYCLRITNLAHHVFFMMKR
KITELMPRLLGLSLFISLCFSFPFSTDIFHVYVNSSIPIRSSNTTEKKYFSETNVVNLVLLYNLGIFI
PLIMFILSATLLIISLKRHTLHMESNATGCRDPSMEAHFGAIRATSYFLILYIFNAVALFLSMSNIFD
INSSWNILCKIVMAAYPASHSVLLILGNPGLRRAWKRFQHHVPLHL*

FIG. 1K

<u>cT2R41 nucleotide sequence</u> (SEQ ID NO:12)

atgcagcccgccgtgtccgccttcttcatgctgctctttgtcctgctgtgtgtcctggggatcctggc
caacggcttcatcgtgctggtgctgagcagggagaggatgcggcgggggaggctgctcccctccgacg
tgatcctccttagcctgggcgcctcccgcttctgcctgcagtgcattgggatgatgaacaacttttac
tactacctccacctggaggagtacagcacgggcccggctcggcaattctttggcctccactgggactt
cctgaactcggccaccttctggttcggctcttggctcagcgtcctcttctgcatgaagatcgccagct
tcacccaccccaccttcctctggctgaggtggcggctcccaggctcggtgccctggctcctcggggct
tccctcctgatctccttcctcgtcaccctgctcttcttttggggaaaccatgccgtgtatcaaggatt
cctaatcagaaaataccccgggaacatgaccttccagcagtggagcaggaggctggaaattcactatt
tcttgcccctgaaattcatcaccttgtcagtgccttgctctgtcttcctggtgtccatcgcactgttg
attaattccctgaggcgacacaggggggaggatgcggcgcagtggccacggcctgcaggaccccagcag
ccaggctcacaccagggctctgaagtccctcgtctccttcctcattctgtatgctctgtcctttgcgt
ccctggtcatcgatgctgcgggtttcttctgctcgcagagtgactggtactggccctggcagatttta
atctacctgtgcacctctgtccatccctatatcctcatcctcagcaacctccggctccgagggggtg
caggcagctacttctgttggtcaggggctcccagctggcctag

<u>cT2R41 amino acid sequence</u> (SEQ ID NO:28)

MQPAVSAFFMLLFVLLCVLGILANGFIVLVLSRERMRRGRLLPSDVILLSLGASRFCLQCIGMMNNFY
YYLHLEEYSTGPARQFFGLHWDFLNSATFWFGSWLSVLFCMKIASFTHPTFLWLRWRLPGSVPWLLGA
SLLISFLVTLLFFWGNHAVYQGFLIRKYPGNMTFQQWSRRLEIHYFLPLKFITLSVPCSVFLVSIALL
INSLRRHRGRMRRSGHGLQDPSSQAHTRALKSLVSFLILYALSFASLVIDAAGFFCSQSDWYWPWQIL
IYLCTSVHPYILILSNLRLRGGCRQLLLLVRGSQLA*

FIG. 1L

<u>cT2R42 nucleotide sequence</u> (SEQ ID NO:13)

atgttagctggattggatataatctttcttacactgtcaacagcagaattcataattggaatgttggg
gaatgcgttcattggactggtaaactgctctgaatgggtcaagaaccggaaaatctctttagctgact
tcattctcatctgcttggctatctccagaatcgctcagctgttggtgtcatggtttgaatcatttatg
atgggactatctccacttttcttttccacttataaactggcaaaatctattactttgctttggagaat
aactcatcatttggctacgtggtttagtacctgcctaagcattttctacctccttaagatagctcagt
tctctcattccttttcctctggctgaggtggagaatgaacagagtggttcttgcaattcttgtattt
tctttgttctttctactgtttgactttctaatgctagaaacattcaatgatctcttctcgaatgtcga
tgcaatggatgaaagtaatctgactttatatatatatgaaagtaaaacttttatgttaaaccttga
ttcttcttagtttttcctatatcattcctattattctgtccctgacctcattgctccttttatttctg
tccttggtaaaacacatcagaaatttgcagctcaactccatgggctccagggattccagcacacaggc
ccataaaaaagccattaaaatggtgatgtctttcctcttccttttcacagttcactttttttccatac
aattgtcaaattggatgtttttttatttggaacaagaagatcacaaagtttatcatgttggccgtt
tatgtctttccttcaagccactcactaattttgattctgggaaacagcaagctgagacagacagcctt
gaaggtactgtggcatcttaaaagctccctgaaaagagaaaaaccaaattcatctttaccgatagact
ttccagaatctttccaatga

<u>cT2R42 amino acid sequence</u> (SEQ ID NO:29)

MLAGLDIIFLTLSTAEFIIGMLGNAFIGLVNCSEWVKNRKISLADFILICLAISRIAQLLVSWFESFM
MGLSPLFFSTYKLAKSITLLWRITHHLATWFSTCLSIFYLLKIAQFSHSLFLWLRWRMNRVVLAILVF
SLFFLLFDFLMLETFNDLFSNVDAMDESNLTLYIYESKTFYVKTLILLSFSYIIPIILSLTSLLLLFL
SLVKHIRNLQLNSMGSRDSSTQAHKKAIKMVMSFLFLFTVHFFSIQLSNWMFFLFWNKKITKFIMLAV
YVFPSSHSLILILGNSKLRQTALKVLWHLKSSLKREKPNSSLPIDFPESFQ*

FIG. 1M

<u>cT2R43 nucleotide sequence</u> (SEQ ID NO:14)

atgctacctttactacagagcatttttttccatcctagtaatgacagaatttgttctaggaaattttgc
caatggcttcatagtgctggtgaactacattgcatgggtcaagagacaaaagatctcctcagctgatc
aaattctcactggtctggctgtctccagaattggtttactctgggtaatattaataaattggtatgca
actctgttgaatccagctttatatagcttagaagtaaggcttcttgttcatattgcctggacagcgaa
caatcatttagcatctggcttgctactagcctcagtgtattttatttgttcaaaatagccaatttct
ctaaccttatttttcttcgcctaaagtggagagttaaaagtgtagtttttgtgatgctgttggggtct
ttgttctttttggtttttcatgttgcagtggtaagcatatatgagcaaatgcagatgaaggaatatga
aggaaacatcactaggcagaccaaactgagggacattgcacagcttatgaatatgactgtattcacgc
taatgaactttgtaccctttgctatatccctaacatcttttctgctgttaatcttttccctgtggaaa
catctcaagaagatgcgatccggtggtaaaagatatcaagattccagcaccaaggtccacataaaagc
catgcagactgtgatctcttttcttttgttattagtttgttacttcctgactttaattgccatagttt
ggagttctaataggctgcagaacaagttgatcttcttgctttgcaaggctattggaatcctgtatcct
tcaagccactcatttatcctgatttggggaaacaagaagctcagagaggactttctgtcatttctgtg
gcagctgaagggctggctgaaaaaggatataagaggagcatcatgtgtcttctaggagaaaacaaat
tgatggagtctgtaatatttttttcttctacttctttttctaatgagtatgtaattgagcaatttcca
aagatttacctaaaaaagtcttttctctga

<u>cT2R43 amino acid sequence</u> (SEQ ID NO:30)

MLPLLQSIFSILVMTEFVLGNFANGFIVLVNYIAWVKRQKISSADQILTGLAVSRIGLLWVILINWYA
TLLNPALYSLEVRLLVHIAWTANNHFSIWLATSLSVFYLFKIANFSNLIFLRLKWRVKSVVFVMLLGS
LFFLVFHVAVVSIYEQMQMKEYEGNITRQTKLRDIAQLMNMTVFTLMNFVPFAISLTSFLLLIFSLWK
HLKKMRSGGKRYQDSSTKVHIKAMQTVISFLLLLVCYFLTLIAIVWSSNRLQNKLIFLLCKAIGILYP
SSHSFILIWGNKKLREDFLSFLWQLKGWLKKGYKRSIMCLLGENKLMESVIFFSSTSFSNEYVIEQFP
KIYLKKSFL*

FIG. 1N cT2R62 nucleotide sequence (SEQ ID NO:15)

atgtcctcctcacctacattgatcttcatggtcatcttcttcctggagtcgttggctgcaatgctgca
gaatggcttcatggttactgtgttgggcagggagtgggtgcgacgccggacgctgcctgcaggtgaca
tgattgtggcctccctggctgcctcctggttctgcctgcatggggtggccatcctgaacaacctcttg
atcttctttggttttcacttcgtaagggattattacaacaccctctggcactttgtcaacactctcac
tctctggctcactgcctggcttgctgtcttctactgtgtgaaggtcgccgtcttctctcacccggtct
tcttctggctgaaatggaggatttctcggttagtgcccaggctgctgctgggctccctggtcttagtt
ggcctgacagtcatctcatcagccattgtgactggaattctgaaacagatgattgcctccaagagttc
ccaaggaaacagcacctgggctgagagagtacaggccttctataggtcttttcatctatttgatgtaa
tgcttatgtggtcagttccattcctcctgttcttggtgtccatgctcttgcttgtgttctcactgtgc
cggcatttggggttgatgaggaactatagacaggacccatgtgatcctagcacccgggttcacacgat
ggccctgaagtcacttgtcttcttccttgtcttctacacaccatatttcctgtctctggttgttgttg
ctatagaaataacaaacttccagagtcactggtactgggcctgggaagtggtaacctatgcgagcatc
tgtctgcactccagcatgctggtgctaagcagccccaaactgagaaaggtcctgatgaccaggctttg
gaaagctctggacaaaggctga cT2R62 amino acid sequence (SEQ ID NO:31)

MSSSPTLIFMVIFFLESLAAMLQNGFMVTVLGREWVRRRTLPAGDMIVASLAASWFCLHGVAILNNLL
IFFGFHFVRDYYNTLWHFVNTLTLWLTAWLAVFYCVKVAVFSHPVFFWLKWRISRLVPRLLLGSLVLV
GLTVISSAIVTGILKQMIASKSSQGNSTWAERVQAFYRSFHLFDVMLMWSVPFLLFLVSMLLLVFSLC
RHLGLMRNYRQDPCDPSTRVHTMALKSLVFFLVFYTPYFLSLVVVAIEITNFQSHWYWAWEVVTYASI
CLHSSMLVLSSPKLRKVLMTRLWKALDKG*

FIG. 1O

<u>cT2R67 nucleotide sequence</u> (SEQ ID NO:16)

atgccatctagaattgaaaatgcttttctggtagcagcagcaggagaactcataactggaatgttggg
gaacggtttcattgtactagttaactgcattgacttggtgaagaatctaaagctctctactgctgact
gcatcctcaccagcctggctctttccagaatcattcttctttgtataatactacttgattcactttta
atggtgttttggcaacatctttatgccattgataagctagcaaaattcattagtgtttttggacact
aagcaatcacctaactacctggattgttacctgtctaaatgttttctacttctttaaaatagccaatt
tttcccacccctgtttcacctggctgaggtggagaattagcagagtgctacttgtgcttccactgggg
tctttattcttactgtttttcaactttgaattattagatacatttacgaatttctgggttaatctcta
tcaaagacatgaaagaaactcaatttggtccctagatgtaagtaaaactctgtatcttaacagcttga
ttgttttcagtttcatctacttaatcccctttcttctgtccctggcctctttgctcctttttatttctt
tccttaatgagacatatcaggaatgtgcaacggaactccagctctagggacttcagaacagaggccca
taaaagggccatgaaaatggtgatgtcttctctttttctttccatggttaattttacttccatcctat
taacaggatggttttccctttttactgcagaatcatcaggccaatttggctgtcctgttattatcgact
cttgtaccctcaggccactcatttattctaattttgggaaacaacaagttgagacaagctgcgttagg
tctactgtggcatcttaattgccacctgaaaatggtgaagcctttcgcttcctag

<u>cT2R67 amino acid sequence</u> (SEQ ID NO:32)

MPSRIENAFLVAAAGELITGMLGNGFIVLVNCIDLVKNLKLSTADCILTSLALSRIILLCIILLDSLL
MVFWQHLYAIDKLAKFISVFWTLSNHLTTWIVTCLNVFYFFKIANFSHPCFTWLRWRISRVLLVLPLG
SLFLLFFNFELLDTFTNFWVNLYQRHERNSIWSLDVSKTLYLNSLIVFSFIYLIPFLLSLASLLLLFL
SLMRHIRNVQRNSSSRDFRTEAHKRAMKMVMSSLFLSMVNFTSILLTGWFSLLLQNHQANLAVLLLST
LVPSGHSFILILGNNKLRQAALGLLWHLNCHLKMVKPFAS*

FIG. 1P

Table 5: Summary table of receptor–ligand interactions detailed in Figures 3–9.

| | cT2R1 | cT2R2 | cT2R3 | cT2R4 | cT2R5 | cT2R10 | cT2R38 | cT2R39 | cT2R41 | cT2R42 | cT2R43 | cT2R62 |
|---|---|---|---|---|---|---|---|---|---|---|---|---|
| Chloroquine | – | – | + | – | – | – | – | – | – | – | – | – |
| Cucurbitacin B | – | – | – | – | – | + | – | – | – | – | – | – |
| Colchicine | + | + | – | + | – | – | – | – | – | – | – | – |
| Menthol | + | – | – | – | – | – | – | – | – | – | – | – |
| Ofloxacin | – | + | – | – | – | – | – | – | – | – | – | – |
| 1,10-Phenathroline | + | + | – | – | + | – | – | – | – | – | – | – |
| Propylthiouracil | – | – | + | – | – | – | – | – | – | – | + | – |

+: The ligand elicited a clear dose dependent response from the receptor *in vitro.*
–: The ligand did not elicit a specific, dose dependent response from the receptor *in vitro.*

Shaded cells: These interactions are detailed further in the preceding Figures.

FIG. 10

SEQUENCE LISTING

```
<160> NUMBER OF SEQ ID NOS: 32

<210> SEQ ID NO 1
<211> LENGTH: 894
<212> TYPE: DNA
<213> ORGANISM: Canis familiaris

<400> SEQUENCE: 1

atgttagagt tttaccttat tatccatttt cttttcacag tgatgcaatt tctcatcggg     60

gttttagcaa atggcatcat tgtggtggtg aatggcactg agttgatcaa gcagagaaag    120

atgattccct tggctctcct tctttgctgt ctggcgattt ccaggatttg tctacaattg    180

atcatcttct tcatgaatct gggtactctc ttcttgattg aagtccccct acttgctgat    240

aattttgtaa ttttcgtgtt tgtaaatgaa ttgggacttt ggttcgccac atggcttggg    300

gtttactact gtgccaagat cgcccccata actcactcat tctttttctg gttgaagata    360

aggatatcca agtggatgcc atggctgatc ctcgggtcca tgatgtatgc atccgtccct    420

tctgttttct gcagcaaaca gatatgggtt tattcccaaa acgttttgtc cagccttttt    480

tccccaaacg caactcaaat caaagaaaca tctgctttac agattgcctt tcttattagg    540

ttattattgc cactgcttat ctttctcggt tccaccctac ttttgatatt ttccctgggg    600

agacacacct ggcagatgag aaacacagca acaggcccca gggaccctag cacaggtgtc    660

cacgtgagca cgatcctgtc cgttctatcc ttcctggtcc tctgcctctc ccactacatg    720

gcagctgctt tgctctcttt tcagatcttt cagctcagaa gcctcgtctt tctgatctgt    780

ctctgggtgt ttgggtccta tccttctgga cactctatga tcttaatttt aggaaatcct    840

aaattgaaac aaaatgcaaa gaagctcctc ctccacggga agtgctgcca gtga          894

<210> SEQ ID NO 2
<211> LENGTH: 912
<212> TYPE: DNA
<213> ORGANISM: Canis familiaris

<400> SEQUENCE: 2

atgatctcct ttttgtcagc tcttcctcat gttattgtta tgtcagcaga atttatcaca     60

gggattacag taaatggatt tcttatcatc atgaactgta aagaattgat caaaagcaga    120

aagccaacac cagtgcaact ccttttcata tgtataggga tgtcgagatt tggtctgctc    180

atggtgttaa tgatacaaag ttttttctct gtgttatttc cactctttta taaggtaaac    240

atttttggta cagcaatgtt gttcttttgg atgtttttta gctctgtcag tttctggttt    300

gccacctgcc tttctgtatt ttactgcctc aagatagcag gcttcactca atcctgtttt    360

ctttggctga aattcaggat ctcgaagtta atgccttggc tacttctggg aagtttgctg    420

gcctccatga gcattgcagc tctgtgtatt gaagcagatt accctaaaaa ggtggatgat    480

gatgccctca agaatgccac attgaagagg actgaaccca agataaggca aattagtgaa    540

atgctgcttg tcaacttggc attactattt cctctagcca tatttgtgat gtgcactttt    600

atgttattca tttctctcta taagcacact catcggatgc aaaatggatc tcatggtgtt    660

agaaatgcca gcacaaaagc ccatataaat gcattaaaaa cagtgataac attcttttgc    720
```

```
ttctttattt cttattttgc tgccttcatg gcaaatatga cattcagtat tccttatgga    780

agtcattgct tctttgtagt aaaggacata atggcagcat ttccctctgg tcattcaatt    840

ataatcctcc tgagtaattc taaataccaa caacctttca ggagacttct ctgcttcaaa    900

aagaatcaat ga                                                         912


<210> SEQ ID NO 3
<211> LENGTH: 951
<212> TYPE: DNA
<213> ORGANISM: Canis familiaris

<400> SEQUENCE: 3

atgtcagggc tggggaaatc cgtgttcctg gttctgtctg tcactcagtt cattctgggg     60

atgctgggga atggtttcat agtgttggtc aatggcagca gctggttcaa gaacaagaca    120

gtctctttgt ctgacgttat catcactaac ctggctctct ccaggattgt tctgctgtgg    180

attctcttgg ttgatggtgt tttaatggtc ttcttttcca aagtacatga tgaagggaca    240

gtaatggaaa ttattgatat tttctggaca tttacgaacc acctgagcat ttggcttgcc    300

acctgtctca gtgtcctcta ctgcctgaaa attgccagtt tctcccatcc gacgttcctc    360

tggctcaagt ggagagtttc cagagtggtc gtacagatga ttttgggtgc actgctctta    420

tcgtgtgcca gtgccatgtc tctggtccat gaatttaaga tctattctat tctcagtgga    480

attgctggta cagggaatgt gaccgagcac tttagaaaga agagaaatga ctataaagtg    540

gcccatgttc ttgggactct gtggaacctc cctcccctaa ttgtttctct ggcctcctac    600

tttctgctca tcttctccct gggaaggcac acacagcaga tgaagcacag tggcaccagc    660

tccagagatc tgagcacgga ggcccaccag agagccatca aaatcatcgt ctctttcctc    720

tttctcttcc tgctttactt tcttgccttt ttaattacat catccagtta tttcatacca    780

gaaactgaga tggttaagag agttggagta gttgttacaa tgttttaccc tgccagccac    840

tcattcgtta tcattctggg aaacaataag ctgaagcaga tgtttacgga gatgctgtgc    900

tgtgagcctg gttatctgaa gcctggattc aaaagacctt ttgccccata a             951


<210> SEQ ID NO 4
<211> LENGTH: 900
<212> TYPE: DNA
<213> ORGANISM: Canis familiaris

<400> SEQUENCE: 4

atgcttcaga tattcttttt atctgccatt attttctcag caattttgaa ttttgtggga     60

ctcattgtaa atctgtttat tgcagtggtc agttatagga cttggctcaa aagccataga    120

atttcctctt ctaattggat cctcttcagc ttgggcatca ccagatttct tatgctggga    180

ctgtttctac tcaacatcat ctacttcttc atctctccaa aaatggaaag gtcggtgcac    240

ctatcccact ttttcctgtc gtgttggatg tttttggact ctaatagtct ctggtttgta    300

accttgctca atgccttgta ctgcgtgaag attacggact tccaacttgg agtatttctc    360

ctgctgaagc gaaatctctc cccaaagatc cccaggctgt tgctagcctg tgtactgatt    420

tctgccttca ccactctcct gtatgttgtg ctcaaacaga catcatccct tcctgaattt    480

gtgactcaga gaaatggtac aggatgtggc atccatggga gtgtcttgtc tttggtgacc    540

tctttggtct tgcgctcagt tctccagttt atcattaatg tgacttctgc ttccttgttg    600

atacattcct tgaggagaca tatacagaag atgcagaaaa acaccactat tttttggaat    660
```

```
cctcagactg aagctcatgt gggcgctatg aagctgatga tctgtttcct catcctgtac    720

attccttact cagttgctac cttgctacat tatttccctt atggtgggat ggatttgaga    780

accagatcca tctgtttggt tatttccagc ttttaccctc caggacattc tattctcatt    840

atcctcacac atcctaaact gaaaacaaaa gcaaagaaga ttctttgttt caacaaatag    900


<210> SEQ ID NO 5
<211> LENGTH: 888
<212> TYPE: DNA
<213> ORGANISM: Canis familiaris

<400> SEQUENCE: 5

atgctgactg ctgccctacc actgctgatg gtggtggcag tggttgaatt tctcattggc     60

ttggtgggaa atggagtcct tatggtctgg agttttggtg aatgggtcag aaaattcaac    120

gggtcctcat acaacctcat tgtcctgggc ctggctgtct gccgatttct cctgcagtgt    180

ctgattatga tggacttaag cctgtttcca tttttccaga gtagccgttg gcttcactat    240

ctcagtatct tctggatcct ggtaagccag gccagcctgt ggtttgccac tttcctcagc    300

gtcttctact gcaggaagat catgaccctt gaacatcctg tctgcttgtg gctgaagcag    360

agggcctatt gcctgagtct ctggtgcctt ctggtgtacc tcatgatcag tttgttactt    420

gtagcacaca ttggcttaaa gccctataat ccttctcaag gcaacagcag cattctgtac    480

ccccttaaaa gctggcacta cctgtatata gtaaagctca acgcaggaag tggattgcct    540

ctcatggtgt ttcttgtttc ttctgggatg ctgattgtct ctttgtatag acaccacaag    600

aagatggagg tacatacagc tggtaggaga gatgctcagg ccaaggctca catcactgta    660

ctgaagtcct tgggctgctt ccttatcctt catgtgattt atatcctggc cagccccttt    720

tccattacct ccaagtcttc tgctgatctc ctcgttgtct tcatctctga gacagtcatg    780

gctgcctatc cttctcttca ttctgtcatt ctgatcctgg ggaatcccag gatgaagcag    840

acttgtcaga gaattctgtg gaagacagtg tgtgcttgga aatcctag                 888


<210> SEQ ID NO 6
<211> LENGTH: 939
<212> TYPE: DNA
<213> ORGANISM: Canis familiaris

<400> SEQUENCE: 6

atgccggata aagtggagag catcttaatg ctcgtagcag ctggagaatt ttcaatgggg     60

attttaggga atacattcat tggattggta aactgcatag gctggatcaa gaagaggaag    120

attgcctcca ttgatttaat cctcacaagt ctggccatat ccagaatttg tctattatgt    180

ataatactat tagattgttt tatattggtg ctgtatccag atgtctatgc taccggtaaa    240

caaatgagaa taattgactt cttctggaca ctaaccaacc atttaagtgt ctggtttgcc    300

acctgtctca gcattttcta tttcctcaag attgcgaatt tcttccatcc ccttttcctc    360

tggatgaagt ggagaattga cagtgcgatt cctaggatcc tgctgggatg cttggccctt    420

tctgtgttta ttagccttgt tgtcactgag aatttgaatg atgatttcag atgttgtgtt    480

aggacaaaga agaaaacaaa cttaactgtg agatgcagag taaagaaagc taaatattct    540

tccatcaaga tttgcctcaa cctgttaacg ctattcccct tttctgtgtc cctgatctca    600

tttctcctct tgatcctctc cctctggaga cataccaggc agatgaagtt caatgccaca    660

gggtgtagag acttcagcat agaagcccac atgggagcca tgaaagctgt catctccttt    720

ctcctccttt tcatcgccta ctatttggcc tttcttgtag ccacctctag ctactttatg    780
```

```
ccagagactg aattagctgt gatcattggt gagttgatag ctctaatcta tccctcgagc    840

cattcgttta tcctaattct ggggagcaat aaattaagac aggcatctct aagggtacta    900

tggaaagtaa aatatgtctt aaaaagaaga aacttctaa                           939
```

<210> SEQ ID NO 7
<211> LENGTH: 969
<212> TYPE: DNA
<213> ORGANISM: Canis familiaris

<400> SEQUENCE: 7

```
atgctaagca tactggaagg cctcctcatt tttatagctg ttagtgaatc aatactggga     60

gttttaggga atggatttat tggacttgtc aattgtattg actgtgtgaa gaacaaaaag    120

ttttctatgg ttggctttat tctcactggc ttagctactt ccagaatttg tctgatattg    180

ataataatta cagatggatt tataaagata ttctctccag atatgtattc ctctggtaac    240

ttaattgatt atattagtta cctatgggta attatcaatc aatcaagtat ctggtttgcc    300

accagcctca gcatcttcta tttcctgaag atagcaaatt tttcccacca catttttctc    360

tggctgaagg gtagaatcaa tagcgttctt ccccttctga tgggatcctt gtttatttca    420

tggttattta cttttccaca aattgtgaag attattaatg ataatagaat gaagagtaga    480

aatacaacct ggcagctcaa catgcagaaa agtgaattct ttactaagca gattttactc    540

aacctaggag tcattcttct ctttactcta tgcctgatta catgtttctt gctaatcgtt    600

tccctttgga gacacaacag gcacatgcaa ttgaatgtca ctggactccg agaccccagt    660

acagaagcac atgtgaaagc aatgaaaatt ttggtatctt ttatcatcct ctttatcttg    720

tattttatag gcattgccat agaaatatca tgtttcattc tgccagaaaa caaactgctg    780

tttatttttg gtatgatgac cacagccatc tatccctggg gtcattcatt tatcctaatt    840

ctaggaaaca gcaagctaaa gcaagcttct ttgaagaccc tgcagcaact caagtgcgag    900

gcaaggagac tgctcacagc tgcacagatc catgtggggg gaaatggatg ttccaggaga    960

ataatctag                                                            969
```

<210> SEQ ID NO 8
<211> LENGTH: 945
<212> TYPE: DNA
<213> ORGANISM: Canis familiaris

<400> SEQUENCE: 8

```
atggcaggca caatgaagaa tgtatttatg atgatttttg ccggagaatt cataataggg     60

attttgggaa atggattcat tatattggtt aactgtatcg attggatcag gagctggaag    120

ttcttcctga ttgactttat tcttacctgc ttagccattt ccaggatatt tctgctgtgc    180

ataataatgt taggcatagg tctagatata atttgtaagg aaatatggta caatgataat    240

caactgataa cctttgaagt cctctggaca ggatgcaatt atttctgcac aatctgtact    300

gtgtgcctca gtgtcttcta cttcctcaag atagccaact cttccaatcc catttcttc     360

tggctaaaac ggagaattca cagactgctt ctcattattg tcctgggagc agtcttctat    420

ttctgcttgt ccctgctttt gaaggatata gtatttaaga acatgatcaa aaccaaggta    480

aacactgaaa gcaatgtgac attaaatttc acagcgagaa aatatgattt actaacttct    540

aatatattcc tgaacatgct attcgtcatc ccctttgcag tgtctctggc ttcctttgtc    600

cttttgatcc attccttatg gaaccatacc aggcggatga agggcattga ttctggggat    660
```

-continued

```
cttatcacag aggcccatgt aagagccatg aagtttatga tttcattcct gctattcttc    720

tttatatact atttgagcaa tattataata tattttgcct atgttgttct ggatagtctg    780

gtggcaaaaa tttttgctaa tatattagta ttttcctatc cttctggcca tccatttctt    840

ctgattttat ggaactgcaa attgaaacag gcttctctct atgtcctgag gaagctgaag    900

tggtgcatga atctaaggaa acccgcatac ataaagcata cctga                    945
```

<210> SEQ ID NO 9
<211> LENGTH: 1005
<212> TYPE: DNA
<213> ORGANISM: Canis familiaris

<400> SEQUENCE: 9

```
atgttggctc tgactcctgt tataactgtg tcctatgaag tcaagagtgc atttatgttc     60

ctttcagtac tggagctcgc agtggggatc ctgaccaatg ccttcatttt cttggtgaat    120

ttttgggatg tggtgaggag gcagccactg agcaactgcg atcttatcct tctgagtctc    180

agcctcactc gacttttcct gcatgggctg ctgtttctgg atgccatcca gcttacatac    240

ttccagcgga tgaaagaccc actgagcctc agctaccaga ccatcatcat gctctggatg    300

atcacaaacc aagctgggct ctggctcacc acctgtctca gtcttttcta ctgctccaag    360

attgtccgtt tctctcatac cctccttctc tgcttggcaa actgggtctc caggaaggca    420

ccccagatgc tcctgggtgc catgcttttc tcttctgcct gcactctcct ctgtttgggg    480

gacttcttta gtagatctgg ctttgcattc acaactgtgc tactcatgaa taatacagaa    540

tttaattcac aaattgtaaa actcaatttc tattattcct ccatcttctg taccctgggg    600

tcaatccctc ctttcatgtt ttttctggtt tcttctgggg tgctgattat ctctctggga    660

aggcacatga gaacaatgaa ggccaacacc aaagactccg gtgaccccag cctggaggcc    720

catatcaaag cactcatatc tctcatctcc tttctctgcc tctatgtggt gtcattctgt    780

gttgcccctta tctcagtgcc tttaaccatg gtgtggcaca acaagatcgg ggtaatgatc    840

tgtgtaggga tcctagcagc ttgtccctct atacatgcag ccatcctgat ctcaggcaat    900

gccaagctga ggagagctgt ggagaccatt ctactctggg ttcagagcag ccttaaggta    960

agggcaggcc acagggcaga tctcaggact ccagatctat gttga                   1005
```

<210> SEQ ID NO 10
<211> LENGTH: 966
<212> TYPE: DNA
<213> ORGANISM: Canis familiaris

<400> SEQUENCE: 10

```
atgatggaaa cctgcaatcc cccagaaaat gaattgtcac catttggcat cctctcgatt     60

ttaacaatta caggcactga atgcatcgtt ggtatcattg caaatgggtt catcatggct    120

ataaatgcgg ctgaatggat taaaaataag acagtttcca caagtggcag agtcctgttt    180

ttcttgagtg catccagaat agctctccaa agcttcacaa tgctagaaat taccttcagt    240

tcaacatccc cacgttttta taatgaagat gttatgtatg acacattcaa agtaagtttc    300

atgttcttaa atcattgtag cctctggttt gctgcttggc tcagtttctt ctacttcgtg    360

aagattgctg atttctccca ccccctttt ctcaagctga agtggagaat ttccagactg    420

atgccctggc ttctgtggct ttcagtgctt atttccttgg gctacagtat gctcctctcc    480

aatgacatct acactgtgta ttgtaacaat tcttctatcc cctcttccaa ctccactaag    540

aaaaaatact tcactaagac caatgtggtc aacctggttc ttctctataa cctggggatc    600
```

-continued

```
ttcattcctc taatcatgtt catcctttcg gccaccctgc tgatcatctc tctcaagaga    660

catacactac acatggaaag caatgccact ggctgcaggg accccagcat ggaggctcac    720

ataggggcca tcagagcgac cagctacttt ctcattctct atattttcaa ttcagttgct    780

ctatttctct atatgtccaa catctttgat atcaacagct cctggaatat tttgtgcaaa    840

ttcatcatgg ctgcctaccc tgctggtcac tccattctgc tgattcagga caaccctggg    900

ttgagaagag cctggaagcg gcttcagcct caagttcatt tttacctaaa agagcagact    960

ccatga                                                               966
```

```
<210> SEQ ID NO 11
<211> LENGTH: 957
<212> TYPE: DNA
<213> ORGANISM: Canis familiaris

<400> SEQUENCE: 11

atggccacag tgagcacaga tgccacggat agagacatgt ccaggtttaa aatcgtcctc     60

accttggtgg tccccggaat agagtgcctc actggcatcg ttgggaatgg cttcatcaca    120

atcatccatg gggccaagtg ggccagaggc aaaaggctcc cggtcactga ctgcattctg    180

ctgatgctca gcttttccag gctcttactg cagatctgga tgatgctgga gaatatttac    240

agtctactat tccgggtcac ttacaaccaa agcacagtgt ttatagtctt caaagtcact    300

gtcattttcc tgaactattt caacctctgg cttgctgcct ggctcaacat cttctattgt    360

ctgagaatca caaacttggc tcaccatgtg ttcttcatga tgaagaggaa aatcacggag    420

ctgatgcctc ggcttctggg actgtcactg ttcatctcct tatgcttcag ctttcctttc    480

tctacagata tcttccatgt gtacgtaaac agttccatcc ctatccgttc ctccaatacc    540

accgagaaga agtacttctc tgagaccaat gtggtcaacc tggttcttct ctataacctg    600

gggatcttca ttcctctgat catgttcatc ctttcggcca ccctgctgat catctctctc    660

aagagacaca cactacacat ggaaagcaat gccactggct gcagggaccc cagcatggag    720

gctcactttg gggccatcag agcgaccagc tactttctca ttctctacat tttcaatgca    780

gttgctctat ttctttccat gtccaacatc ttcgacatca acagctcctg gaatattttg    840

tgcaaaattg tcatggccgc ctacccagct agccactcag tgctactgat cttgggtaac    900

cctgggctga gaagagcctg gaagaggttt cagcaccatg ttcctcttca cctgtaa       957
```

```
<210> SEQ ID NO 12
<211> LENGTH: 927
<212> TYPE: DNA
<213> ORGANISM: Canis familiaris

<400> SEQUENCE: 12

atgcagcccg ccgtgtccgc cttcttcatg ctgctctttg tcctgctgtg tgtcctgggg     60

atcctggcca acggcttcat cgtgctggtg ctgagcaggg agaggatgcg gcgggggagg    120

ctgctcccct ccgacgtgat cctccttagc ctgggcgcct cccgcttctg cctgcagtgc    180

attgggatga tgaacaactt ttactactac ctccacctgg aggagtacag cacgggcccg    240

gctcggcaat tctttggcct ccactgggac ttcctgaact cggccacctt ctggttcggc    300

tcttggctca gcgtcctctt ctgcatgaag atcgccagct tcacccaccc caccttcctc    360

tggctgaggt ggcggctccc aggctcggtg ccctggctcc tcggggcttc cctcctgatc    420

tccttcctcg tcaccctgct cttcttttgg ggaaaccatg ccgtgtatca aggattccta    480
```

-continued

```
atcagaaaat accccgggaa catgaccttc cagcagtgga gcaggaggct ggaaattcac    540

tatttcttgc ccctgaaatt catcaccttg tcagtgcctt gctctgtctt cctggtgtcc    600

atcgcactgt tgattaattc cctgaggcga cacaggggga ggatgcggcg cagtggccac    660

ggcctgcagg accccagcag ccaggctcac accagggctc tgaagtccct cgtctccttc    720

ctcattctgt atgctctgtc ctttgcgtcc ctggtcatcg atgctgcggg tttcttctgc    780

tcgcagagtg actggtactg gccctggcag attttaatct acctgtgcac ctctgtccat    840

ccctatatcc tcatcctcag caacctccgg ctccgagggg ggtgcaggca gctacttctg    900

ttggtcaggg gctcccagct ggcctag                                        927
```

```
<210> SEQ ID NO 13
<211> LENGTH: 972
<212> TYPE: DNA
<213> ORGANISM: Canis familiaris

<400> SEQUENCE: 13

atgttagctg gattggatat aatctttctt acactgtcaa cagcagaatt cataattgga     60

atgttgggga atgcgttcat tggactggta aactgctctg aatgggtcaa gaaccggaaa    120

atctctttag ctgacttcat tctcatctgc ttggctatct ccagaatcgc tcagctgttg    180

gtgtcatggt ttgaatcatt tatgatggga ctatctccac ttttcttttc cacttataaa    240

ctggcaaaat ctattacttt gctttggaga ataactcatc atttggctac gtggtttagt    300

acctgcctaa gcattttcta cctccttaag atagctcagt tctctcattc ccttttcctc    360

tggctgaggt ggagaatgaa cagagtggtt cttgcaattc ttgtattttc tttgttcttt    420

ctactgtttg actttctaat gctagaaaca ttcaatgatc tcttctcgaa tgtcgatgca    480

atggatgaaa gtaatctgac tttatatata tatgaaagta aaacttttta tgttaaaacc    540

ttgattcttc ttagtttttc ctatatcatt cctattattc tgtccctgac ctcattgctc    600

cttttatttc tgtccttggt aaaacacatc agaaatttgc agctcaactc catgggctcc    660

agggattcca gcacacaggc ccataaaaaa gccattaaaa tggtgatgtc tttcctcttc    720

cttttcacag ttcacttttt ttccatacaa ttgtcaaatt ggatgttttt tttattttgg    780

aacaagaaga tcacaaagtt tatcatgttg gccgtttatg tctttccttc aagccactca    840

ctaatttgga ttctgggaaa cagcaagctg agacagacag ccttgaaggt actgtggcat    900

cttaaaagct ccctgaaaag agaaaaacca aattcatctt taccgataga ctttccagaa    960

tctttccaat ga                                                        972
```

```
<210> SEQ ID NO 14
<211> LENGTH: 1050
<212> TYPE: DNA
<213> ORGANISM: Canis familiaris

<400> SEQUENCE: 14

atgctacctt tactacagag catttttttcc atcctagtaa tgacagaatt tgttctagga     60

aattttgcca atggcttcat agtgctggtg aactacattg catgggtcaa gagacaaaag    120

atctcctcag ctgatcaaat tctcactggt ctggctgtct ccagaattgg tttactctgg    180

gtaatattaa taaattggta tgcaactctg ttgaatccag ctttatatag cttagaagta    240

aggcttcttg ttcatattgc ctggacagcg aacaatcatt ttagcatctg gcttgctact    300

agcctcagtg tattttattt gttcaaaata gccaatttct ctaaccttat ttttcttcgc    360

ctaaagtgga gagttaaaag tgtagttttt gtgatgctgt tggggtcttt gttctttttg    420
```

gtttttcatg ttgcagtggt aagcatatat gagcaaatgc agatgaagga atatgaagga 480
aacatcacta ggcagaccaa actgagggac attgcacagc ttatgaatat gactgtattc 540
acgctaatga actttgtacc ctttgctata tccctaacat cttttctgct gttaatcttt 600
tccctgtgga aacatctcaa gaagatgcga tccggtggta aaagatatca agattccagc 660
accaaggtcc acataaaagc catgcagact gtgatctctt ttcttttgtt attagtttgt 720
tacttcctga ctttaattgc catagtttgg agttctaata ggctgcagaa caagttgatc 780
ttcttgcttt gcaaggctat tggaatcctg tatccttcaa gccactcatt tatcctgatt 840
tggggaaaca agaagctcag agaggacttt ctgtcatttc tgtggcagct gaagggctgg 900
ctgaaaaaag gatataagag gagcatcatg tgtcttctag gagaaaacaa attgatggag 960
tctgtaatat ttttttcttc tacttctttt tctaatgagt atgtaattga gcaatttcca 1020
aagatttacc taaaaaagtc ttttctctga 1050

<210> SEQ ID NO 15
<211> LENGTH: 906
<212> TYPE: DNA
<213> ORGANISM: Canis familiaris

<400> SEQUENCE: 15
atgtcctcct cacctacatt gatcttcatg gtcatcttct tcctggagtc gttggctgca 60
atgctgcaga atggcttcat ggttactgtg ttgggcaggg agtgggtgcg acgccggacg 120
ctgcctgcag gtgacatgat tgtggcctcc ctggctgcct cctggttctg cctgcatggg 180
gtggccatcc tgaacaacct cttgatcttc tttggttttc acttcgtaag ggattattac 240
aacaccctct ggcactttgt caacactctc actctctggc tcactgcctg gcttgctgtc 300
ttctactgtg tgaaggtcgc cgtcttctct cacccggtct tcttctggct gaaatggagg 360
atttctcggt tagtgcccag gctgctgctg ggctccctgg tcttagttgg cctgacagtc 420
atctcatcag ccattgtgac tggaattctg aaacagatga ttgcctccaa gagttcccaa 480
ggaaacagca cctgggctga gagagtacag gccttctata ggtcttttca tctatttgat 540
gtaatgctta tgtggtcagt tccattcctc ctgttcttgg tgtccatgct cttgcttgtg 600
ttctcactgt gccggcattt ggggttgatg aggaactata gacaggaccc atgtgatcct 660
agcacccggg ttcacacgat ggccctgaag tcacttgtct tcttccttgt cttctacaca 720
ccatatttcc tgtctctggt tgttgttgct atagaaataa caaacttcca gagtcactgg 780
tactgggcct gggaagtggt aacctatgcg agcatctgtc tgcactccag catgctggtg 840
ctaagcagcc ccaaactgag aaaggtcctg atgaccaggc tttggaaagc tctggacaaa 900
ggctga 906

<210> SEQ ID NO 16
<211> LENGTH: 939
<212> TYPE: DNA
<213> ORGANISM: Canis familiaris

<400> SEQUENCE: 16
atgccatcta gaattgaaaa tgcttttctg gtagcagcag caggagaact cataactgga 60
atgttgggga acggtttcat tgtactagtt aactgcattg acttggtgaa gaatctaaag 120
ctctctactg ctgactgcat cctcaccagc ctggctcttt ccagaatcat tcttctttgt 180
ataatactac ttgattcact tttaatggtg ttttggcaac atctttatgc cattgataag 240

-continued

```
ctagcaaaat tcattagtgt tttttggaca ctaagcaatc acctaactac ctggattgtt    300

acctgtctaa atgttttcta cttctttaaa atagccaatt tttcccaccc ctgtttcacc    360

tggctgaggt ggagaattag cagagtgcta cttgtgcttc cactggggtc tttattctta    420

ctgtttttca actttgaatt attagataca tttacgaatt tctgggttaa tctctatcaa    480

agacatgaaa gaaactcaat ttggtcccta gatgtaagta aaactctgta tcttaacagc    540

ttgattgttt tcagtttcat ctacttaatc ccctttcttc tgtccctggc ctctttgctc    600

cttttatttc tttccttaat gagacatatc aggaatgtgc aacggaactc cagctctagg    660

gacttcagaa cagaggccca taaaagggcc atgaaaatgg tgatgtcttc tctttttctt    720

tccatggtta attttacttc catcctatta acaggatggt tttccctttt actgcagaat    780

catcaggcca atttggctgt cctgttatta tcgactcttg taccctcagg ccactcattt    840

attctaattt tgggaaacaa caagttgaga caagctgcgt taggtctact gtggcatctt    900

aattgccacc tgaaaatggt gaagcctttc gcttcctag                           939


<210> SEQ ID NO 17
<211> LENGTH: 297
<212> TYPE: PRT
<213> ORGANISM: Canis familiaris

<400> SEQUENCE: 17

Met Leu Glu Phe Tyr Leu Ile Ile His Phe Leu Phe Thr Val Met Gln
1               5                   10                  15

Phe Leu Ile Gly Val Leu Ala Asn Gly Ile Ile Val Val Val Asn Gly
            20                  25                  30

Thr Glu Leu Ile Lys Gln Arg Lys Met Ile Pro Leu Ala Leu Leu Leu
        35                  40                  45

Cys Cys Leu Ala Ile Ser Arg Ile Cys Leu Gln Leu Ile Ile Phe Phe
    50                  55                  60

Met Asn Leu Gly Thr Leu Phe Leu Ile Glu Val Pro Leu Leu Ala Asp
65                  70                  75                  80

Asn Phe Val Ile Phe Val Phe Val Asn Glu Leu Gly Leu Trp Phe Ala
                85                  90                  95

Thr Trp Leu Gly Val Tyr Tyr Cys Ala Lys Ile Ala Pro Ile Thr His
            100                 105                 110

Ser Phe Phe Phe Trp Leu Lys Ile Arg Ile Ser Lys Trp Met Pro Trp
        115                 120                 125

Leu Ile Leu Gly Ser Met Met Tyr Ala Ser Val Pro Ser Val Phe Cys
    130                 135                 140

Ser Lys Gln Ile Trp Val Tyr Ser Gln Asn Val Leu Ser Ser Leu Phe
145                 150                 155                 160

Ser Pro Asn Ala Thr Gln Ile Lys Glu Thr Ser Ala Leu Gln Ile Ala
                165                 170                 175

Phe Leu Ile Arg Leu Leu Leu Pro Leu Leu Ile Phe Leu Gly Ser Thr
            180                 185                 190

Leu Leu Leu Ile Phe Ser Leu Gly Arg His Thr Trp Gln Met Arg Asn
        195                 200                 205

Thr Ala Thr Gly Pro Arg Asp Pro Ser Thr Gly Val His Val Ser Thr
    210                 215                 220

Ile Leu Ser Val Leu Ser Phe Leu Val Leu Cys Leu Ser His Tyr Met
225                 230                 235                 240

Ala Ala Ala Leu Leu Ser Phe Gln Ile Phe Gln Leu Arg Ser Leu Val
                245                 250                 255
```

```
Phe Leu Ile Cys Leu Trp Val Phe Gly Ser Tyr Pro Ser Gly His Ser
            260                 265                 270

Met Ile Leu Ile Leu Gly Asn Pro Lys Leu Lys Gln Asn Ala Lys Lys
        275                 280                 285

Leu Leu Leu His Gly Lys Cys Cys Gln
    290                 295


<210> SEQ ID NO 18
<211> LENGTH: 303
<212> TYPE: PRT
<213> ORGANISM: Canis familiaris

<400> SEQUENCE: 18

Met Ile Ser Phe Leu Ser Ala Leu Pro His Val Ile Val Met Ser Ala
1               5                   10                  15

Glu Phe Ile Thr Gly Ile Thr Val Asn Gly Phe Leu Ile Ile Met Asn
            20                  25                  30

Cys Lys Glu Leu Ile Lys Ser Arg Lys Pro Thr Pro Val Gln Leu Leu
        35                  40                  45

Phe Ile Cys Ile Gly Met Ser Arg Phe Gly Leu Leu Met Val Leu Met
    50                  55                  60

Ile Gln Ser Phe Phe Ser Val Leu Phe Pro Leu Phe Tyr Lys Val Asn
65                  70                  75                  80

Ile Phe Gly Thr Ala Met Leu Phe Phe Trp Met Phe Phe Ser Ser Val
                85                  90                  95

Ser Phe Trp Phe Ala Thr Cys Leu Ser Val Phe Tyr Cys Leu Lys Ile
            100                 105                 110

Ala Gly Phe Thr Gln Ser Cys Phe Leu Trp Leu Lys Phe Arg Ile Ser
        115                 120                 125

Lys Leu Met Pro Trp Leu Leu Leu Gly Ser Leu Leu Ala Ser Met Ser
    130                 135                 140

Ile Ala Ala Leu Cys Ile Glu Ala Asp Tyr Pro Lys Lys Val Asp Asp
145                 150                 155                 160

Asp Ala Leu Lys Asn Ala Thr Leu Lys Arg Thr Glu Pro Lys Ile Arg
                165                 170                 175

Gln Ile Ser Glu Met Leu Leu Val Asn Leu Ala Leu Leu Phe Pro Leu
            180                 185                 190

Ala Ile Phe Val Met Cys Thr Phe Met Leu Phe Ile Ser Leu Tyr Lys
        195                 200                 205

His Thr His Arg Met Gln Asn Gly Ser His Gly Val Arg Asn Ala Ser
    210                 215                 220

Thr Lys Ala His Ile Asn Ala Leu Lys Thr Val Ile Thr Phe Phe Cys
225                 230                 235                 240

Phe Phe Ile Ser Tyr Phe Ala Ala Phe Met Ala Asn Met Thr Phe Ser
                245                 250                 255

Ile Pro Tyr Gly Ser His Cys Phe Phe Val Val Lys Asp Ile Met Ala
            260                 265                 270

Ala Phe Pro Ser Gly His Ser Ile Ile Ile Leu Leu Ser Asn Ser Lys
        275                 280                 285

Tyr Gln Gln Pro Phe Arg Arg Leu Leu Cys Phe Lys Lys Asn Gln
    290                 295                 300


<210> SEQ ID NO 19
<211> LENGTH: 316
<212> TYPE: PRT
```

-continued

<213> ORGANISM: Canis familiaris

<400> SEQUENCE: 19

Met Ser Gly Leu Gly Lys Ser Val Phe Leu Val Leu Ser Val Thr Gln
1 5 10 15

Phe Ile Leu Gly Met Leu Gly Asn Gly Phe Ile Val Leu Val Asn Gly
20 25 30

Ser Ser Trp Phe Lys Asn Lys Thr Val Ser Leu Ser Asp Val Ile Ile
35 40 45

Thr Asn Leu Ala Leu Ser Arg Ile Val Leu Leu Trp Ile Leu Leu Val
50 55 60

Asp Gly Val Leu Met Val Phe Phe Ser Lys Val His Asp Glu Gly Thr
65 70 75 80

Val Met Glu Ile Ile Asp Ile Phe Trp Thr Phe Thr Asn His Leu Ser
85 90 95

Ile Trp Leu Ala Thr Cys Leu Ser Val Leu Tyr Cys Leu Lys Ile Ala
100 105 110

Ser Phe Ser His Pro Thr Phe Leu Trp Leu Lys Trp Arg Val Ser Arg
115 120 125

Val Val Val Gln Met Ile Leu Gly Ala Leu Leu Leu Ser Cys Ala Ser
130 135 140

Ala Met Ser Leu Val His Glu Phe Lys Ile Tyr Ser Ile Leu Ser Gly
145 150 155 160

Ile Ala Gly Thr Gly Asn Val Thr Glu His Phe Arg Lys Lys Arg Asn
165 170 175

Asp Tyr Lys Val Ala His Val Leu Gly Thr Leu Trp Asn Leu Pro Pro
180 185 190

Leu Ile Val Ser Leu Ala Ser Tyr Phe Leu Leu Ile Phe Ser Leu Gly
195 200 205

Arg His Thr Gln Gln Met Lys His Ser Gly Thr Ser Ser Arg Asp Leu
210 215 220

Ser Thr Glu Ala His Gln Arg Ala Ile Lys Ile Ile Val Ser Phe Leu
225 230 235 240

Phe Leu Phe Leu Leu Tyr Phe Leu Ala Phe Leu Ile Thr Ser Ser Ser
245 250 255

Tyr Phe Ile Pro Glu Thr Glu Met Val Lys Arg Val Gly Val Val Val
260 265 270

Thr Met Phe Tyr Pro Ala Ser His Ser Phe Val Ile Ile Leu Gly Asn
275 280 285

Asn Lys Leu Lys Gln Met Phe Thr Glu Met Leu Cys Cys Glu Pro Gly
290 295 300

Tyr Leu Lys Pro Gly Phe Lys Arg Pro Phe Ala Pro
305 310 315

<210> SEQ ID NO 20
<211> LENGTH: 299
<212> TYPE: PRT
<213> ORGANISM: Canis familiaris

<400> SEQUENCE: 20

Met Leu Gln Ile Phe Phe Leu Ser Ala Ile Ile Phe Ser Ala Ile Leu
1 5 10 15

Asn Phe Val Gly Leu Ile Val Asn Leu Phe Ile Ala Val Val Ser Tyr
20 25 30

Arg Thr Trp Leu Lys Ser His Arg Ile Ser Ser Ser Asn Trp Ile Leu

-continued

```
        35                  40                  45

Phe Ser Leu Gly Ile Thr Arg Phe Leu Met Leu Gly Leu Phe Leu Leu
    50                  55                  60

Asn Ile Ile Tyr Phe Phe Ile Ser Pro Lys Met Glu Arg Ser Val His
65                  70                  75                  80

Leu Ser His Phe Phe Leu Ser Cys Trp Met Phe Leu Asp Ser Asn Ser
                85                  90                  95

Leu Trp Phe Val Thr Leu Leu Asn Ala Leu Tyr Cys Val Lys Ile Thr
            100                 105                 110

Asp Phe Gln Leu Gly Val Phe Leu Leu Leu Lys Arg Asn Leu Ser Pro
        115                 120                 125

Lys Ile Pro Arg Leu Leu Leu Ala Cys Val Leu Ile Ser Ala Phe Thr
    130                 135                 140

Thr Leu Leu Tyr Val Val Leu Lys Gln Thr Ser Ser Leu Pro Glu Phe
145                 150                 155                 160

Val Thr Gln Arg Asn Gly Thr Gly Cys Gly Ile His Gly Ser Val Leu
                165                 170                 175

Ser Leu Val Thr Ser Leu Val Leu Arg Ser Val Leu Gln Phe Ile Ile
            180                 185                 190

Asn Val Thr Ser Ala Ser Leu Leu Ile His Ser Leu Arg Arg His Ile
        195                 200                 205

Gln Lys Met Gln Lys Asn Thr Thr Ile Phe Trp Asn Pro Gln Thr Glu
    210                 215                 220

Ala His Val Gly Ala Met Lys Leu Met Ile Cys Phe Leu Ile Leu Tyr
225                 230                 235                 240

Ile Pro Tyr Ser Val Ala Thr Leu Leu His Tyr Phe Pro Tyr Gly Gly
                245                 250                 255

Met Asp Leu Arg Thr Arg Ser Ile Cys Leu Val Ile Ser Ser Phe Tyr
            260                 265                 270

Pro Pro Gly His Ser Ile Leu Ile Ile Leu Thr His Pro Lys Leu Lys
        275                 280                 285

Thr Lys Ala Lys Lys Ile Leu Cys Phe Asn Lys
    290                 295


<210> SEQ ID NO 21
<211> LENGTH: 295
<212> TYPE: PRT
<213> ORGANISM: Canis familiaris

<400> SEQUENCE: 21

Met Leu Thr Ala Ala Leu Pro Leu Leu Met Val Val Ala Val Val Glu
1               5                   10                  15

Phe Leu Ile Gly Leu Val Gly Asn Gly Val Leu Met Val Trp Ser Phe
            20                  25                  30

Gly Glu Trp Val Arg Lys Phe Asn Gly Ser Ser Tyr Asn Leu Ile Val
        35                  40                  45

Leu Gly Leu Ala Val Cys Arg Phe Leu Leu Gln Cys Leu Ile Met Met
    50                  55                  60

Asp Leu Ser Leu Phe Pro Phe Phe Gln Ser Ser Arg Trp Leu His Tyr
65                  70                  75                  80

Leu Ser Ile Phe Trp Ile Leu Val Ser Gln Ala Ser Leu Trp Phe Ala
                85                  90                  95

Thr Phe Leu Ser Val Phe Tyr Cys Arg Lys Ile Met Thr Leu Glu His
            100                 105                 110
```

-continued

```
Pro Val Cys Leu Trp Leu Lys Gln Arg Ala Tyr Cys Leu Ser Leu Trp
        115                 120                 125

Cys Leu Leu Val Tyr Leu Met Ile Ser Leu Leu Leu Val Ala His Ile
    130                 135                 140

Gly Leu Lys Pro Tyr Asn Pro Ser Gln Gly Asn Ser Ser Ile Leu Tyr
145                 150                 155                 160

Pro Leu Lys Ser Trp His Tyr Leu Tyr Ile Val Lys Leu Asn Ala Gly
                165                 170                 175

Ser Gly Leu Pro Leu Met Val Phe Leu Val Ser Ser Gly Met Leu Ile
            180                 185                 190

Val Ser Leu Tyr Arg His His Lys Lys Met Glu Val His Thr Ala Gly
        195                 200                 205

Arg Arg Asp Ala Gln Ala Lys Ala His Ile Thr Val Leu Lys Ser Leu
    210                 215                 220

Gly Cys Phe Leu Ile Leu His Val Ile Tyr Ile Leu Ala Ser Pro Phe
225                 230                 235                 240

Ser Ile Thr Ser Lys Ser Ser Ala Asp Leu Leu Val Val Phe Ile Ser
                245                 250                 255

Glu Thr Val Met Ala Ala Tyr Pro Ser Leu His Ser Val Ile Leu Ile
            260                 265                 270

Leu Gly Asn Pro Arg Met Lys Gln Thr Cys Gln Arg Ile Leu Trp Lys
        275                 280                 285

Thr Val Cys Ala Trp Lys Ser
    290                 295


<210> SEQ ID NO 22
<211> LENGTH: 312
<212> TYPE: PRT
<213> ORGANISM: Canis familiaris

<400> SEQUENCE: 22

Met Pro Asp Lys Val Glu Ser Ile Leu Met Leu Val Ala Ala Gly Glu
1               5                   10                  15

Phe Ser Met Gly Ile Leu Gly Asn Thr Phe Ile Gly Leu Val Asn Cys
            20                  25                  30

Ile Gly Trp Ile Lys Lys Arg Lys Ile Ala Ser Ile Asp Leu Ile Leu
        35                  40                  45

Thr Ser Leu Ala Ile Ser Arg Ile Cys Leu Leu Cys Ile Ile Leu Leu
    50                  55                  60

Asp Cys Phe Ile Leu Val Leu Tyr Pro Asp Val Tyr Ala Thr Gly Lys
65                  70                  75                  80

Gln Met Arg Ile Ile Asp Phe Phe Trp Thr Leu Thr Asn His Leu Ser
                85                  90                  95

Val Trp Phe Ala Thr Cys Leu Ser Ile Phe Tyr Phe Leu Lys Ile Ala
            100                 105                 110

Asn Phe Phe His Pro Leu Phe Leu Trp Met Lys Trp Arg Ile Asp Ser
        115                 120                 125

Ala Ile Pro Arg Ile Leu Leu Gly Cys Leu Ala Leu Ser Val Phe Ile
    130                 135                 140

Ser Leu Val Val Thr Glu Asn Leu Asn Asp Asp Phe Arg Cys Cys Val
145                 150                 155                 160

Arg Thr Lys Lys Lys Thr Asn Leu Thr Val Arg Cys Arg Val Lys Lys
                165                 170                 175

Ala Lys Tyr Ser Ser Ile Lys Ile Cys Leu Asn Leu Leu Thr Leu Phe
            180                 185                 190
```

```
Pro Phe Ser Val Ser Leu Ile Ser Phe Leu Leu Leu Ile Leu Ser Leu
        195                 200                 205

Trp Arg His Thr Arg Gln Met Lys Phe Asn Ala Thr Gly Cys Arg Asp
    210                 215                 220

Phe Ser Ile Glu Ala His Met Gly Ala Met Lys Ala Val Ile Ser Phe
225                 230                 235                 240

Leu Leu Leu Phe Ile Ala Tyr Tyr Leu Ala Phe Leu Val Ala Thr Ser
                245                 250                 255

Ser Tyr Phe Met Pro Glu Thr Glu Leu Ala Val Ile Ile Gly Glu Leu
            260                 265                 270

Ile Ala Leu Ile Tyr Pro Ser Ser His Ser Phe Ile Leu Ile Leu Gly
        275                 280                 285

Ser Asn Lys Leu Arg Gln Ala Ser Leu Arg Val Leu Trp Lys Val Lys
    290                 295                 300

Tyr Val Leu Lys Arg Arg Asn Phe
305                 310


<210> SEQ ID NO 23
<211> LENGTH: 322
<212> TYPE: PRT
<213> ORGANISM: Canis familiaris

<400> SEQUENCE: 23

Met Leu Ser Ile Leu Glu Gly Leu Leu Ile Phe Ile Ala Val Ser Glu
1               5                   10                  15

Ser Ile Leu Gly Val Leu Gly Asn Gly Phe Ile Gly Leu Val Asn Cys
            20                  25                  30

Ile Asp Cys Val Lys Asn Lys Lys Phe Ser Met Val Gly Phe Ile Leu
        35                  40                  45

Thr Gly Leu Ala Thr Ser Arg Ile Cys Leu Ile Leu Ile Ile Ile Thr
    50                  55                  60

Asp Gly Phe Ile Lys Ile Phe Ser Pro Asp Met Tyr Ser Ser Gly Asn
65                  70                  75                  80

Leu Ile Asp Tyr Ile Ser Tyr Leu Trp Val Ile Ile Asn Gln Ser Ser
                85                  90                  95

Ile Trp Phe Ala Thr Ser Leu Ser Ile Phe Tyr Phe Leu Lys Ile Ala
            100                 105                 110

Asn Phe Ser His His Ile Phe Leu Trp Leu Lys Gly Arg Ile Asn Ser
        115                 120                 125

Val Leu Pro Leu Leu Met Gly Ser Leu Phe Ile Ser Trp Leu Phe Thr
    130                 135                 140

Phe Pro Gln Ile Val Lys Ile Ile Asn Asp Asn Arg Met Lys Ser Arg
145                 150                 155                 160

Asn Thr Thr Trp Gln Leu Asn Met Gln Lys Ser Glu Phe Phe Thr Lys
                165                 170                 175

Gln Ile Leu Leu Asn Leu Gly Val Ile Leu Leu Phe Thr Leu Cys Leu
            180                 185                 190

Ile Thr Cys Phe Leu Leu Ile Val Ser Leu Trp Arg His Asn Arg His
        195                 200                 205

Met Gln Leu Asn Val Thr Gly Leu Arg Asp Pro Ser Thr Glu Ala His
    210                 215                 220

Val Lys Ala Met Lys Ile Leu Val Ser Phe Ile Ile Leu Phe Ile Leu
225                 230                 235                 240

Tyr Phe Ile Gly Ile Ala Ile Glu Ile Ser Cys Phe Ile Leu Pro Glu
```

```
                245                 250                 255

Asn Lys Leu Leu Phe Ile Phe Gly Met Met Thr Thr Ala Ile Tyr Pro
            260                 265                 270

Trp Gly His Ser Phe Ile Leu Ile Leu Gly Asn Ser Lys Leu Lys Gln
        275                 280                 285

Ala Ser Leu Lys Thr Leu Gln Gln Leu Lys Cys Glu Ala Arg Arg Leu
    290                 295                 300

Leu Thr Ala Ala Gln Ile His Val Gly Gly Asn Gly Cys Ser Arg Arg
305                 310                 315                 320

Ile Ile


<210> SEQ ID NO 24
<211> LENGTH: 314
<212> TYPE: PRT
<213> ORGANISM: Canis familiaris

<400> SEQUENCE: 24

Met Ala Gly Thr Met Lys Asn Val Phe Met Met Ile Phe Ala Gly Glu
1               5                   10                  15

Phe Ile Ile Gly Ile Leu Gly Asn Gly Phe Ile Ile Leu Val Asn Cys
            20                  25                  30

Ile Asp Trp Ile Arg Ser Trp Lys Phe Phe Leu Ile Asp Phe Ile Leu
        35                  40                  45

Thr Cys Leu Ala Ile Ser Arg Ile Phe Leu Leu Cys Ile Ile Met Leu
    50                  55                  60

Gly Ile Gly Leu Asp Ile Ile Cys Lys Glu Ile Trp Tyr Asn Asp Asn
65                  70                  75                  80

Gln Leu Ile Thr Phe Glu Val Leu Trp Thr Gly Cys Asn Tyr Phe Cys
                85                  90                  95

Thr Ile Cys Thr Val Cys Leu Ser Val Phe Tyr Phe Leu Lys Ile Ala
            100                 105                 110

Asn Ser Ser Asn Pro Ile Phe Phe Trp Leu Lys Arg Arg Ile His Arg
        115                 120                 125

Leu Leu Leu Ile Ile Val Leu Gly Ala Val Phe Tyr Phe Cys Leu Ser
    130                 135                 140

Leu Leu Leu Lys Asp Ile Val Phe Lys Asn Met Ile Lys Thr Lys Val
145                 150                 155                 160

Asn Thr Glu Ser Asn Val Thr Leu Asn Phe Thr Ala Arg Lys Tyr Asp
                165                 170                 175

Leu Leu Thr Ser Asn Ile Phe Leu Asn Met Leu Phe Val Ile Pro Phe
            180                 185                 190

Ala Val Ser Leu Ala Ser Phe Val Leu Leu Ile His Ser Leu Trp Asn
        195                 200                 205

His Thr Arg Arg Met Lys Gly Ile Asp Ser Gly Asp Leu Ile Thr Glu
    210                 215                 220

Ala His Val Arg Ala Met Lys Phe Met Ile Ser Phe Leu Leu Phe Phe
225                 230                 235                 240

Phe Ile Tyr Tyr Leu Ser Asn Ile Ile Ile Tyr Phe Ala Tyr Val Val
                245                 250                 255

Leu Asp Ser Leu Val Ala Lys Ile Phe Ala Asn Ile Leu Val Phe Ser
            260                 265                 270

Tyr Pro Ser Gly His Pro Phe Leu Leu Ile Leu Trp Asn Cys Lys Leu
        275                 280                 285

Lys Gln Ala Ser Leu Tyr Val Leu Arg Lys Leu Lys Trp Cys Met Asn
```

-continued

```
    290                 295                 300

Leu Arg Lys Pro Ala Tyr Ile Lys His Thr
305                 310


<210> SEQ ID NO 25
<211> LENGTH: 334
<212> TYPE: PRT
<213> ORGANISM: Canis familiaris

<400> SEQUENCE: 25

Met Leu Ala Leu Thr Pro Val Ile Thr Val Ser Tyr Glu Val Lys Ser
1               5                   10                  15

Ala Phe Met Phe Leu Ser Val Leu Glu Leu Ala Val Gly Ile Leu Thr
            20                  25                  30

Asn Ala Phe Ile Phe Leu Val Asn Phe Trp Asp Val Val Arg Arg Gln
        35                  40                  45

Pro Leu Ser Asn Cys Asp Leu Ile Leu Leu Ser Leu Ser Leu Thr Arg
    50                  55                  60

Leu Phe Leu His Gly Leu Leu Phe Leu Asp Ala Ile Gln Leu Thr Tyr
65                  70                  75                  80

Phe Gln Arg Met Lys Asp Pro Leu Ser Leu Ser Tyr Gln Thr Ile Ile
                85                  90                  95

Met Leu Trp Met Ile Thr Asn Gln Ala Gly Leu Trp Leu Thr Thr Cys
            100                 105                 110

Leu Ser Leu Phe Tyr Cys Ser Lys Ile Val Arg Phe Ser His Thr Leu
        115                 120                 125

Leu Leu Cys Leu Ala Asn Trp Val Ser Arg Lys Ala Pro Gln Met Leu
    130                 135                 140

Leu Gly Ala Met Leu Phe Ser Ser Ala Cys Thr Leu Leu Cys Leu Gly
145                 150                 155                 160

Asp Phe Phe Ser Arg Ser Gly Phe Ala Phe Thr Thr Val Leu Leu Met
                165                 170                 175

Asn Asn Thr Glu Phe Asn Ser Gln Ile Val Lys Leu Asn Phe Tyr Tyr
            180                 185                 190

Ser Ser Ile Phe Cys Thr Leu Gly Ser Ile Pro Pro Phe Met Phe Phe
        195                 200                 205

Leu Val Ser Ser Gly Val Leu Ile Ile Ser Leu Gly Arg His Met Arg
    210                 215                 220

Thr Met Lys Ala Asn Thr Lys Asp Ser Gly Asp Pro Ser Leu Glu Ala
225                 230                 235                 240

His Ile Lys Ala Leu Ile Ser Leu Ile Ser Phe Leu Cys Leu Tyr Val
                245                 250                 255

Val Ser Phe Cys Val Ala Leu Ile Ser Val Pro Leu Thr Met Val Trp
            260                 265                 270

His Asn Lys Ile Gly Val Met Ile Cys Val Gly Ile Leu Ala Ala Cys
        275                 280                 285

Pro Ser Ile His Ala Ala Ile Leu Ile Ser Gly Asn Ala Lys Leu Arg
    290                 295                 300

Arg Ala Val Glu Thr Ile Leu Leu Trp Val Gln Ser Ser Leu Lys Val
305                 310                 315                 320

Arg Ala Gly His Arg Ala Asp Leu Arg Thr Pro Asp Leu Cys
                325                 330


<210> SEQ ID NO 26
<211> LENGTH: 321
```

<212> TYPE: PRT
<213> ORGANISM: Canis familiaris

<400> SEQUENCE: 26

```
Met Met Glu Thr Cys Asn Pro Pro Glu Asn Glu Leu Ser Pro Phe Gly
1               5                   10                  15

Ile Leu Ser Ile Leu Thr Ile Thr Gly Thr Glu Cys Ile Val Gly Ile
            20                  25                  30

Ile Ala Asn Gly Phe Ile Met Ala Ile Asn Ala Ala Glu Trp Ile Lys
        35                  40                  45

Asn Lys Thr Val Ser Thr Ser Gly Arg Val Leu Phe Phe Leu Ser Ala
    50                  55                  60

Ser Arg Ile Ala Leu Gln Ser Phe Thr Met Leu Glu Ile Thr Phe Ser
65                  70                  75                  80

Ser Thr Ser Pro Arg Phe Tyr Asn Glu Asp Val Met Tyr Asp Thr Phe
                85                  90                  95

Lys Val Ser Phe Met Phe Leu Asn His Cys Ser Leu Trp Phe Ala Ala
            100                 105                 110

Trp Leu Ser Phe Phe Tyr Phe Val Lys Ile Ala Asp Phe Ser His Pro
        115                 120                 125

Leu Phe Leu Lys Leu Lys Trp Arg Ile Ser Arg Leu Met Pro Trp Leu
    130                 135                 140

Leu Trp Leu Ser Val Leu Ile Ser Leu Gly Tyr Ser Met Leu Leu Ser
145                 150                 155                 160

Asn Asp Ile Tyr Thr Val Tyr Cys Asn Asn Ser Ser Ile Pro Ser Ser
                165                 170                 175

Asn Ser Thr Lys Lys Lys Tyr Phe Thr Lys Thr Asn Val Val Asn Leu
            180                 185                 190

Val Leu Leu Tyr Asn Leu Gly Ile Phe Ile Pro Leu Ile Met Phe Ile
        195                 200                 205

Leu Ser Ala Thr Leu Leu Ile Ile Ser Leu Lys Arg His Thr Leu His
    210                 215                 220

Met Glu Ser Asn Ala Thr Gly Cys Arg Asp Pro Ser Met Glu Ala His
225                 230                 235                 240

Ile Gly Ala Ile Arg Ala Thr Ser Tyr Phe Leu Ile Leu Tyr Ile Phe
                245                 250                 255

Asn Ser Val Ala Leu Phe Leu Tyr Met Ser Asn Ile Phe Asp Ile Asn
            260                 265                 270

Ser Ser Trp Asn Ile Leu Cys Lys Phe Ile Met Ala Ala Tyr Pro Ala
        275                 280                 285

Gly His Ser Ile Leu Leu Ile Gln Asp Asn Pro Gly Leu Arg Arg Ala
    290                 295                 300

Trp Lys Arg Leu Gln Pro Gln Val His Phe Tyr Leu Lys Glu Gln Thr
305                 310                 315                 320

Pro
```

<210> SEQ ID NO 27
<211> LENGTH: 318
<212> TYPE: PRT
<213> ORGANISM: Canis familiaris

<400> SEQUENCE: 27

```
Met Ala Thr Val Ser Thr Asp Ala Thr Asp Arg Asp Met Ser Arg Phe
1               5                   10                  15

Lys Ile Val Leu Thr Leu Val Val Pro Gly Ile Glu Cys Leu Thr Gly
```

```
            20                  25                  30

Ile Val Gly Asn Gly Phe Ile Thr Ile Ile His Gly Ala Lys Trp Ala
        35                  40                  45

Arg Gly Lys Arg Leu Pro Val Thr Asp Cys Ile Leu Leu Met Leu Ser
    50                  55                  60

Phe Ser Arg Leu Leu Leu Gln Ile Trp Met Met Leu Glu Asn Ile Tyr
65                  70                  75                  80

Ser Leu Leu Phe Arg Val Thr Tyr Asn Gln Ser Thr Val Phe Ile Val
                85                  90                  95

Phe Lys Val Thr Val Ile Phe Leu Asn Tyr Phe Asn Leu Trp Leu Ala
            100                 105                 110

Ala Trp Leu Asn Ile Phe Tyr Cys Leu Arg Ile Thr Asn Leu Ala His
        115                 120                 125

His Val Phe Phe Met Met Lys Arg Lys Ile Thr Glu Leu Met Pro Arg
    130                 135                 140

Leu Leu Gly Leu Ser Leu Phe Ile Ser Leu Cys Phe Ser Phe Pro Phe
145                 150                 155                 160

Ser Thr Asp Ile Phe His Val Tyr Val Asn Ser Ser Ile Pro Ile Arg
                165                 170                 175

Ser Ser Asn Thr Thr Glu Lys Lys Tyr Phe Ser Glu Thr Asn Val Val
            180                 185                 190

Asn Leu Val Leu Leu Tyr Asn Leu Gly Ile Phe Ile Pro Leu Ile Met
        195                 200                 205

Phe Ile Leu Ser Ala Thr Leu Leu Ile Ile Ser Leu Lys Arg His Thr
    210                 215                 220

Leu His Met Glu Ser Asn Ala Thr Gly Cys Arg Asp Pro Ser Met Glu
225                 230                 235                 240

Ala His Phe Gly Ala Ile Arg Ala Thr Ser Tyr Phe Leu Ile Leu Tyr
                245                 250                 255

Ile Phe Asn Ala Val Ala Leu Phe Leu Ser Met Ser Asn Ile Phe Asp
            260                 265                 270

Ile Asn Ser Ser Trp Asn Ile Leu Cys Lys Ile Val Met Ala Ala Tyr
        275                 280                 285

Pro Ala Ser His Ser Val Leu Leu Ile Leu Gly Asn Pro Gly Leu Arg
    290                 295                 300

Arg Ala Trp Lys Arg Phe Gln His His Val Pro Leu His Leu
305                 310                 315


<210> SEQ ID NO 28
<211> LENGTH: 308
<212> TYPE: PRT
<213> ORGANISM: Canis familiaris

<400> SEQUENCE: 28

Met Gln Pro Ala Val Ser Ala Phe Phe Met Leu Leu Phe Val Leu Leu
1               5                   10                  15

Cys Val Leu Gly Ile Leu Ala Asn Gly Phe Ile Val Leu Val Leu Ser
            20                  25                  30

Arg Glu Arg Met Arg Arg Gly Arg Leu Leu Pro Ser Asp Val Ile Leu
        35                  40                  45

Leu Ser Leu Gly Ala Ser Arg Phe Cys Leu Gln Cys Ile Gly Met Met
    50                  55                  60

Asn Asn Phe Tyr Tyr Tyr Leu His Leu Glu Glu Tyr Ser Thr Gly Pro
65                  70                  75                  80
```

-continued

```
Ala Arg Gln Phe Phe Gly Leu His Trp Asp Phe Leu Asn Ser Ala Thr
                85                  90                  95

Phe Trp Phe Gly Ser Trp Leu Ser Val Leu Phe Cys Met Lys Ile Ala
            100                 105                 110

Ser Phe Thr His Pro Thr Phe Leu Trp Leu Arg Trp Arg Leu Pro Gly
        115                 120                 125

Ser Val Pro Trp Leu Leu Gly Ala Ser Leu Leu Ile Ser Phe Leu Val
    130                 135                 140

Thr Leu Leu Phe Phe Trp Gly Asn His Ala Val Tyr Gln Gly Phe Leu
145                 150                 155                 160

Ile Arg Lys Tyr Pro Gly Asn Met Thr Phe Gln Gln Trp Ser Arg Arg
                165                 170                 175

Leu Glu Ile His Tyr Phe Leu Pro Leu Lys Phe Ile Thr Leu Ser Val
            180                 185                 190

Pro Cys Ser Val Phe Leu Val Ser Ile Ala Leu Leu Ile Asn Ser Leu
        195                 200                 205

Arg Arg His Arg Gly Arg Met Arg Arg Ser Gly His Gly Leu Gln Asp
    210                 215                 220

Pro Ser Ser Gln Ala His Thr Arg Ala Leu Lys Ser Leu Val Ser Phe
225                 230                 235                 240

Leu Ile Leu Tyr Ala Leu Ser Phe Ala Ser Leu Val Ile Asp Ala Ala
                245                 250                 255

Gly Phe Phe Cys Ser Gln Ser Asp Trp Tyr Trp Pro Trp Gln Ile Leu
            260                 265                 270

Ile Tyr Leu Cys Thr Ser Val His Pro Tyr Ile Leu Ile Leu Ser Asn
        275                 280                 285

Leu Arg Leu Arg Gly Gly Cys Arg Gln Leu Leu Leu Leu Val Arg Gly
    290                 295                 300

Ser Gln Leu Ala
305
```

<210> SEQ ID NO 29
<211> LENGTH: 323
<212> TYPE: PRT
<213> ORGANISM: Canis familiaris

<400> SEQUENCE: 29

```
Met Leu Ala Gly Leu Asp Ile Ile Phe Leu Thr Leu Ser Thr Ala Glu
1               5                   10                  15

Phe Ile Ile Gly Met Leu Gly Asn Ala Phe Ile Gly Leu Val Asn Cys
            20                  25                  30

Ser Glu Trp Val Lys Asn Arg Lys Ile Ser Leu Ala Asp Phe Ile Leu
        35                  40                  45

Ile Cys Leu Ala Ile Ser Arg Ile Ala Gln Leu Leu Val Ser Trp Phe
    50                  55                  60

Glu Ser Phe Met Met Gly Leu Ser Pro Leu Phe Phe Ser Thr Tyr Lys
65                  70                  75                  80

Leu Ala Lys Ser Ile Thr Leu Leu Trp Arg Ile Thr His His Leu Ala
                85                  90                  95

Thr Trp Phe Ser Thr Cys Leu Ser Ile Phe Tyr Leu Leu Lys Ile Ala
            100                 105                 110

Gln Phe Ser His Ser Leu Phe Leu Trp Leu Arg Trp Arg Met Asn Arg
        115                 120                 125

Val Val Leu Ala Ile Leu Val Phe Ser Leu Phe Phe Leu Leu Phe Asp
    130                 135                 140
```

```
Phe Leu Met Leu Glu Thr Phe Asn Asp Leu Phe Ser Asn Val Asp Ala
145                 150                 155                 160

Met Asp Glu Ser Asn Leu Thr Leu Tyr Ile Tyr Glu Ser Lys Thr Phe
                165                 170                 175

Tyr Val Lys Thr Leu Ile Leu Leu Ser Phe Ser Tyr Ile Ile Pro Ile
            180                 185                 190

Ile Leu Ser Leu Thr Ser Leu Leu Leu Leu Phe Leu Ser Leu Val Lys
        195                 200                 205

His Ile Arg Asn Leu Gln Leu Asn Ser Met Gly Ser Arg Asp Ser Ser
    210                 215                 220

Thr Gln Ala His Lys Lys Ala Ile Lys Met Val Met Ser Phe Leu Phe
225                 230                 235                 240

Leu Phe Thr Val His Phe Phe Ser Ile Gln Leu Ser Asn Trp Met Phe
                245                 250                 255

Phe Leu Phe Trp Asn Lys Lys Ile Thr Lys Phe Ile Met Leu Ala Val
            260                 265                 270

Tyr Val Phe Pro Ser Ser His Ser Leu Ile Leu Ile Leu Gly Asn Ser
        275                 280                 285

Lys Leu Arg Gln Thr Ala Leu Lys Val Leu Trp His Leu Lys Ser Ser
    290                 295                 300

Leu Lys Arg Glu Lys Pro Asn Ser Ser Leu Pro Ile Asp Phe Pro Glu
305                 310                 315                 320

Ser Phe Gln


<210> SEQ ID NO 30
<211> LENGTH: 349
<212> TYPE: PRT
<213> ORGANISM: Canis familiaris

<400> SEQUENCE: 30

Met Leu Pro Leu Leu Gln Ser Ile Phe Ser Ile Leu Val Met Thr Glu
1               5                   10                  15

Phe Val Leu Gly Asn Phe Ala Asn Gly Phe Ile Val Leu Val Asn Tyr
            20                  25                  30

Ile Ala Trp Val Lys Arg Gln Lys Ile Ser Ser Ala Asp Gln Ile Leu
        35                  40                  45

Thr Gly Leu Ala Val Ser Arg Ile Gly Leu Leu Trp Val Ile Leu Ile
    50                  55                  60

Asn Trp Tyr Ala Thr Leu Leu Asn Pro Ala Leu Tyr Ser Leu Glu Val
65                  70                  75                  80

Arg Leu Leu Val His Ile Ala Trp Thr Ala Asn Asn His Phe Ser Ile
                85                  90                  95

Trp Leu Ala Thr Ser Leu Ser Val Phe Tyr Leu Phe Lys Ile Ala Asn
            100                 105                 110

Phe Ser Asn Leu Ile Phe Leu Arg Leu Lys Trp Arg Val Lys Ser Val
        115                 120                 125

Val Phe Val Met Leu Leu Gly Ser Leu Phe Phe Leu Val Phe His Val
    130                 135                 140

Ala Val Val Ser Ile Tyr Glu Gln Met Gln Met Lys Glu Tyr Glu Gly
145                 150                 155                 160

Asn Ile Thr Arg Gln Thr Lys Leu Arg Asp Ile Ala Gln Leu Met Asn
                165                 170                 175

Met Thr Val Phe Thr Leu Met Asn Phe Val Pro Phe Ala Ile Ser Leu
            180                 185                 190
```

```
Thr Ser Phe Leu Leu Leu Ile Phe Ser Leu Trp Lys His Leu Lys Lys
        195                 200                 205

Met Arg Ser Gly Gly Lys Arg Tyr Gln Asp Ser Ser Thr Lys Val His
    210                 215                 220

Ile Lys Ala Met Gln Thr Val Ile Ser Phe Leu Leu Leu Leu Val Cys
225                 230                 235                 240

Tyr Phe Leu Thr Leu Ile Ala Ile Val Trp Ser Ser Asn Arg Leu Gln
                245                 250                 255

Asn Lys Leu Ile Phe Leu Leu Cys Lys Ala Ile Gly Ile Leu Tyr Pro
            260                 265                 270

Ser Ser His Ser Phe Ile Leu Ile Trp Gly Asn Lys Lys Leu Arg Glu
        275                 280                 285

Asp Phe Leu Ser Phe Leu Trp Gln Leu Lys Gly Trp Leu Lys Lys Gly
    290                 295                 300

Tyr Lys Arg Ser Ile Met Cys Leu Leu Gly Glu Asn Lys Leu Met Glu
305                 310                 315                 320

Ser Val Ile Phe Phe Ser Ser Thr Ser Phe Ser Asn Glu Tyr Val Ile
                325                 330                 335

Glu Gln Phe Pro Lys Ile Tyr Leu Lys Lys Ser Phe Leu
            340                 345


<210> SEQ ID NO 31
<211> LENGTH: 301
<212> TYPE: PRT
<213> ORGANISM: Canis familiaris

<400> SEQUENCE: 31

Met Ser Ser Ser Pro Thr Leu Ile Phe Met Val Ile Phe Phe Leu Glu
1               5                   10                  15

Ser Leu Ala Ala Met Leu Gln Asn Gly Phe Met Val Thr Val Leu Gly
            20                  25                  30

Arg Glu Trp Val Arg Arg Arg Thr Leu Pro Ala Gly Asp Met Ile Val
        35                  40                  45

Ala Ser Leu Ala Ala Ser Trp Phe Cys Leu His Gly Val Ala Ile Leu
    50                  55                  60

Asn Asn Leu Leu Ile Phe Phe Gly Phe His Phe Val Arg Asp Tyr Tyr
65                  70                  75                  80

Asn Thr Leu Trp His Phe Val Asn Thr Leu Thr Leu Trp Leu Thr Ala
                85                  90                  95

Trp Leu Ala Val Phe Tyr Cys Val Lys Val Ala Val Phe Ser His Pro
            100                 105                 110

Val Phe Phe Trp Leu Lys Trp Arg Ile Ser Arg Leu Val Pro Arg Leu
        115                 120                 125

Leu Leu Gly Ser Leu Val Leu Val Gly Leu Thr Val Ile Ser Ser Ala
    130                 135                 140

Ile Val Thr Gly Ile Leu Lys Gln Met Ile Ala Ser Lys Ser Ser Gln
145                 150                 155                 160

Gly Asn Ser Thr Trp Ala Glu Arg Val Gln Ala Phe Tyr Arg Ser Phe
                165                 170                 175

His Leu Phe Asp Val Met Leu Met Trp Ser Val Pro Phe Leu Leu Phe
            180                 185                 190

Leu Val Ser Met Leu Leu Leu Val Phe Ser Leu Cys Arg His Leu Gly
        195                 200                 205

Leu Met Arg Asn Tyr Arg Gln Asp Pro Cys Asp Pro Ser Thr Arg Val
```

```
    210                 215                 220

His Thr Met Ala Leu Lys Ser Leu Val Phe Phe Leu Val Phe Tyr Thr
225                 230                 235                 240

Pro Tyr Phe Leu Ser Leu Val Val Val Ala Ile Glu Ile Thr Asn Phe
                245                 250                 255

Gln Ser His Trp Tyr Trp Ala Trp Glu Val Val Thr Tyr Ala Ser Ile
            260                 265                 270

Cys Leu His Ser Ser Met Leu Val Leu Ser Ser Pro Lys Leu Arg Lys
        275                 280                 285

Val Leu Met Thr Arg Leu Trp Lys Ala Leu Asp Lys Gly
    290                 295                 300


<210> SEQ ID NO 32
<211> LENGTH: 312
<212> TYPE: PRT
<213> ORGANISM: Canis familiaris

<400> SEQUENCE: 32

Met Pro Ser Arg Ile Glu Asn Ala Phe Leu Val Ala Ala Ala Gly Glu
1               5                   10                  15

Leu Ile Thr Gly Met Leu Gly Asn Gly Phe Ile Val Leu Val Asn Cys
            20                  25                  30

Ile Asp Leu Val Lys Asn Leu Lys Leu Ser Thr Ala Asp Cys Ile Leu
        35                  40                  45

Thr Ser Leu Ala Leu Ser Arg Ile Ile Leu Leu Cys Ile Ile Leu Leu
    50                  55                  60

Asp Ser Leu Leu Met Val Phe Trp Gln His Leu Tyr Ala Ile Asp Lys
65                  70                  75                  80

Leu Ala Lys Phe Ile Ser Val Phe Trp Thr Leu Ser Asn His Leu Thr
                85                  90                  95

Thr Trp Ile Val Thr Cys Leu Asn Val Phe Tyr Phe Phe Lys Ile Ala
            100                 105                 110

Asn Phe Ser His Pro Cys Phe Thr Trp Leu Arg Trp Arg Ile Ser Arg
        115                 120                 125

Val Leu Leu Val Leu Pro Leu Gly Ser Leu Phe Leu Leu Phe Phe Asn
    130                 135                 140

Phe Glu Leu Leu Asp Thr Phe Thr Asn Phe Trp Val Asn Leu Tyr Gln
145                 150                 155                 160

Arg His Glu Arg Asn Ser Ile Trp Ser Leu Asp Val Ser Lys Thr Leu
                165                 170                 175

Tyr Leu Asn Ser Leu Ile Val Phe Ser Phe Ile Tyr Leu Ile Pro Phe
            180                 185                 190

Leu Leu Ser Leu Ala Ser Leu Leu Leu Leu Phe Leu Ser Leu Met Arg
        195                 200                 205

His Ile Arg Asn Val Gln Arg Asn Ser Ser Ser Arg Asp Phe Arg Thr
    210                 215                 220

Glu Ala His Lys Arg Ala Met Lys Met Val Met Ser Ser Leu Phe Leu
225                 230                 235                 240

Ser Met Val Asn Phe Thr Ser Ile Leu Leu Thr Gly Trp Phe Ser Leu
                245                 250                 255

Leu Leu Gln Asn His Gln Ala Asn Leu Ala Val Leu Leu Leu Ser Thr
            260                 265                 270

Leu Val Pro Ser Gly His Ser Phe Ile Leu Ile Leu Gly Asn Asn Lys
        275                 280                 285
```

-continued

```
Leu Arg Gln Ala Ala Leu Gly Leu Leu Trp His Leu Asn Cys His Leu
    290                 295                 300

Lys Met Val Lys Pro Phe Ala Ser
305                 310
```

SCREENING METHODS USING CANINE T2R RECEPTORS AND PET FOOD PRODUCTS AND COMPOSITIONS IDENTIFIED USING THE SAME

CROSS-REFERENCE TO RELATED APPLICATION

This application is a Continuation of U.S. patent application Ser. No. 16/885,102, filed on May 27, 2020, which is a Continuation of U.S. patent application Ser. No. 15/746,658, filed on Jan. 22, 2018, which claims priority to International Patent Application No. PCT/US2016/044540, filed on Jul. 28, 2016, which claims priority to U.S. Provisional Application Ser. No. 62/197,983, filed on Jul. 28, 2015, the content of each of which is incorporated by reference in its entirety, and to each of which priority is claimed.

SEQUENCE LISTING

The instant application contains a Sequence Listing which has been submitted electronically in ASCII format and is hereby incorporated by reference in its entirety. Said ASCII copy, created on Jan. 5, 2022, is named 0692690520SL.txt and is 65,790 bytes in size.

FIELD

The presently disclosed subject matter relates to the use of canine T2R bitter taste receptors (cT2Rs) for the identification of T2R modulators. The presently disclosed subject matter further relates to the use of canine T2R bitter taste receptors to screen raw materials for making pet food products, as well as screening finished pet food products, for the presence of T2R modulating compounds.

BACKGROUND

Taste profiles for edible compositions include basic tastes such as sweet, salt, bitter, sour, umami and kokumi. Taste profiles have also been described as including free fatty acid tastes. Chemical compounds that elicit these tastes are often referred to as tastants. Without being bound by theory, it is hypothesized that tastants are sensed by taste receptors in the mouth and throat which transmit signals to the brain where the tastants and resulting taste profiles are registered. Taste receptors include the T2R family of receptors, which comprise a G-protein coupled receptors (GPCR) family that detects compounds associated with bitter taste sensory perception.

Pet food manufacturers have a long-standing desire to provide pet food products that have high nutritional value. In addition, and with particular regard to cat and dog foods, pet food manufacturers desire a high degree of palatability so that pets can receive the full nutritional benefit from their food. Domestic animals are notoriously finicky in their food preferences, and often refuse to eat a pet food product that it has accepted over time or refuse to eat any more than a minimal amount of a pet food product. This phenomenon may be, in part, due to the subtle differences in the sensory profiles of the raw material, which can be perceived by the domestic animals because of their gustatory and olfactory systems. As a result, pet owners frequently change types and brands of pet food in order to maintain their pets in a healthy and contented condition.

While there have been recent advances in taste and flavor technologies, there remains a need for methods of screening raw materials that are used to make pet food product, and for screening finished pet food products, to ensure that the most palatable products and processes for making the pet food products are used. There also remains a need for compounds that can enhance or modify the palatability of pet food products by enhancing or modifying the taste, texture and/or flavor profiles of the pet food products. The enhancement or modification can be used to increase the intensity of a desirable attribute, to replace a desirable attribute that is not present or somehow lost in the pet food product, or to decrease the intensity of an undesirable attribute. In particular, it is desirable to decrease the presence or intensity of an undesirable bitter tastant in a pet food product. Similarly, there is a need to increase the acceptance of pet medications by enhancing or modifying the palatability of the medications.

The pet care industry is also concerned with developing taste deterrents that can effectively discourage a pet from chewing, licking, or ingesting things that are harmful to the health of the animal. While it is known that bitter taste can be effective to deter pets, there is a significant variation in pets' reactions to these bitter taste deterrents. Thus, there exists a need for compounds that effectively impart an undesirable bitter taste to harmful or toxic objects.

Therefore, there remains a need in the art for methods to screen raw pet food materials (e.g. new protein sources), as well as final pet food products, to provide palatable and nutritious pet food. There also remains a need to identify compounds that enhance, decrease, or otherwise modulate the palatability and/or bitter taste of pet food products, or objects, and for flavor compositions comprising these compounds.

SUMMARY OF THE INVENTION

The presently disclosed subject matter provides methods for identifying compounds that enhance, increase, decrease and/or modulate the activity and/or expression of a bitter taste receptor. In certain embodiments, the methods entail screening for compounds that modulate the bitter receptor activity and/or expression in a pet food product or medicine, or in raw materials used to make the pet food product or medicine. The presently disclosed subject matter also provides compounds that enhance, increase, decrease and/or modulate the activity and/or expression of a bitter taste receptor identified by said methods. In certain embodiments, the bitter taste receptor is a T2R receptor. In other embodiments, the bitter taste receptor is a canine T2R receptor.

In certain embodiments, the method for identifying compounds that enhance, increase, decrease and/or modulate the activity and/or expression of a bitter taste receptor comprises expressing a bitter taste receptor having a nucleotide sequence set forth in any one or more of SEQ ID NOs: 1-16, or a fragment or variant thereof, in a cell. The method can further comprise contacting the cell expressing the bitter taste receptor with a sample (e.g., pet food raw material, finished pet food, or a test compound) and determining the activity and/or expression of the bitter taste receptor in the presence of the sample as compared to the activity and/or expression of the receptor in the absence of the sample. In certain embodiments, the activity and/or expression of the bitter receptor is determined in the presence of the sample and a bitter receptor agonist.

In certain embodiments, a method for identifying compounds that enhance, increase, decrease and/or modulate the activity and/or expression of a bitter taste receptor comprises expressing a bitter taste receptor having an amino acid sequence set forth in any one or more of SEQ ID NOs: 17-32, or a fragment or variant thereof, in a cell. The method can further comprise contacting the cell expressing the bitter taste receptor with a sample (e.g., pet food raw material, finished pet food, or a test compound) and determining the activity and/or expression of the bitter taste receptor in the presence of the sample as compared to the activity and/or expression of the receptor in the absence of the sample. In certain embodiments, the activity and/or expression of the bitter receptor is determined in the presence of the sample and a bitter receptor agonist.

In certain embodiments, the present disclosure provides a method for identifying a composition that modulates the activity of a bitter taste receptor comprising (a) contacting a bitter taste receptor agonist with a bitter taste receptor, (b) determining the activity of the bitter taste receptor, (c) contacting a test agent with the bitter taste receptor, (d) determining the activity of the bitter taste receptor, and (e) selecting the test agent as the composition when the activity of (d) is greater than or less than the activity of (b).

In certain non-limiting embodiments, the methods for identifying a compound that modulates the activity of a bitter taste receptor described herein utilize cells expressing a bitter receptor that is native to the cells. Examples of such cells expressing a native bitter receptor include, for example but not limited to, dog and/or cat taste cells (e.g., primary taste receptor cells). In certain embodiments, the dog and/or cat taste cells expressing a bitter receptor are isolated from a dog and/or cat and cultured in vitro. In certain embodiments, the taste receptor cells can be immortalized, for example, such that the cells isolated from a dog and/or cat can be propagated in culture.

The present disclosure also provides for methods for identifying compounds that enhance, increase, decrease and/or modulate the activity and/or expression of a bitter taste receptor, wherein the assay is conducted using a cell-free assay, for example, wherein the bitter taste receptor is bound to or otherwise attached to a substrate.

The present disclosure also provides for methods for identifying compounds that enhance, increase, decrease and/or modulate the activity and/or expression of a bitter taste receptor, wherein the assay is conducted using an in silico model of the bitter taste receptor, for example, wherein the bitter taste receptor is modeled using a computer program and binding of the compound to the receptor is predicted through docking algorithms.

The presently disclosed subject matter further provides a method for making a palatable pet food product, wherein the raw materials used to generate the pet food product are screened to determine if they contain compounds that enhance, increase, decrease and/or modulate the activity and/or expression of a bitter taste receptor. In certain embodiments, the raw material is a novel protein source. In certain embodiments the raw material is a protein source that is not commonly consumed in the human food chain. In certain embodiments, a raw pet food product that comprises a compound that increases the activity and/or expression of a bitter taste receptor (for example, as compared to a bitter taste receptor not contacted with the raw material) is not selected for use in generating a finished pet food product. In other embodiments, a raw pet food material that does not increase the activity and/or expression of a bitter taste receptor (or that reduces the activity of a bitter taste receptor, for example, in the presence of a bitter receptor agonist) is selected for generating a finished pet food product.

The presently disclosed subject matter further provides a method for making a palatable pet food product, wherein the finished pet food product is screened to determine if it contains compounds that enhance, increase, decrease and/or modulate the activity and/or expression of a bitter taste receptor. In certain embodiments, the compounds are formed during the manufacturing process. In one embodiment, a finished pet food product that comprises a compound that increases the activity and/or expression of a bitter taste receptor (for example, as compared to a bitter taste receptor not contacted with the finished pet food product) is supplemented with one or more compounds that decrease the activity and/or expression of a bitter taste receptor (for example, an antagonist compound).

The presently disclosed subject matter further provides a method for making a palatable pet medicine product, wherein the finished pet medicine product is screened to determine if it contains compounds that enhance, increase, decrease and/or modulate the activity and/or expression of a bitter taste receptor. In certain embodiments, the compounds are formed during the manufacturing process. In one embodiment, a finished pet medicine product that comprises a compound that increases the activity and/or expression of a bitter taste receptor (for example, as compared to a bitter taste receptor not contacted with the finished pet medicine product) is supplemented with one or more compounds that decrease the activity and/or expression of a bitter taste receptor (for example, an antagonist compound).

The presently disclosed subject matter further provides flavor compositions that comprise a modulator of a bitter taste receptor, e.g., an agonist and/or an antagonist and/or an allosteric modulator and/or an inverse agonist, identified according to the methods described herein.

In certain embodiments, said compounds can be used in methods for maintaining the health of an animal by imparting a bitter taste and/or decreasing the palatability of an object or surface. In certain embodiments, the method comprises applying a taste deterrent product comprising a compound as described herein to the object or surface. In certain embodiments, the object is harmful to the health of the animal or toxic to the animal.

The foregoing has outlined rather broadly the features and technical advantages of the present application in order that the detailed description that follows may be better understood. Additional features and advantages of the application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

BRIEF DESCRIPTION OF THE DRAWINGS

FIGS. 1A-1P show canine bitter taste receptor (T2R) nucleotide sequences (SEQ ID NOs: 1-16) along with their corresponding amino acid sequences (SEQ ID NOs: 17-32). The sequences include the canine bitter taste receptors cT2R1 (FIG. 1A), cT2R2 (FIG. 1B), cT2R3 (FIG. 1C), cT2R4 (FIG. 1D), cT2R5 (FIG. 1E), cT2R7 (FIG. 1F), cT2R10 (FIG. 1G), cT2R12 (FIG. 1H), cT2R38 (FIG. 1I), cT2R39 (FIG. 1J), cT2R40 (FIG. 1K), cT2R41 (FIG. 1L), cT2R42 (FIG. 1M), cT3R43 (FIG. 1N), cT2R62 (FIG. 1O), and cT2R67 (FIG. 1P).

Figure 2A:
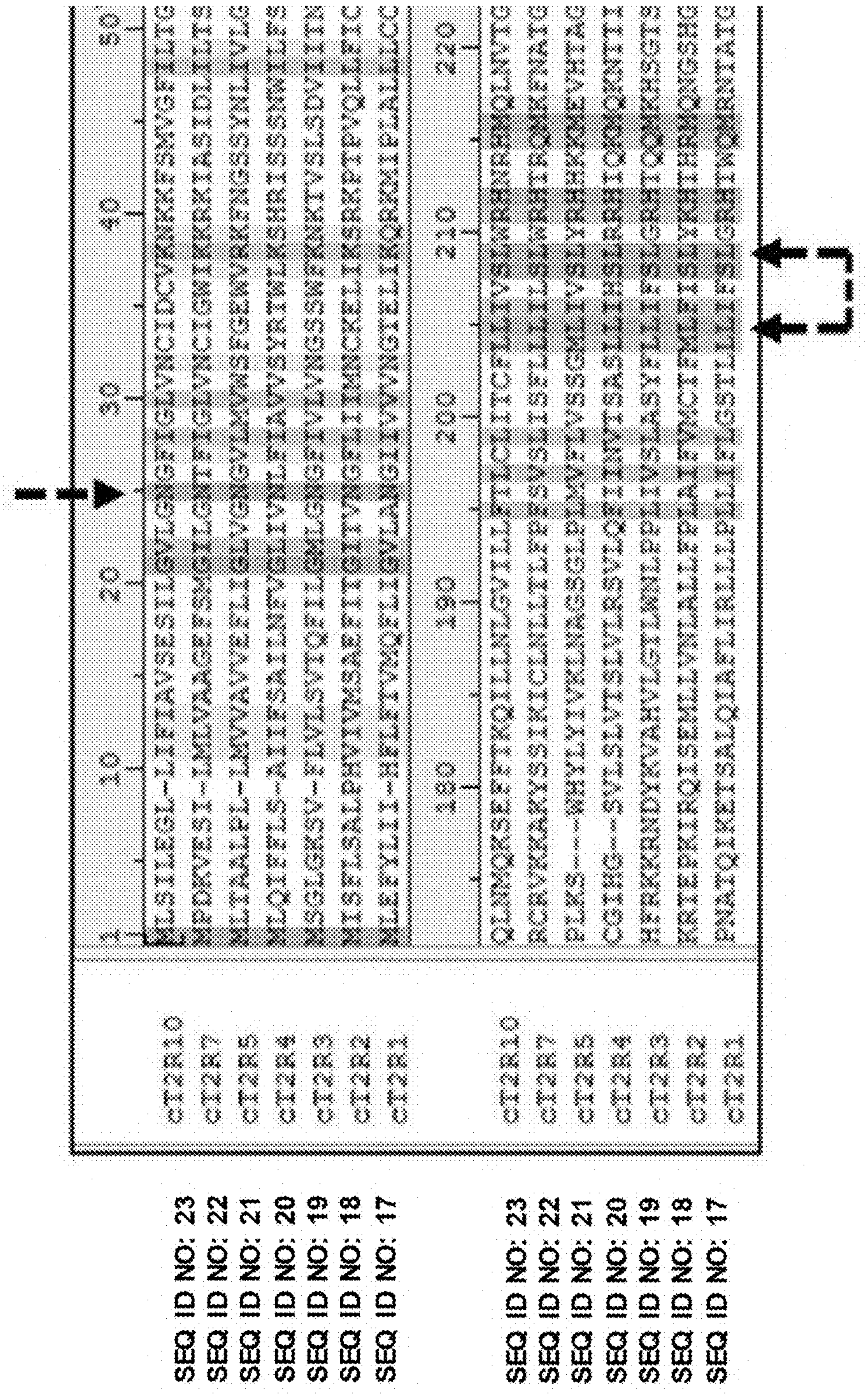
FIGS. 2A-2C show canine T2R sequence alignments. The dashed grey arrows indicate active site positions occupied by mostly asparagine or serine residues. The solid black arrows indicate structural tryptophan residues that are present in all human and cat bitter receptors as well as all canine bitter receptors except T2R12. The dashed black arrows indicate the conserved asparagine which is present in most of the bitter receptors. The conjoined solid arrows indicate the conserved LxxxR motif (IxxxR for some instances in T2R2), wherein x can be any amino acid. The conjoined dashed arrows indicate the conserved LxxSL motif
Figure 2A:
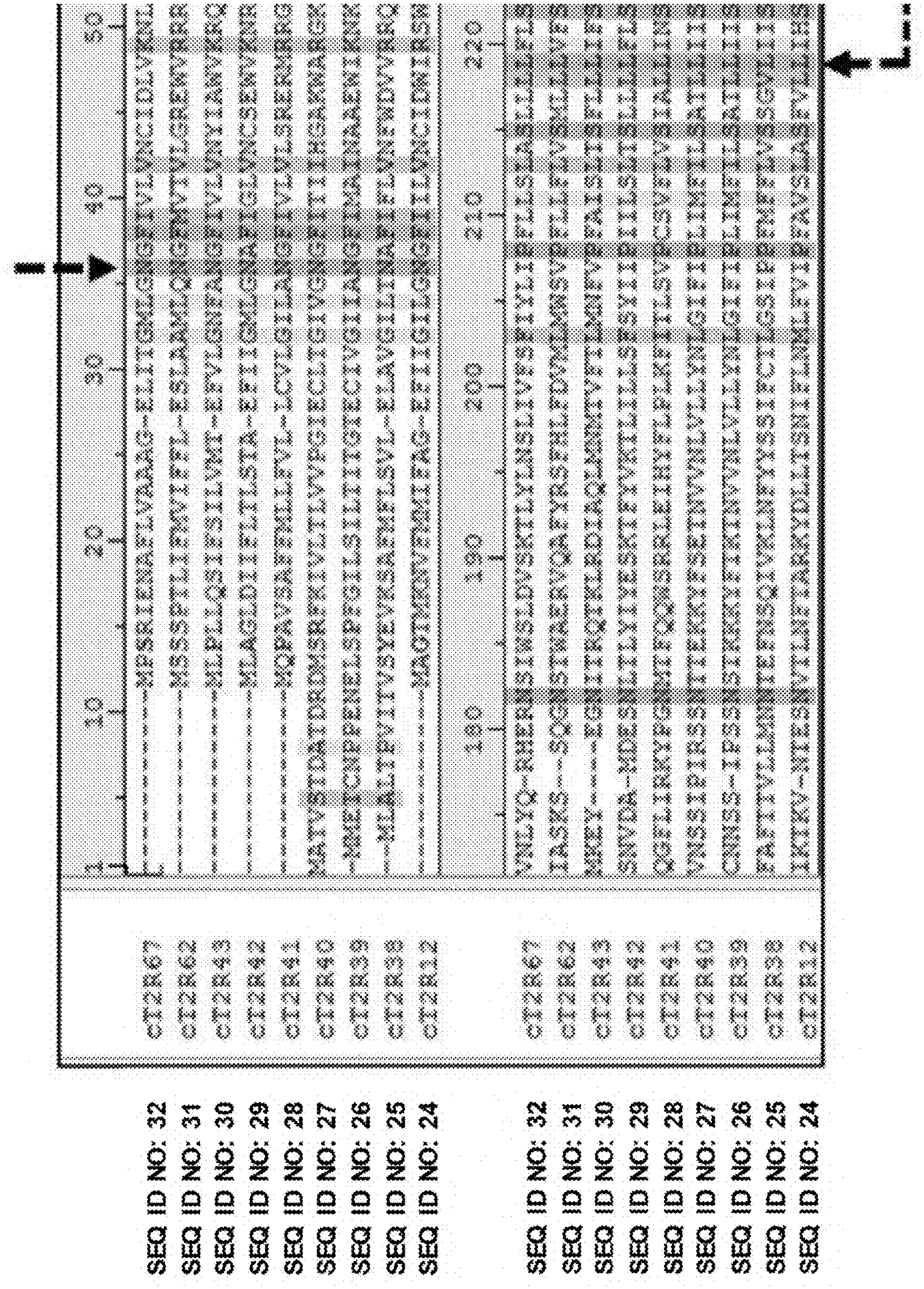
Figure 2B:
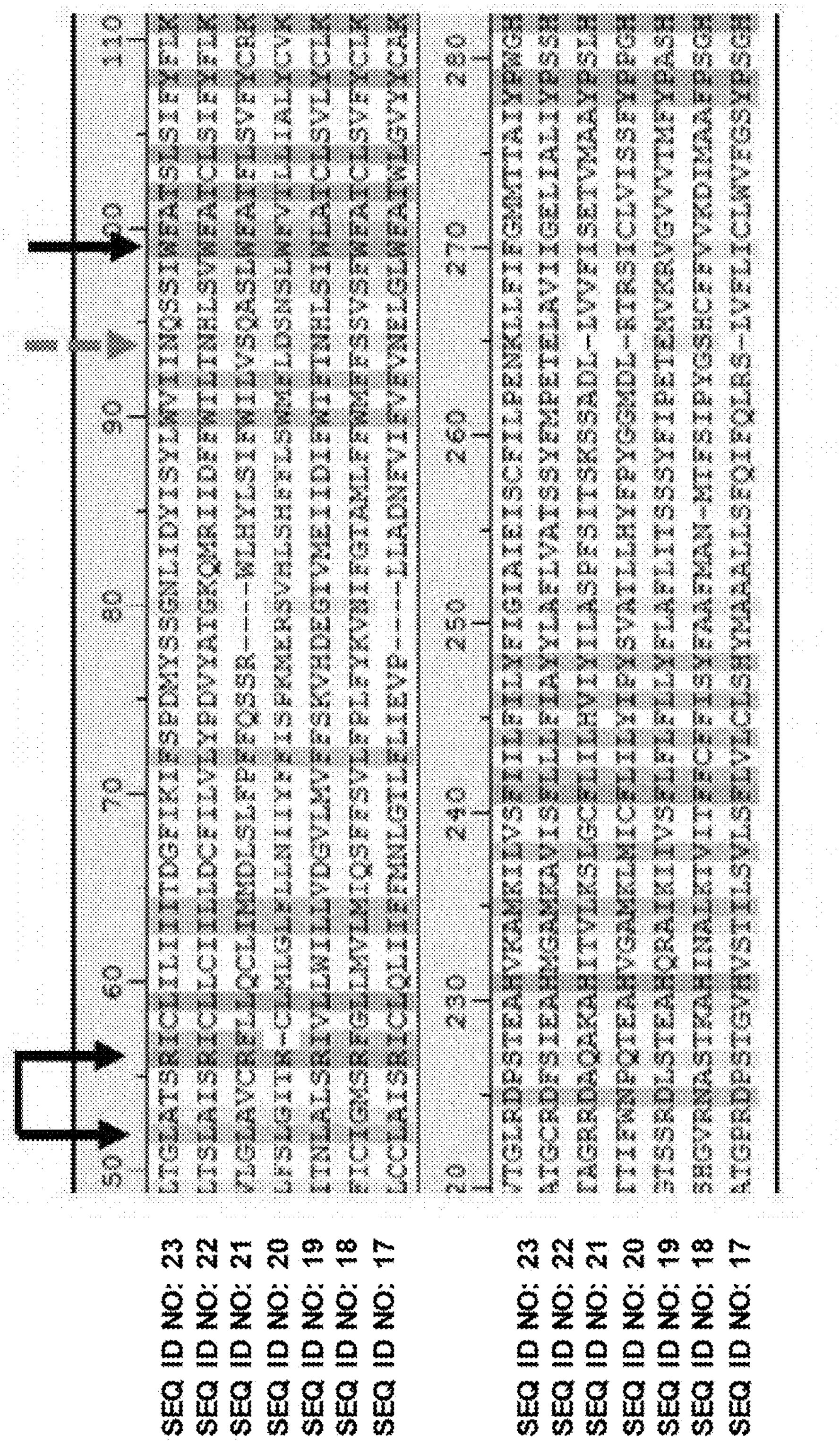
Figure 2B:
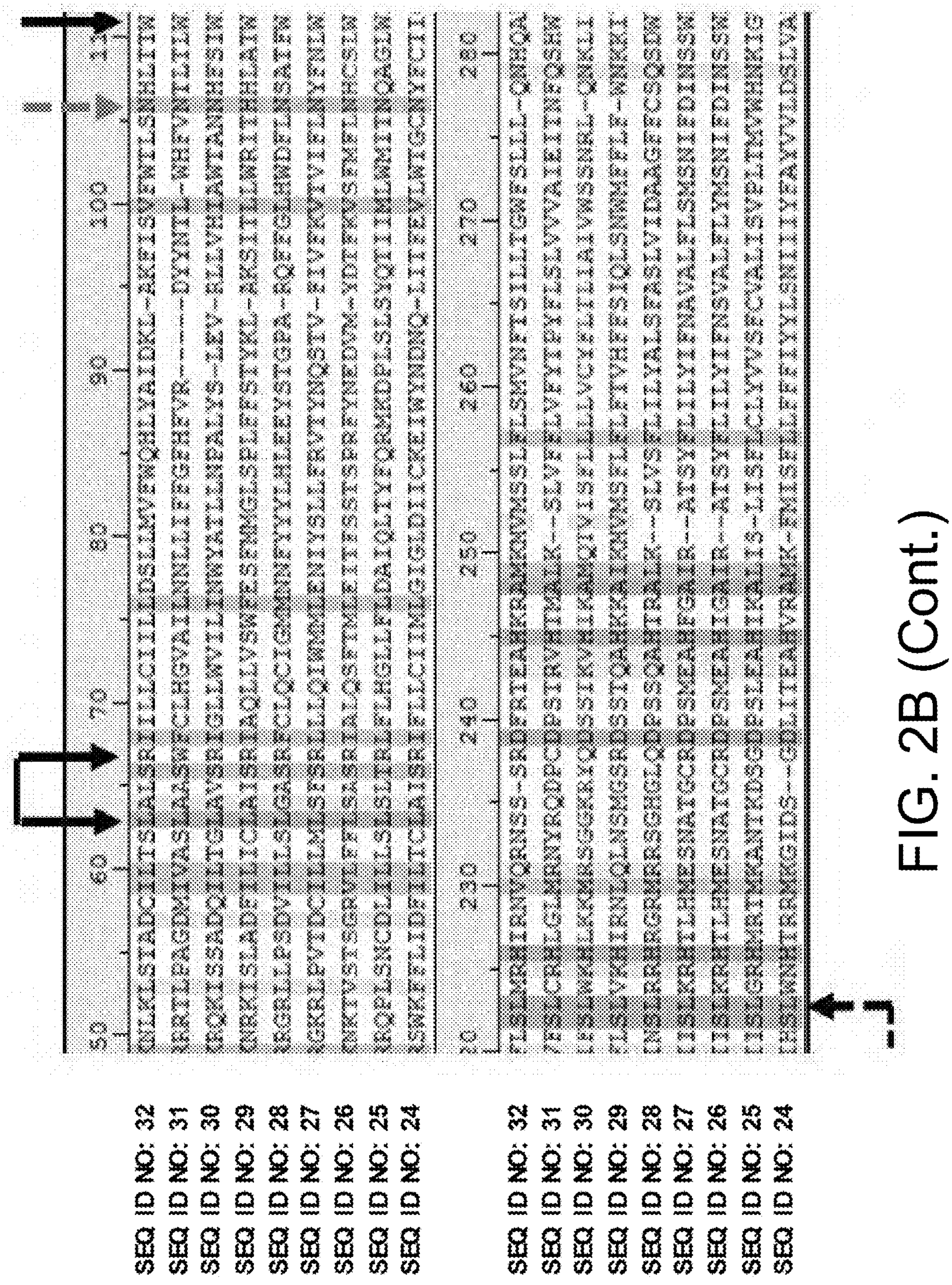
Figure 2C:
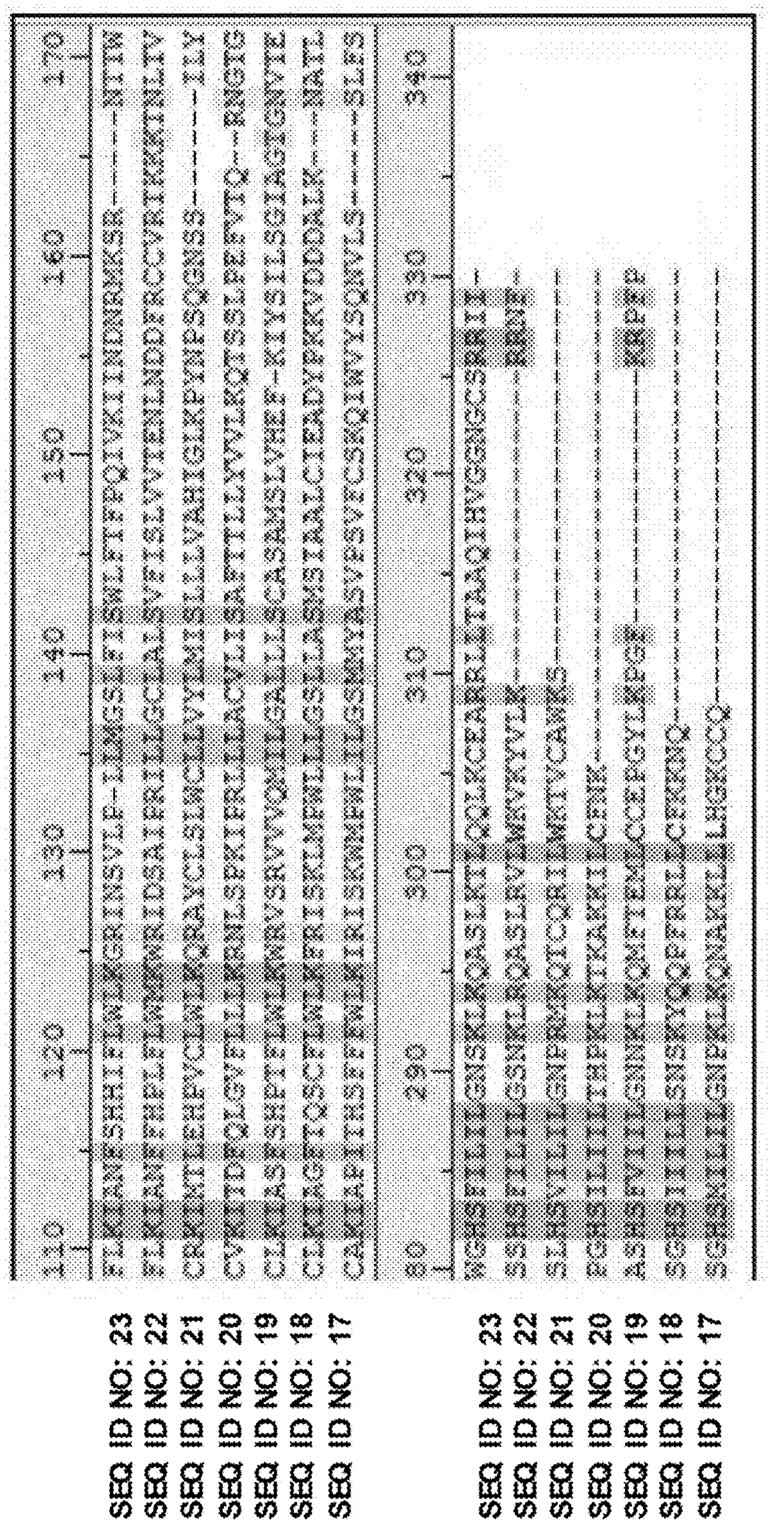
Figure 2C:
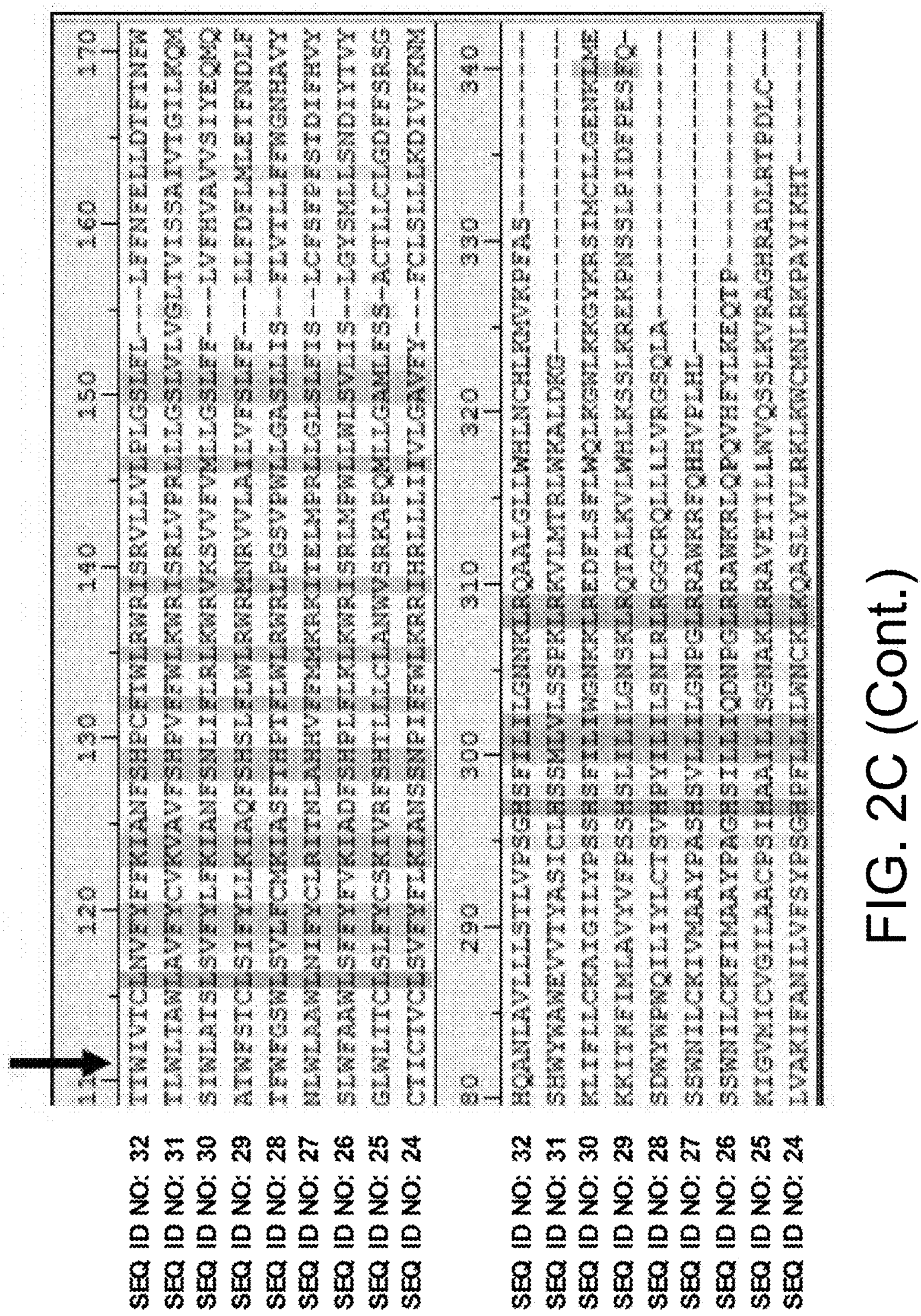
Figure 3A:
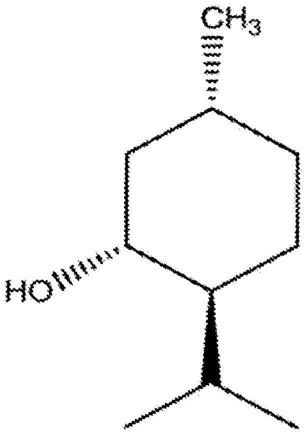
FIG. 3A-E shows (A) the chemical structure of Menthol, (B) in silico modeling of Menthol docked within the active site of the canine T2R1, (C) a close-up view of selected residues lining the active site pocket interacting with, or close to, Menthol, (D) a ligand interaction map demonstrating potential interaction sites between Menthol and T2R1 and (E) a dose-response curve for Menthol when tested against canine T2R1 in vitro. Asn89 can potentially make a hydrogen bond interaction with the ligand. Other residues that can potentially make hydrogen bonding interactions, pi interactions, or charged interactions with the ligand include Tyr239. Residues that can potentially make van der Waals interactions with the ligand include Ile167, Gln174, Glu169, Phe257, Ala242, Phe177, His238, Cys260, Phe264, Leu234, Cys235, Phe85, Leu261, Leu178, Leu181, Val86, and Phe82.
Figure 3B:
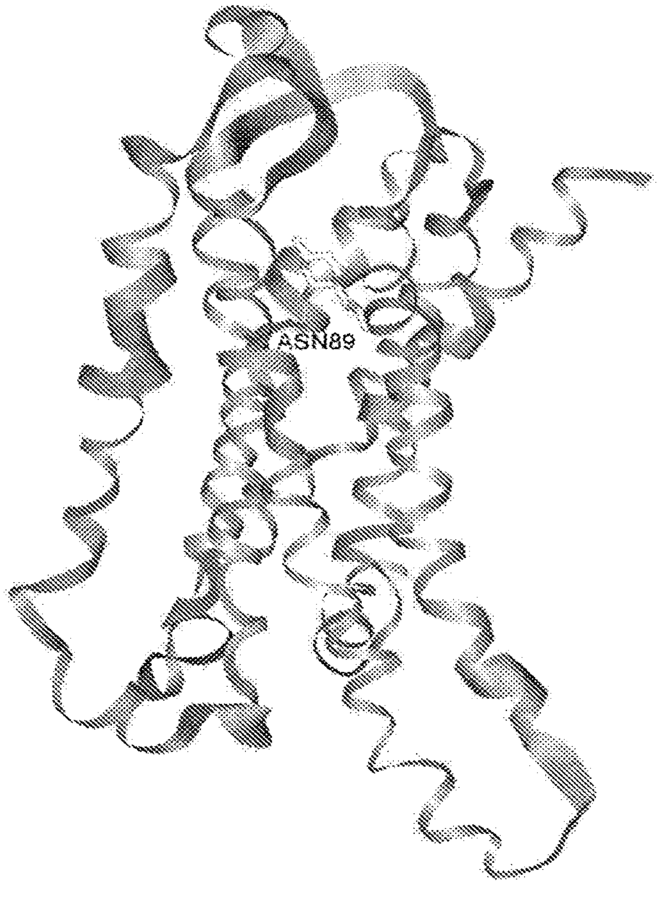
Figure 3C:
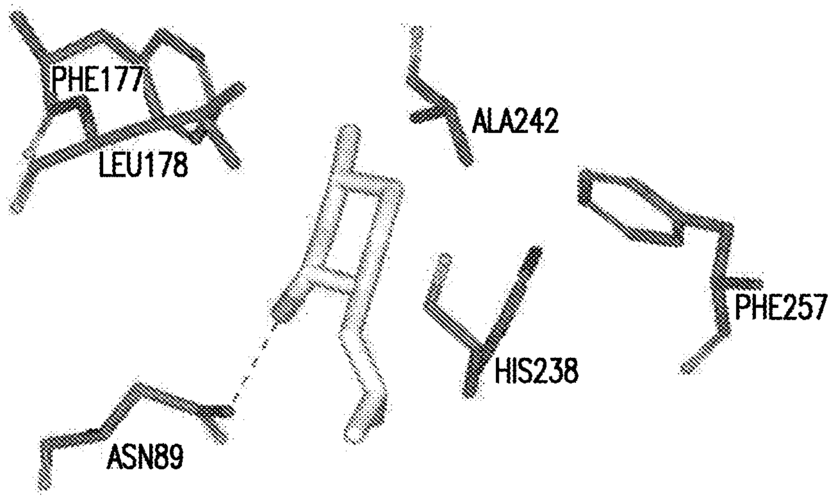
Figure 3D:
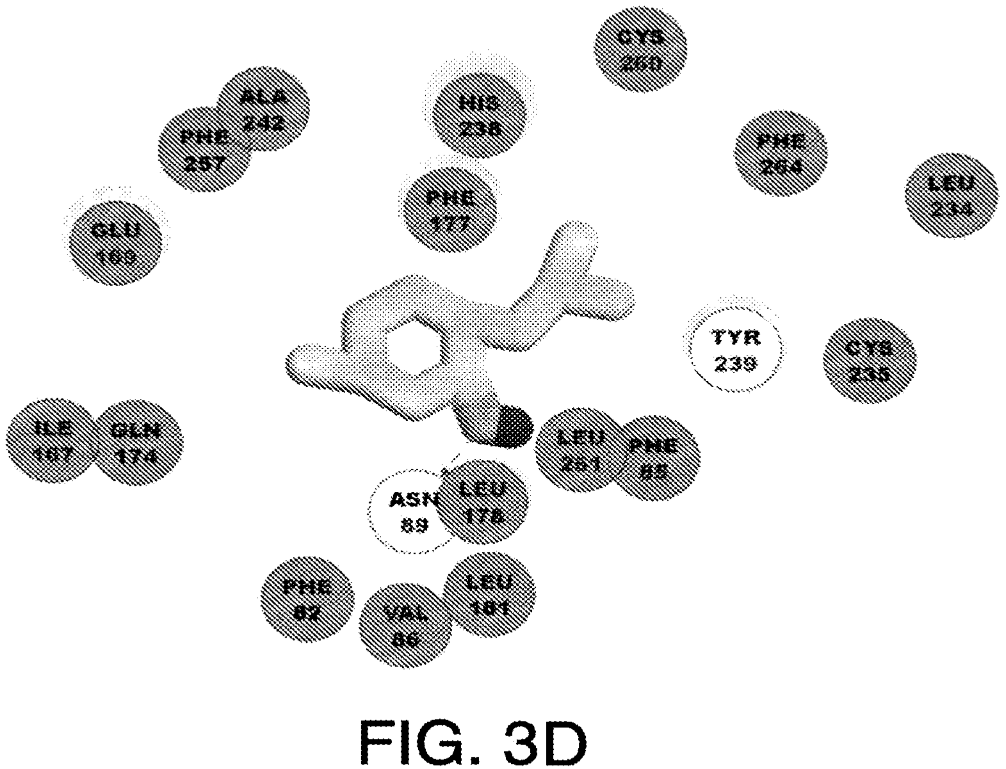
Figure 3E:
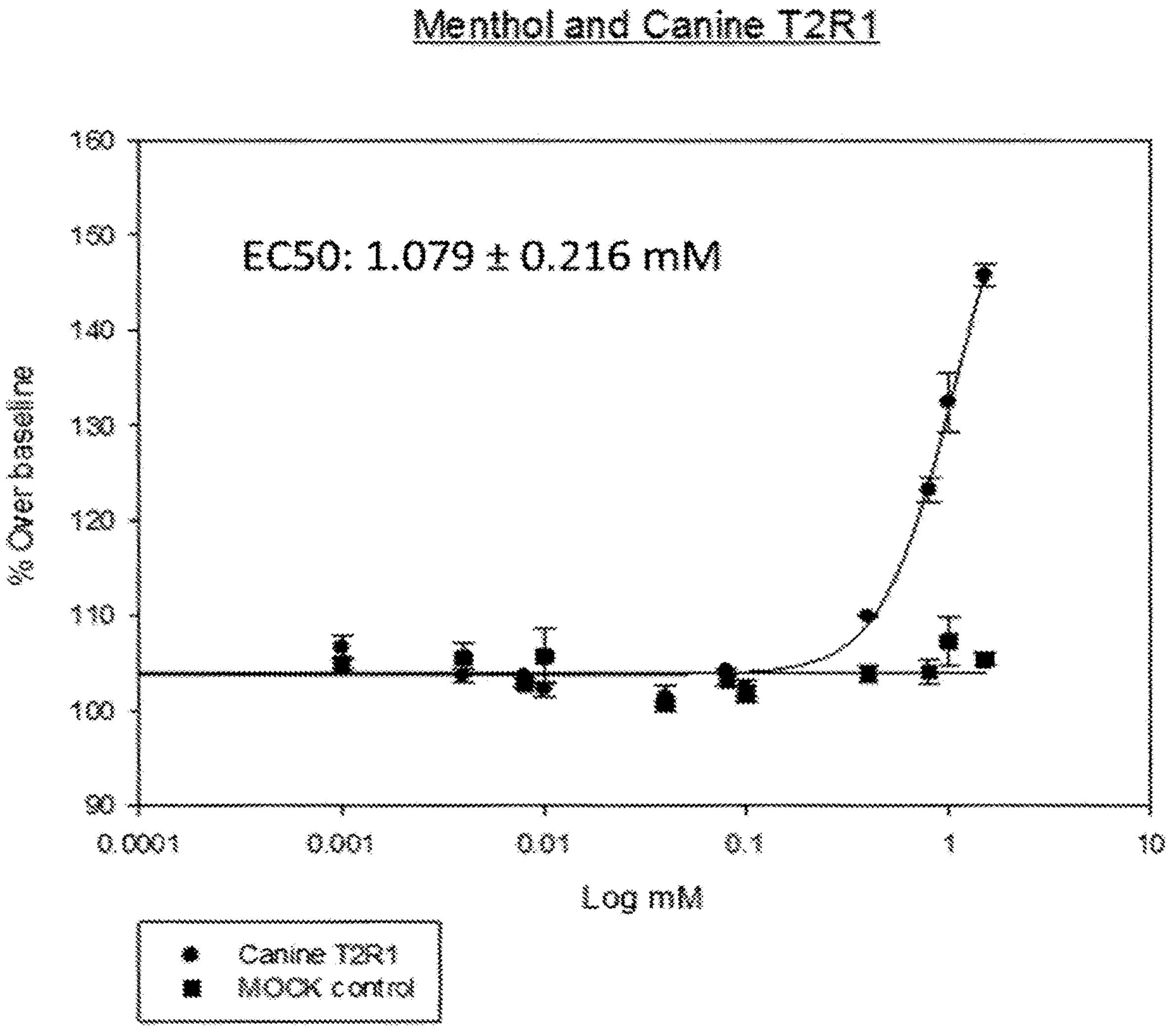
Figure 4A:
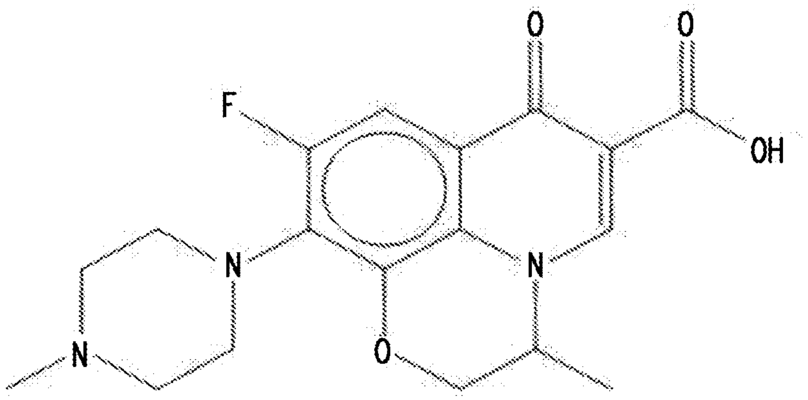
Figure 4B:
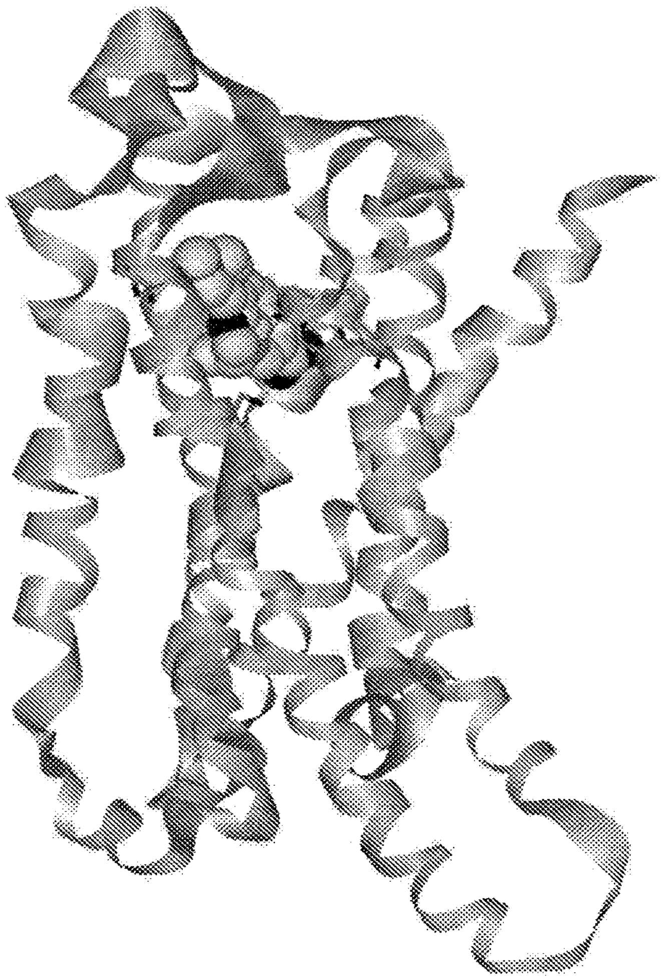
Figure 4C:
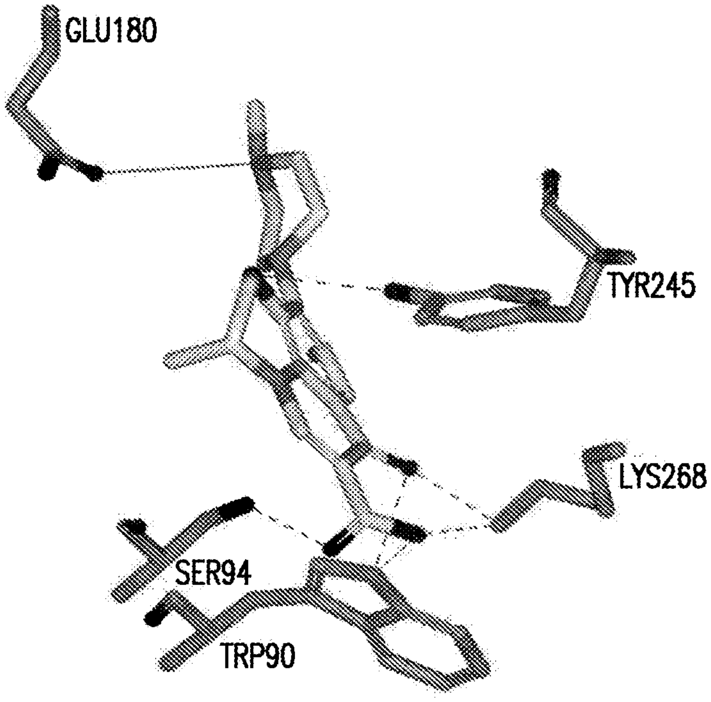
Figure 4D:
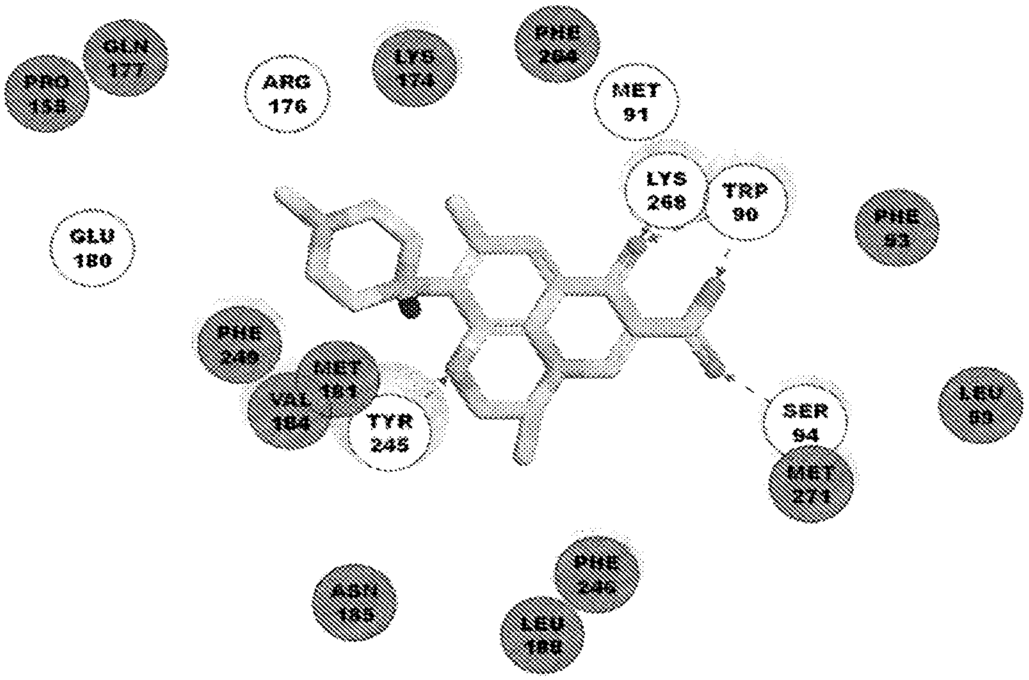
Figure 4E:
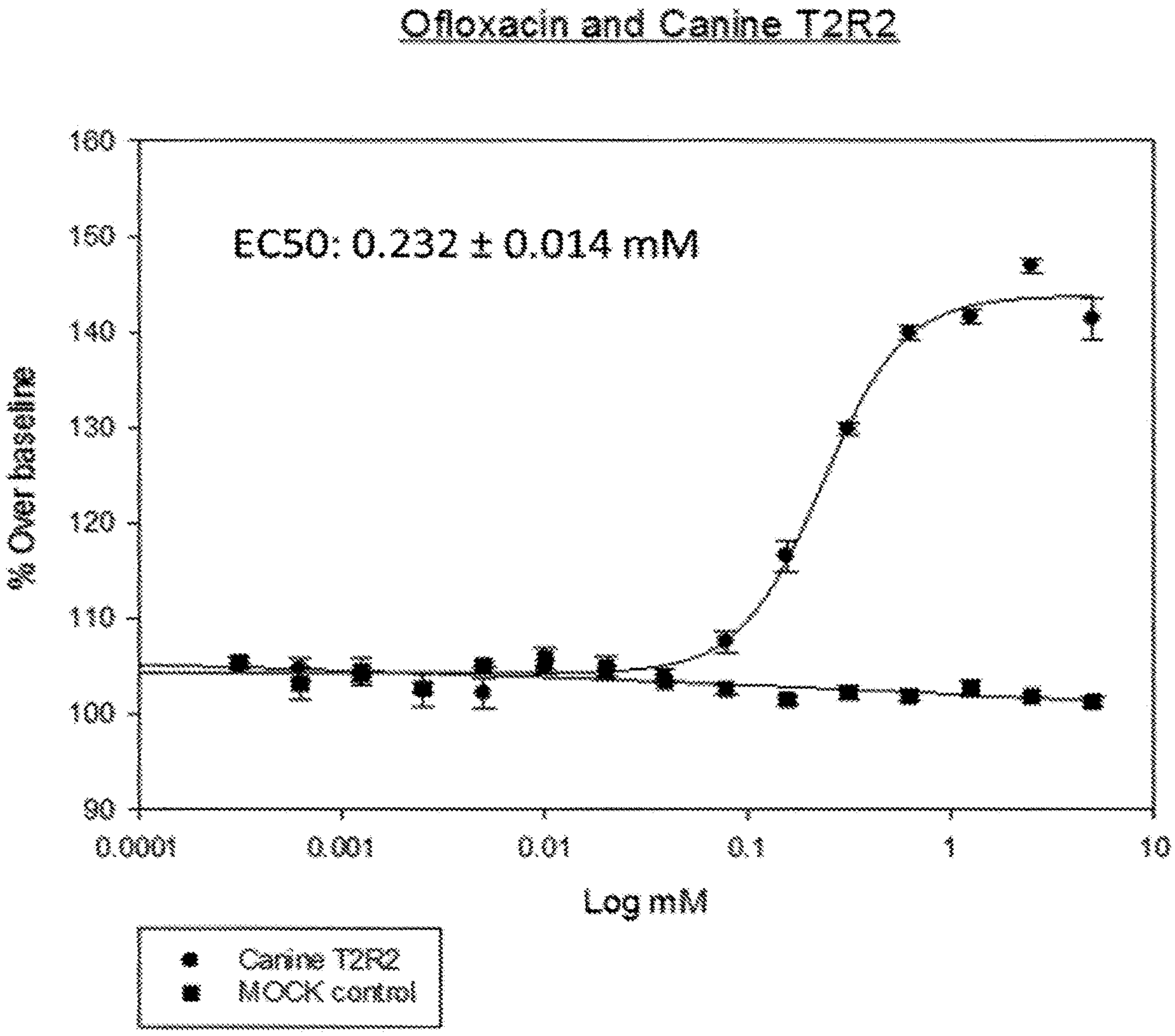
Figure 5A:
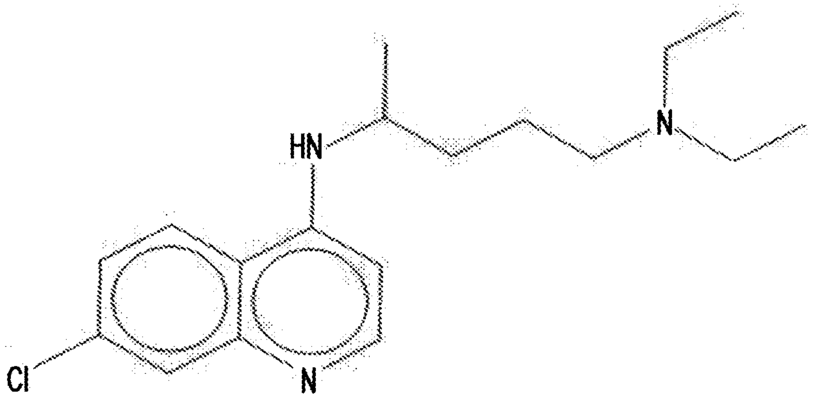
Figure 5B:
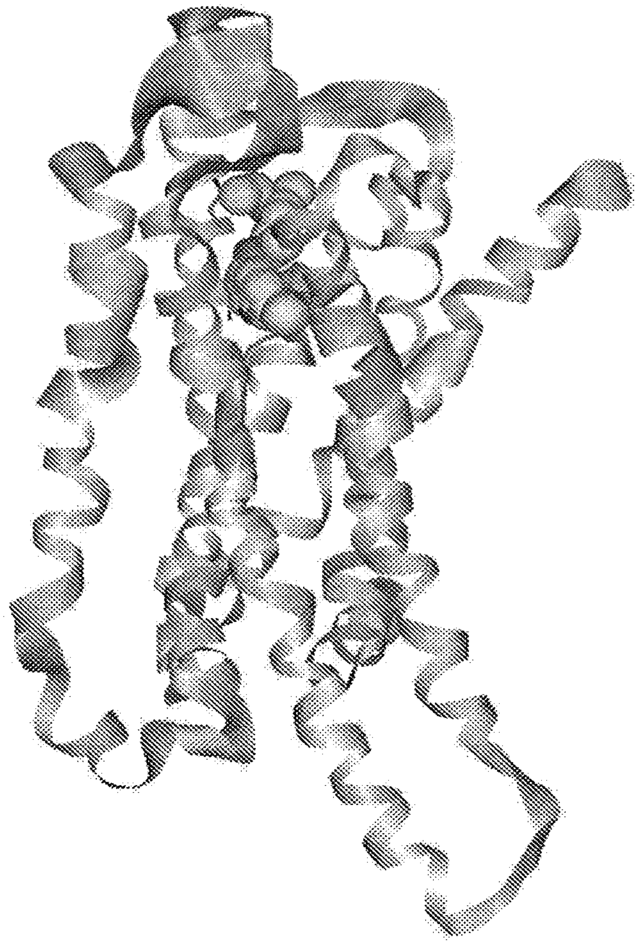
Figure 5C:
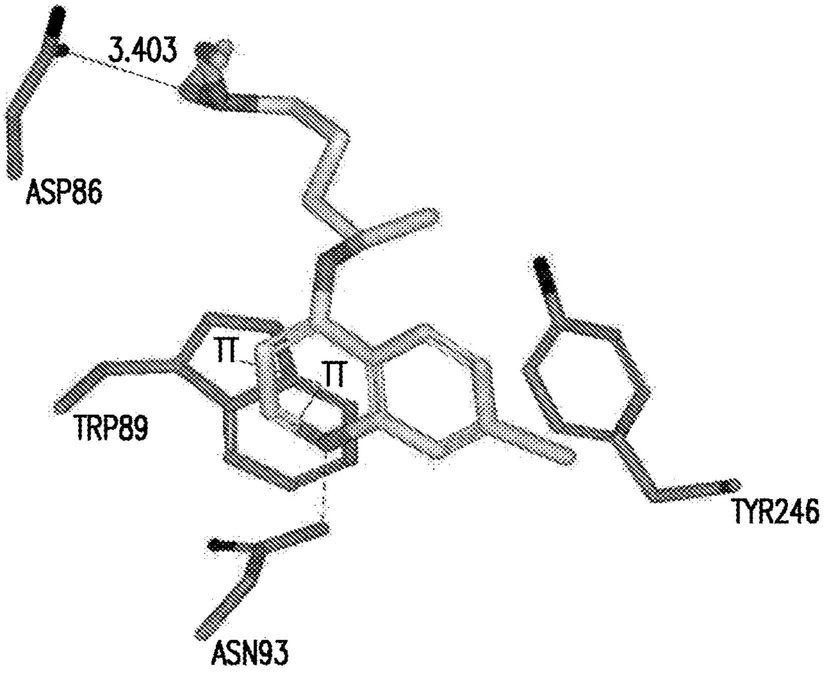
Figure 5D:
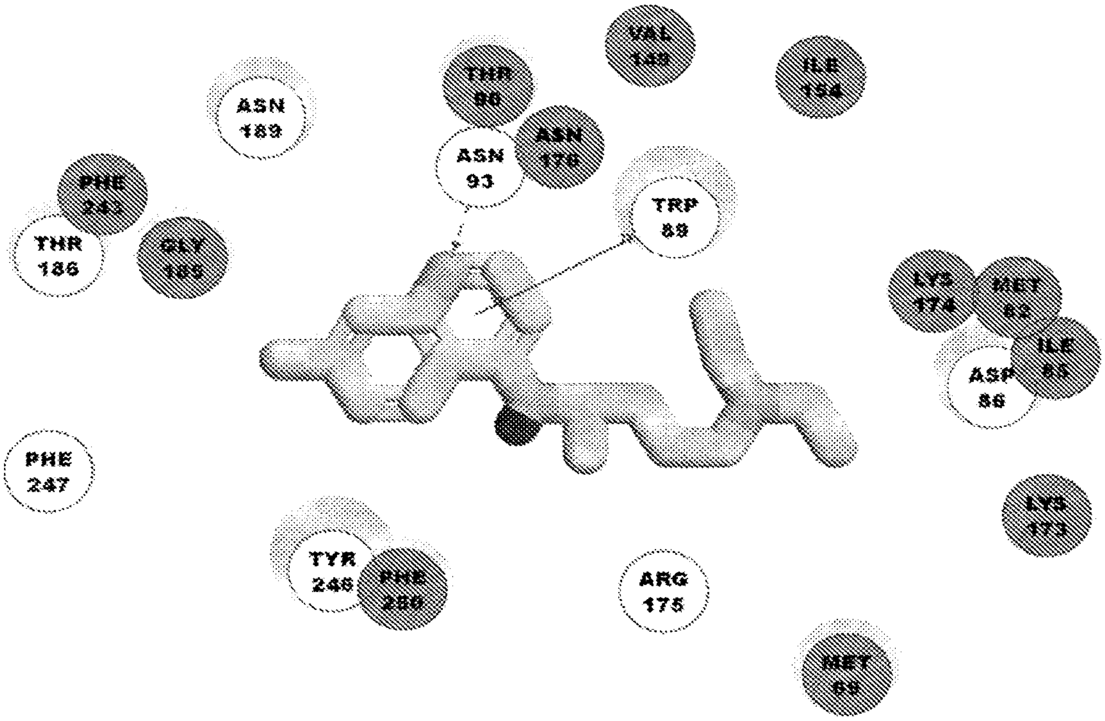
Figure 5E:
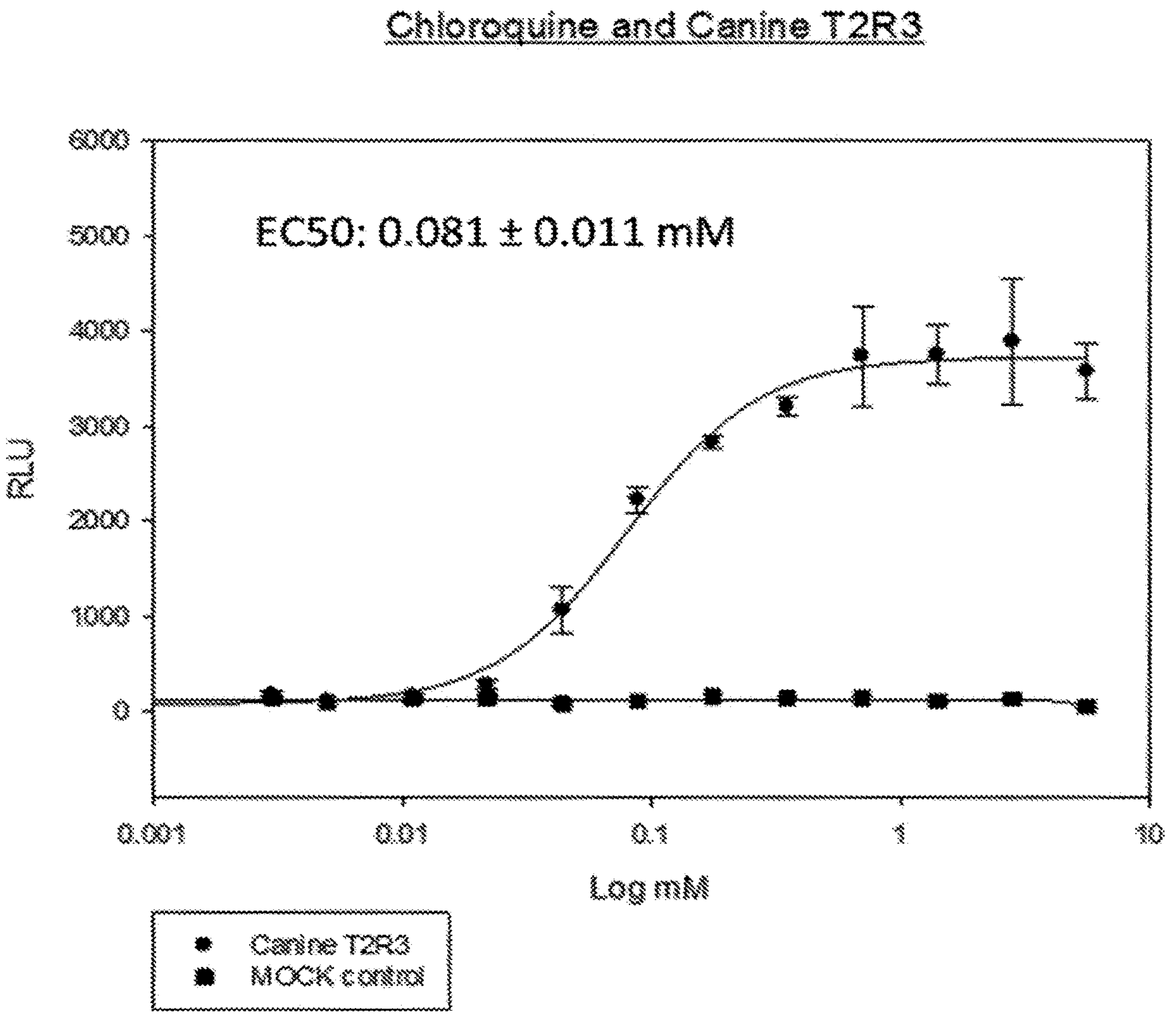
Figure 6A:
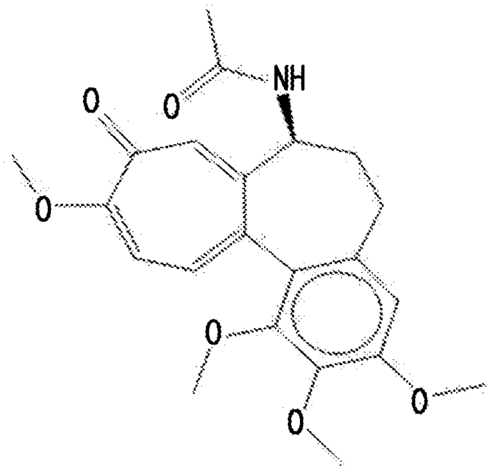
Figure 6B:
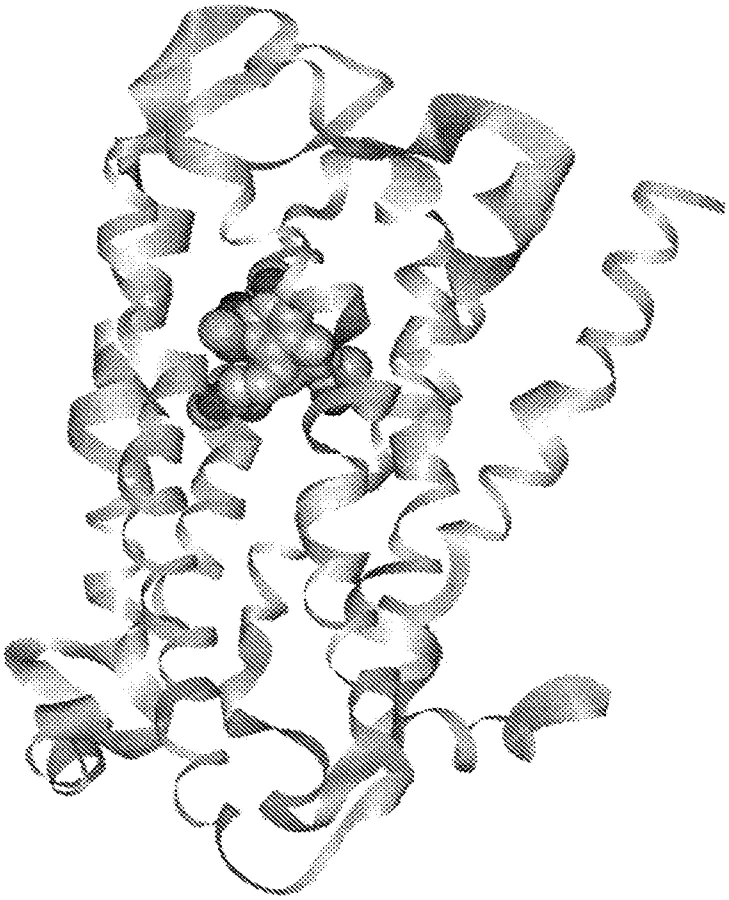
Figure 6C:
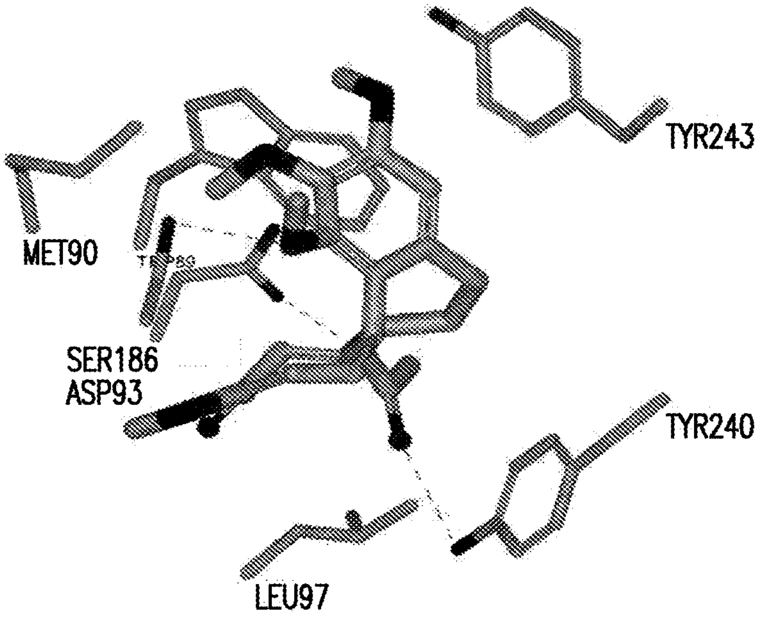
Figure 6D:
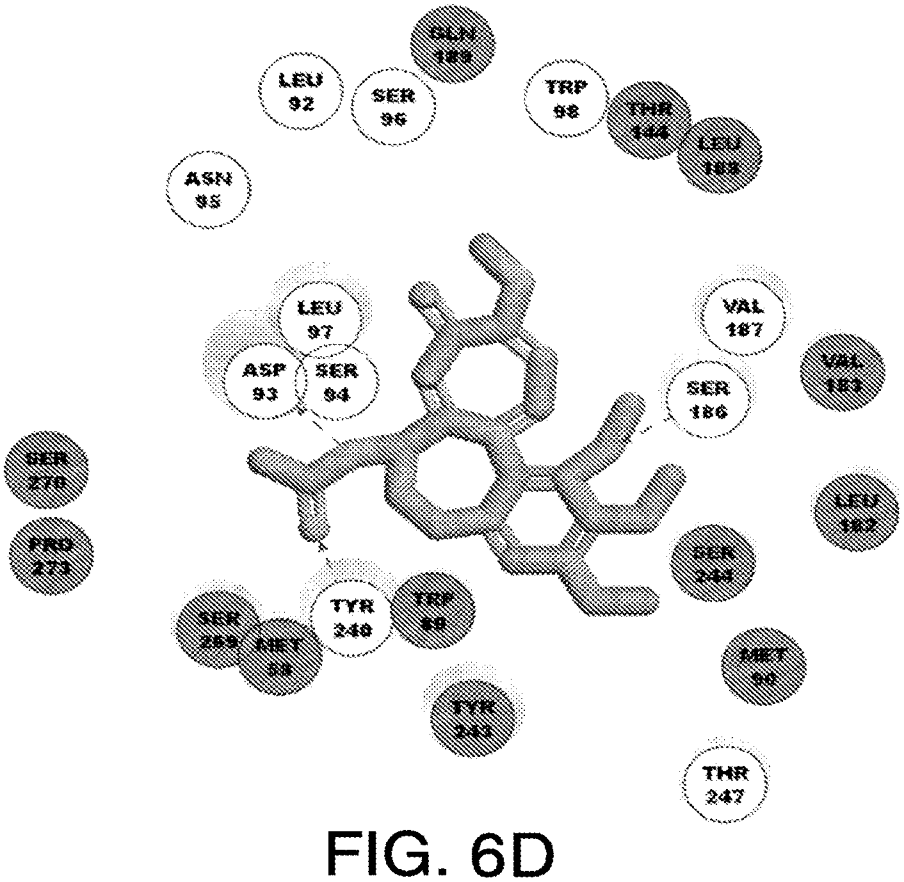
Figure 6E:
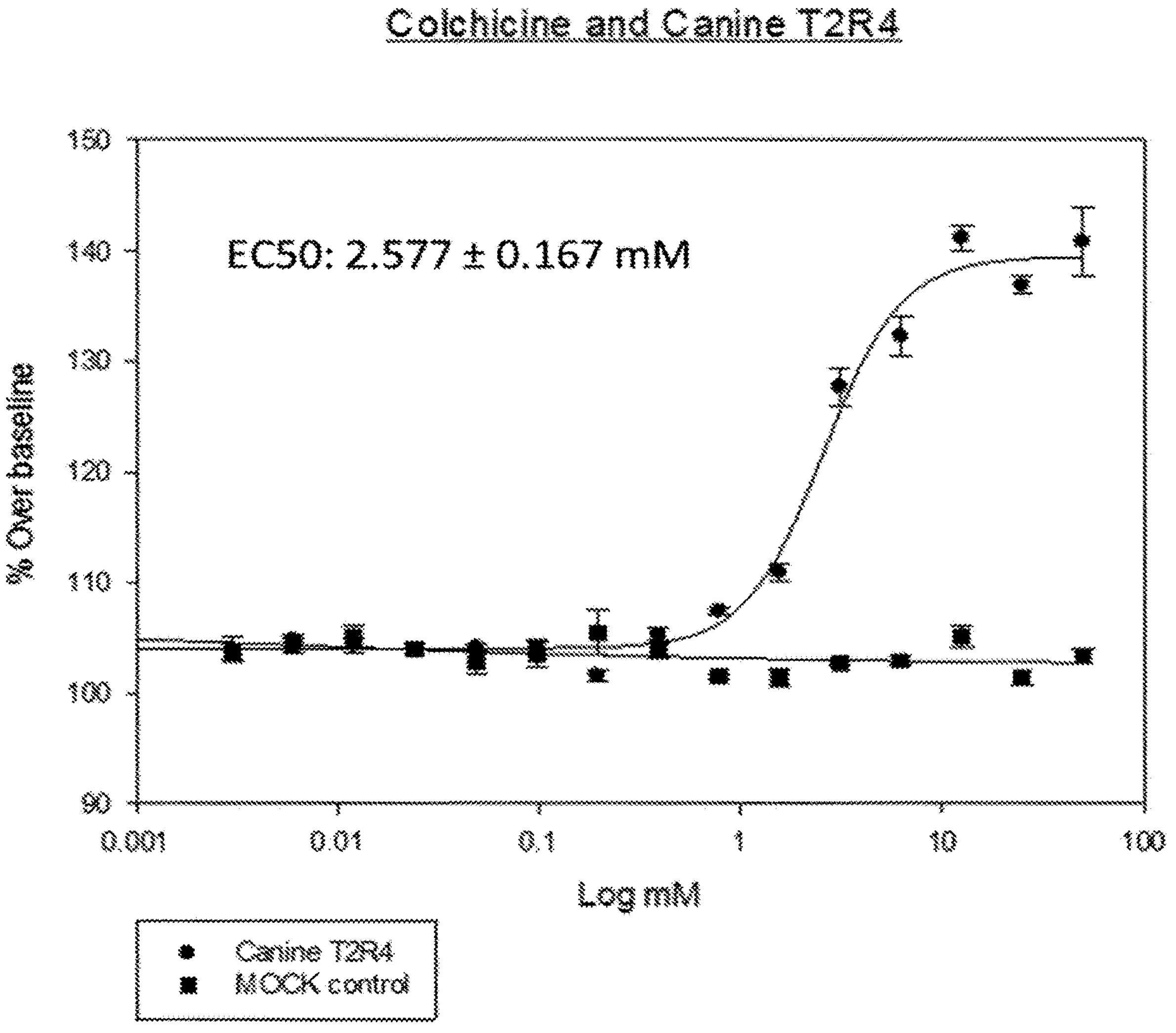
Figure 7A:
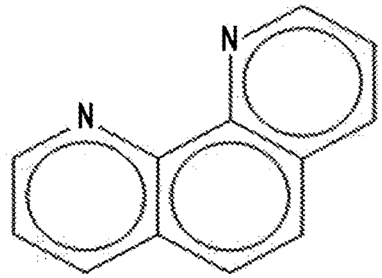
Figure 7B:
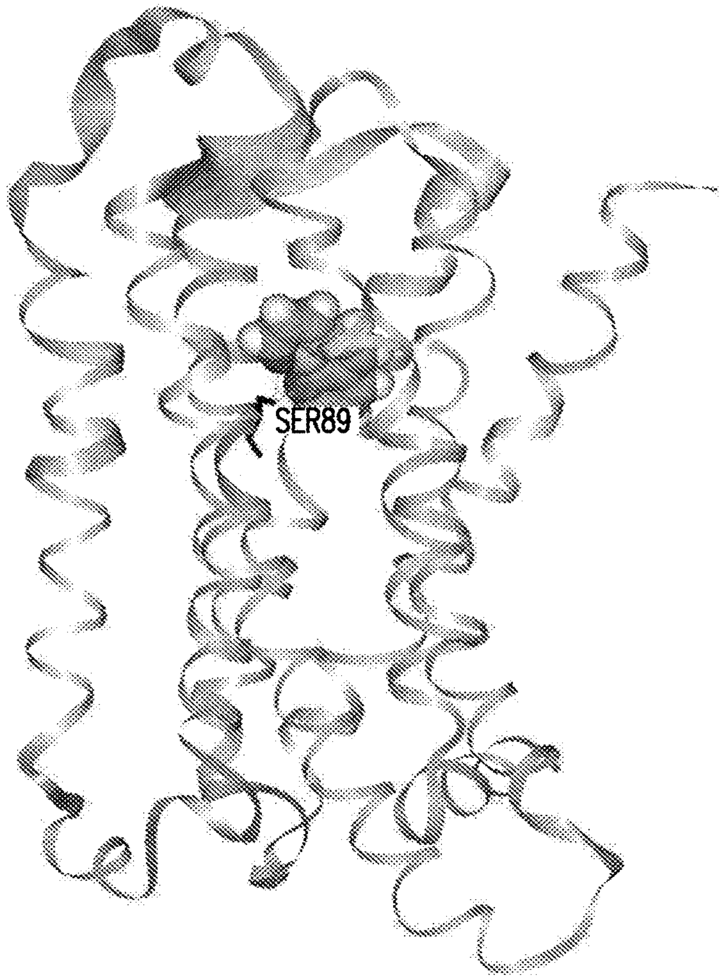
Figure 7C:
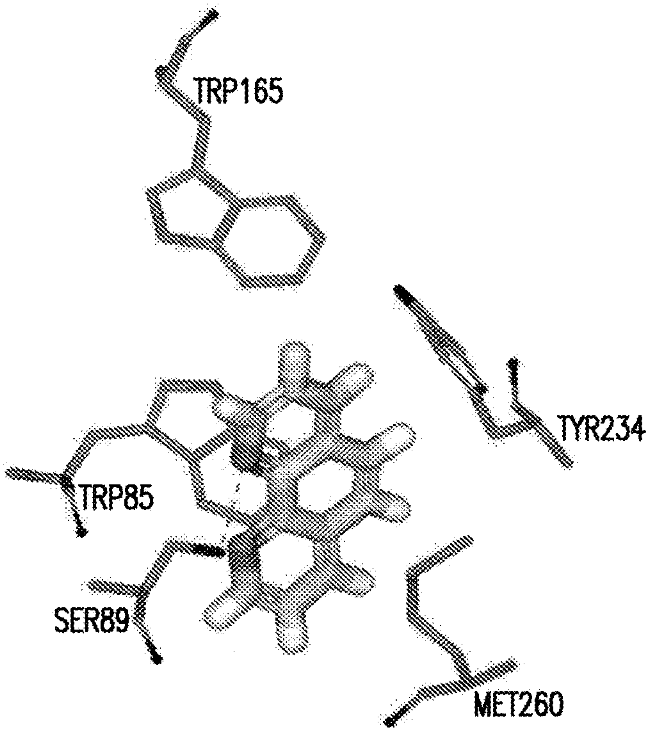
Figure 7D:
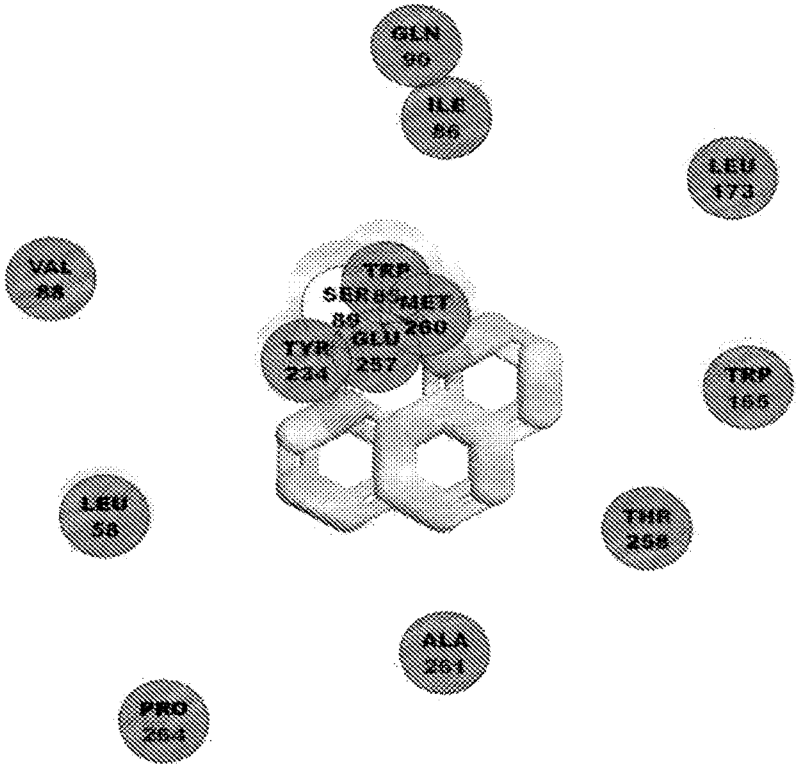
Figure 7E:
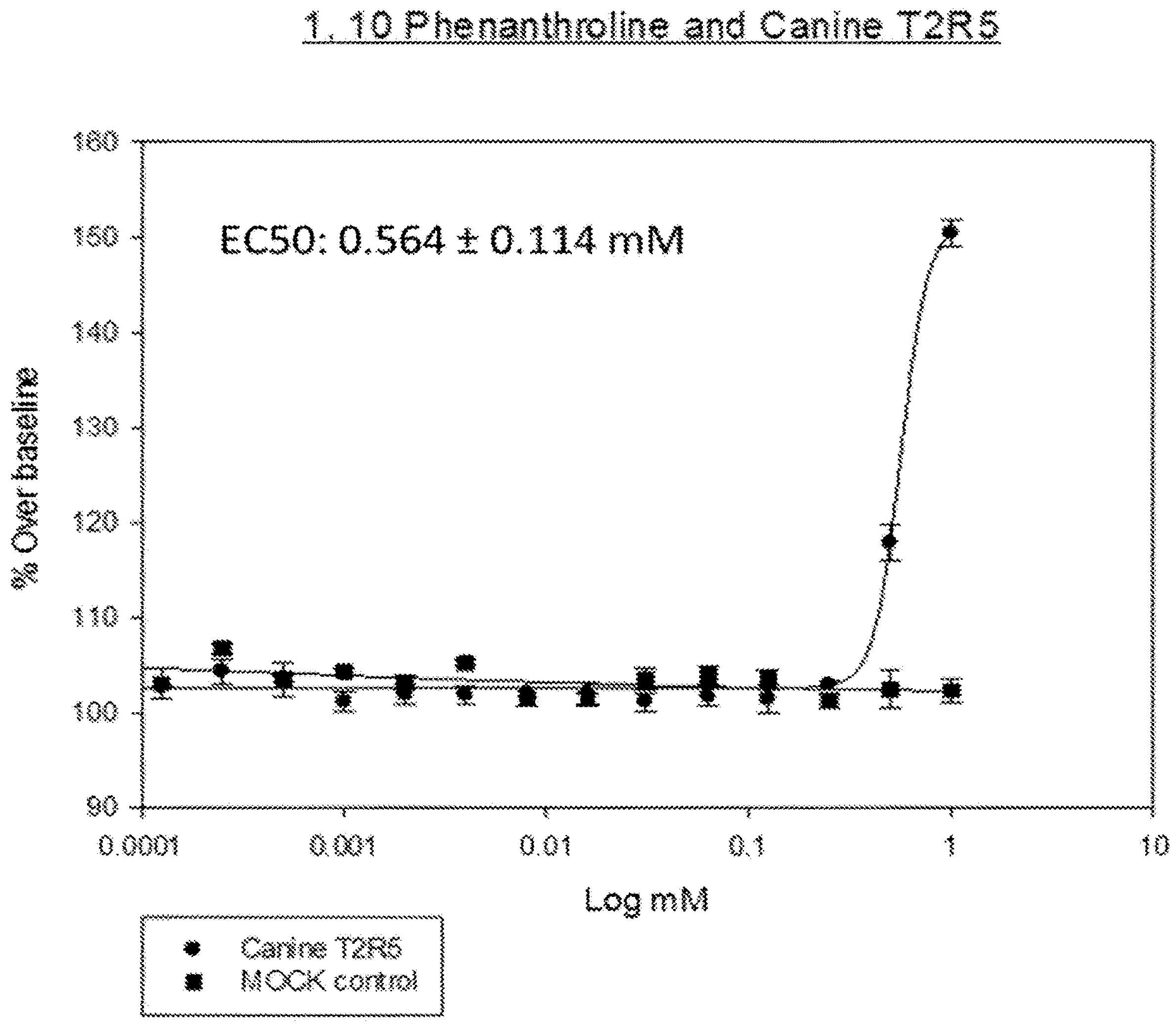
Figure 8A:
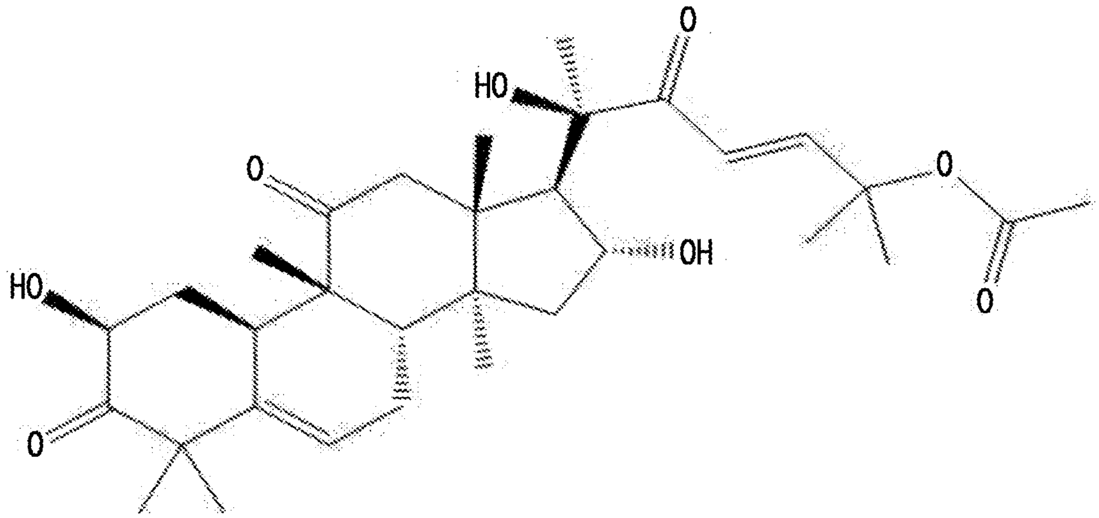
Figure 8B:
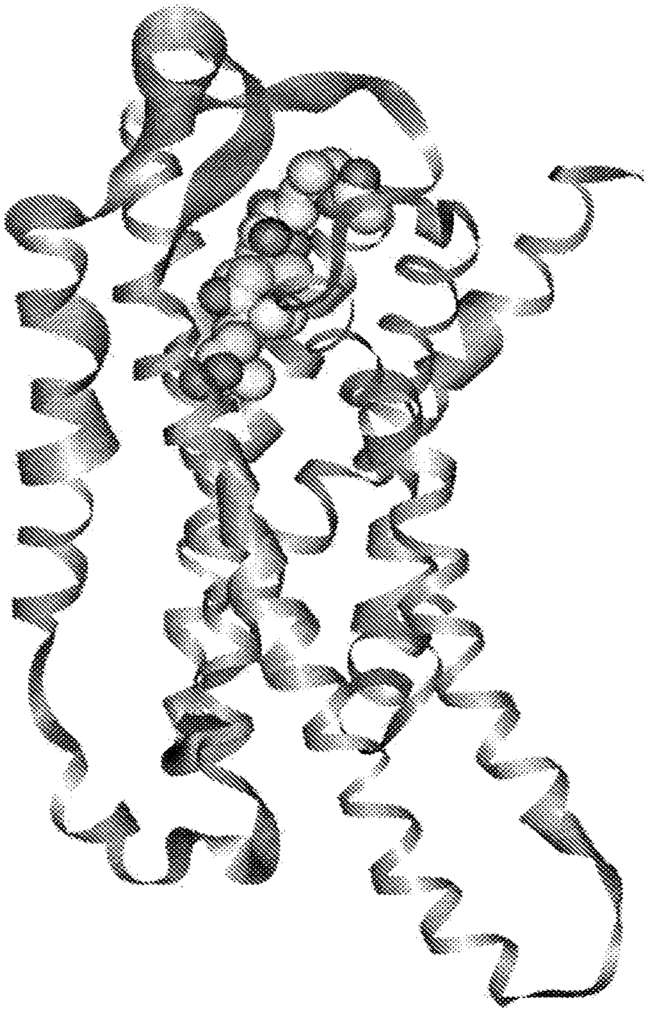
Figure 8C:
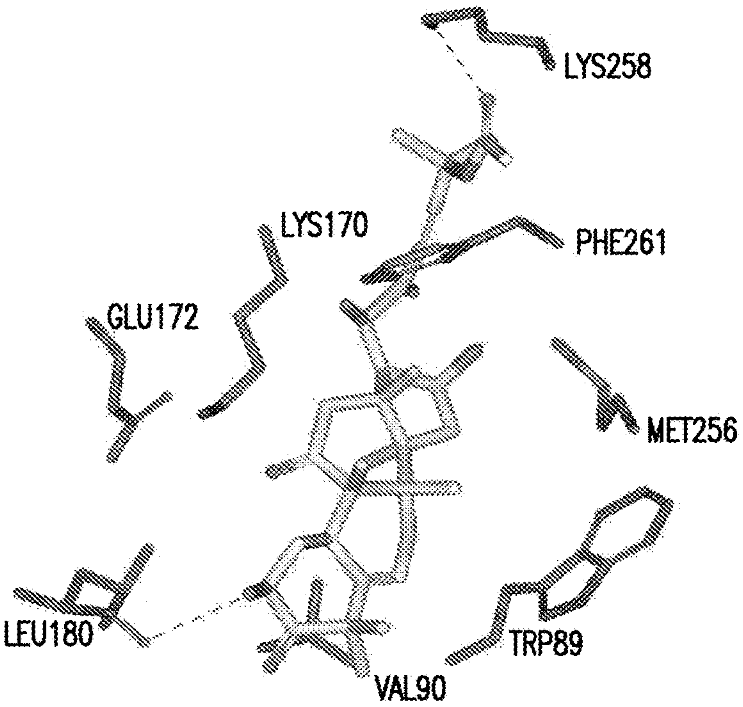
Figure 8D:
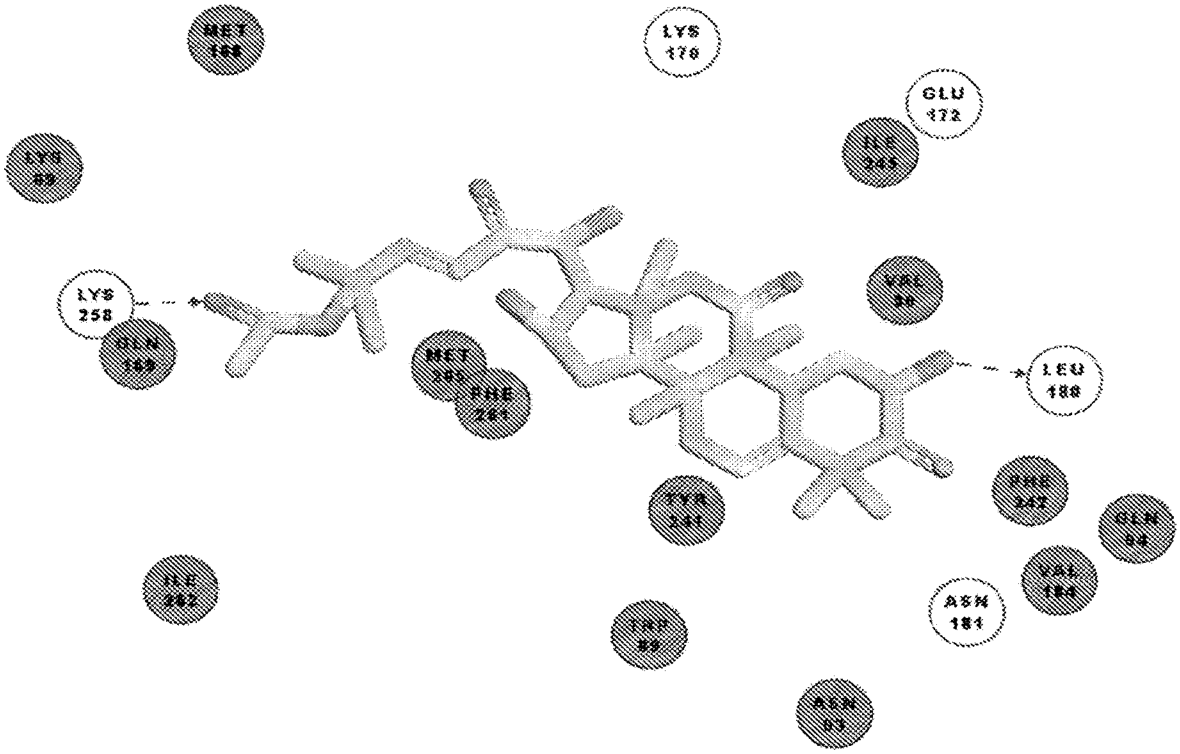
Figure 8E:
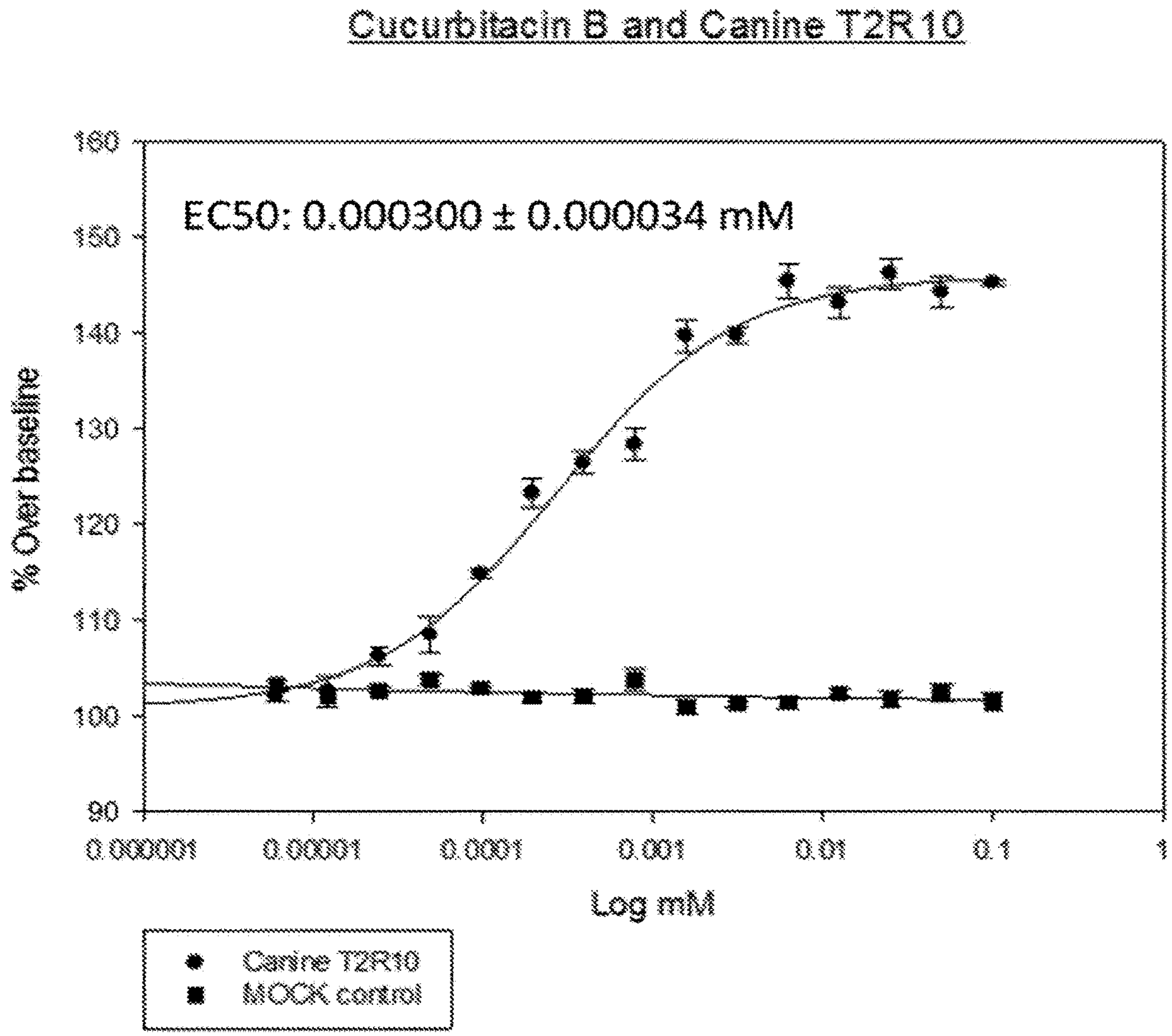
Figure 9A:
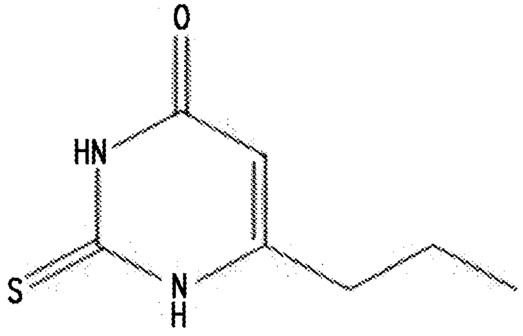
Figure 9B:
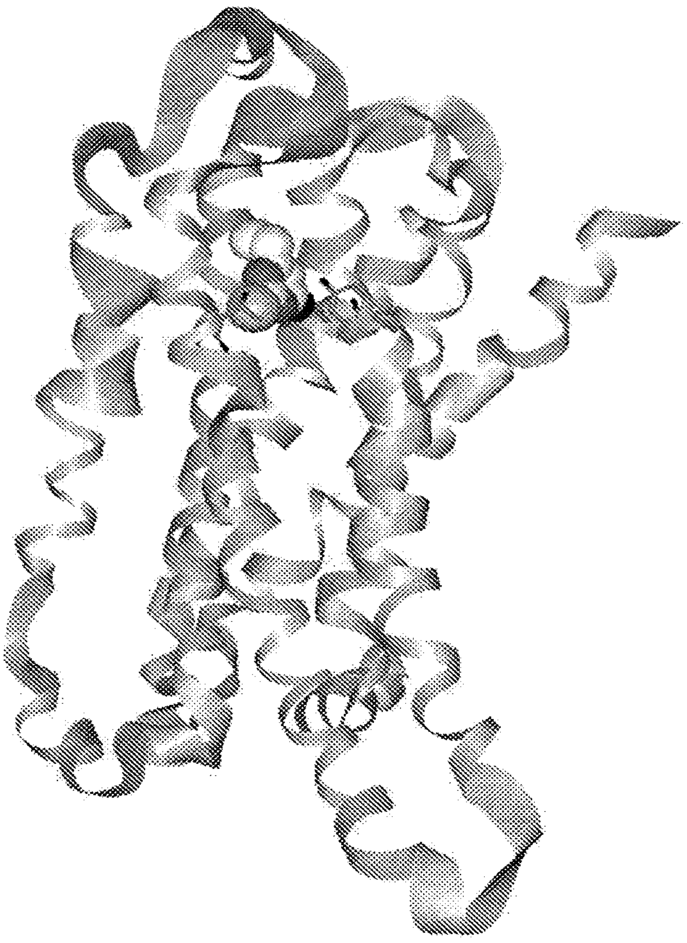
Figure 9C:
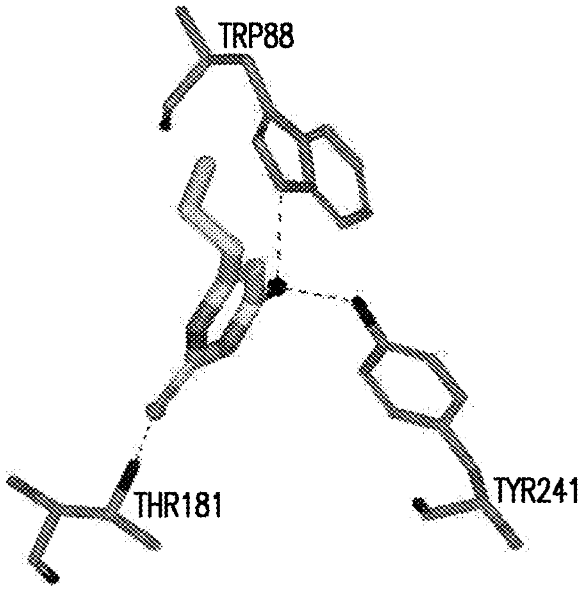
Figure 9D:
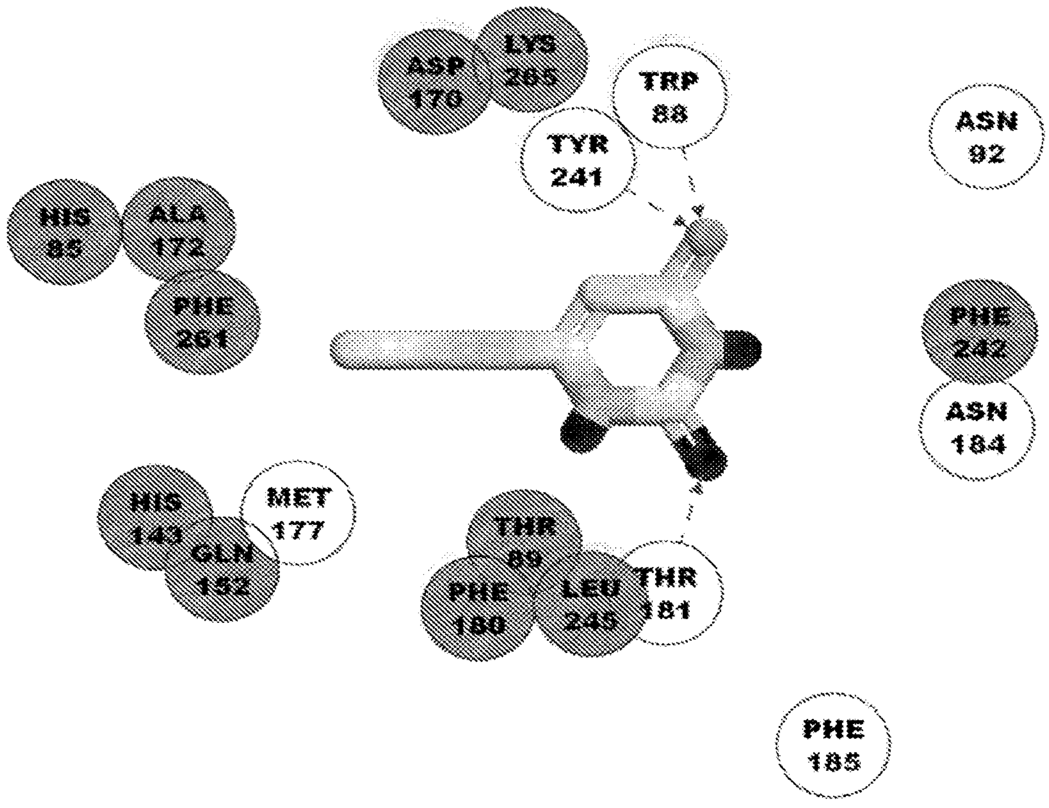
Figure 9E:
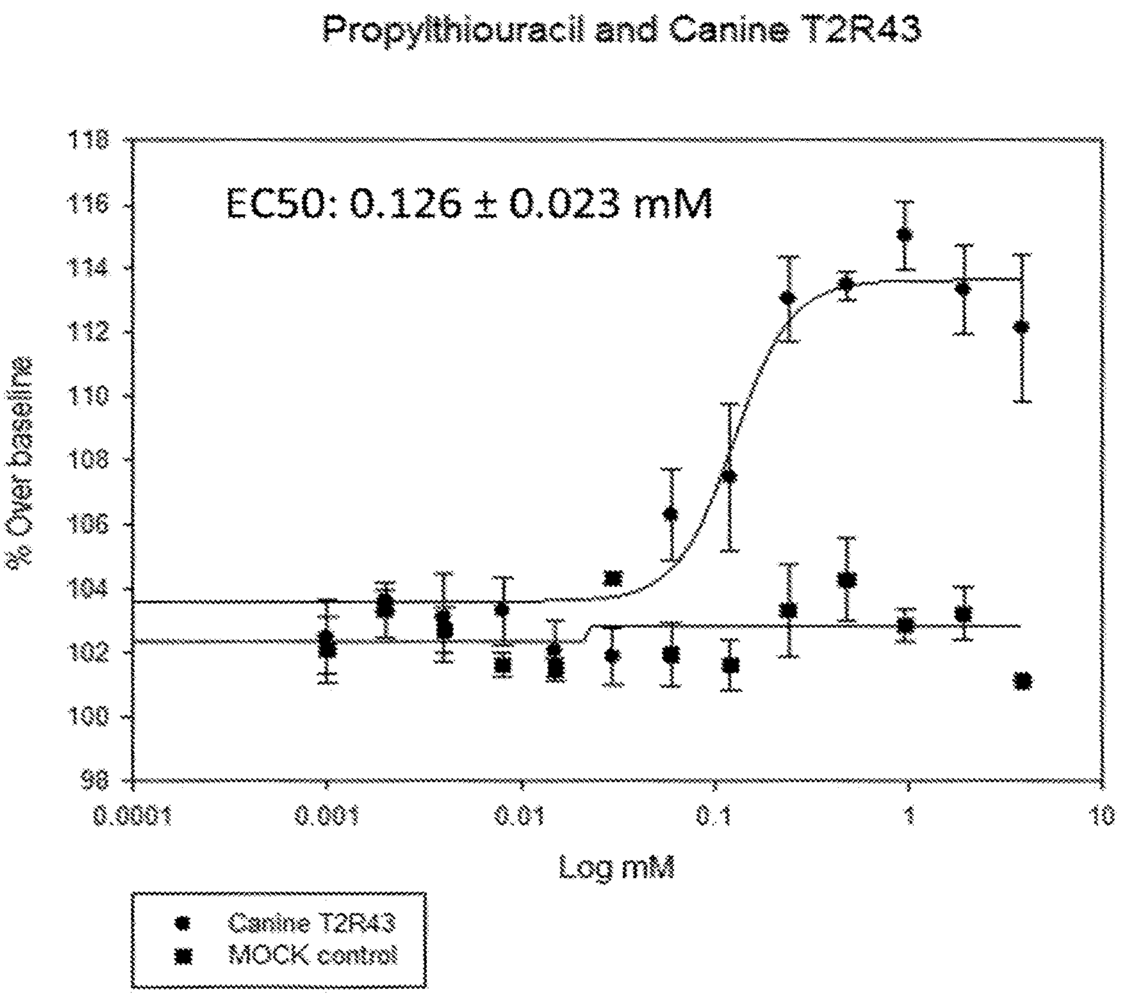

The backbone of the protein is represented as a ribbon to depict the helical nature of the seven transmembrane-helix structure of the receptor. The ligand is shown in space-filling CPK format (Corey et al., Rev Sci Instrum, 24(8): 621-627 (1953)). In this and later FIGS. 3-9) hydrogen bond interactions with the ligand are shown in dotted lines, while salt-bridge and other interactions are shown as solid lines. For the interaction maps hydrogen bonding and other specific interactions are shown as arrows, while residues forming a contact with the ligand are represented as circles. Darker circles represent residues with van der Waals interactions with the ligand, while lighter circles represent residues with polar, hydrogen bonding, Pi interactions, or charged interactions with the ligand. A lighter outer circle around a residue, if present, signals a large change in its solvent accessible surface when the ligand binds. More residues are shown in the schematic interaction maps in (D) than in the 3D model views in (C), since including all of the residues in (C) would obscure the view of the ligand.

During ligand binding and receptor activation, active site rearrangements occur. As such, modeled interactions are dynamic, and may be formed or break dynamically, and may be replaced with other interactions in the vicinity of the ligand during these processes.

FIG. 4A-E shows (A) the chemical structure of Ofloxacin, (B) in silico modeling of Ofloxacin docked within the active site of the canine T2R2, (C) a close-up view of selected residues lining the active site pocket interacting with, or close to, Ofloxacin, (D) a ligand interaction map demonstrating potential interaction sites between Ofloxacin and T2R2 and (E) a dose-response curve for Ofloxacin when tested against canine T2R2 in vitro. Residues that can potentially make hydrogen bond or salt bridge interactions with the ligand include Ser94, Trp90, Lys268, Tyr245, and Glu180. Additional residues that can potentially make polar, hydrogen bonding, pi interactions, or charged interactions with the ligand include Arg176 and Met91. Additional residues that can potentially make van der Waals interactions with the ligand include Asn185, Val184, Met181, Phe249, Pro155, Gln177, Lys174, Phe264, Phe93, Leu59, Met271, Phe246, and Leu188.

FIG. 5A-E shows (A) the chemical structure of Chloroquine, (B) in silico modeling of Chloroquine docked within the active site of the canine T2R3, (C) a close-up view of selected residues lining the active site pocket interacting with, or close to, Chloroquine, (D) a ligand interaction map demonstrating potential interaction sites between Chloroquine and T2R3 and (E) a dose-response curve for Chloroquine when tested against canine T2R3 in vitro. Residues that can make hydrogen bonding or charged interactions with the ligand include Asn93 and Asp86. Additional residues that can make polar, hydrogen bonding, pi interactions, or charged interactions with the ligand include Tyr246, Phe247, Thr186, Asn189, Trp89, and Arg175. Additional residues making primarily van der Waals interactions with the ligand include Phe250, Gly185, Phe243, Thr90, Asn176, Val149, Ile154, Lys174, Met82, Ile85, Lys173, and Met69.

FIG. 6A-E shows (A) the chemical structure of Colchicine, (B) in silico modeling of Colchicine docked within the active site of the canine T2R4, (C) a close-up view of selected residues lining the active site pocket interacting with, or close to, Colchicine, (D) a ligand interaction map demonstrating potential interaction sites between Colchicine and T2R4 and (E) a dose-response curve for Colchicine when tested against canine T2R4 in vitro. Ser186, Asp93, and Tyr240 can potentially make a hydrogen bond with the ligand. Additional residues that can potentially make polar, hydrogen bonding, pi interactions, or charged interactions with the ligand include Ser94, Leu97, Asn95, Leu92, Ser96, Trp98, Val187, and Thr247. Residues that can potentially make van der Waals interactions with the ligand include Tyr243, Trp89, Met58, Ser269, Pro273, Ser270, Gln189, Thr144, Leu188, Val183, Leu182, Ser244, and Met90.

FIG. 7A-E shows (A) the chemical structure of 1, 10 Phenanthroline, (B) in silico modeling of 1,10 Phenanthroline docked within the active site of the canine T2R5, (C) a close-up view of selected residues lining the active site pocket interacting with, or close to, 1, 10 Phenanthroline, (D) a ligand interaction map demonstrating potential interaction sites between 1,10 Phenanthroline and T2R5 and (E) a dose-response curve for 1, 10 Phenanthroline when tested against canine T2R5 in vitro. There is a potential hydrogen bond between Ser89 and each nitrogen of 1, 10 Phenanthroline. Additional residues that can potentially make van der Waals or Pi interactions with the ligand include Pro264, Leu58, Val88, Gln90, Ile86, Leu173, Trp165, Thr258, Ala261, Tyr234, Glu257, Met260, and Trp85.

FIG. 8A-E shows (A) the chemical structure of Cucurbitacin B, (B) in silico modeling of Cucurbitacin B docked within the active site of the canine T2R10, (C) a close-up view of selected residues lining the active site pocket interacting with, or close to, Cucurbitacin B, (D) a ligand interaction map demonstrating potential interaction sites between Cucurbitacin B and T2R10 and (E) a dose-response curve for Cucurbitacin B when tested against canine T2R10 in vitro. Lys258 and Leu180 (backbone) can potentially make hydrogen bonds with the ligand. Additional residues that can potentially make polar, hydrogen bonding, pi interactions, or charged interactions with the ligand include Lys170, Glu172, and Asn181. Residues that can potentially make van der Waals interactions with the ligand include Phe261, Met265, Ile262, Gln169, Lys69, Met168, Ile245, Val90, Phe242, Gln94, Val184, Asn93, Trp89, and Tyr241.

FIG. 9A-E shows (A) the chemical structure of Propylthiouracil, (B) in silico modeling of Propylthiouracil docked within the active site of the canine T2R43, (C) a close-up view of selected residues lining the active site pocket interacting with, or close to, Propylthiouracil, (D) a ligand interaction map demonstrating potential interaction sites between Propylthiouracil and T2R43 and (E) a dose-response curve for Propylthiouracil when tested against canine T2R43 in vitro. Residues that can potentially make hydrogen bond or charged interactions with the ligand include Tyr241, Trp88, and Thr181. Additional residues that can potentially make polar, hydrogen bonding, pi interactions, or charged interactions with the ligand include Met177, Asn92, Asn184, and Phe185. Additional residues that can potentially make van der Waals interactions with the ligand include Gln152, His143, Phe261, Ala172, His85, Asp170, Lys265, Phe242, Leu245, Thr89, and Phe180.

FIG. 10 shows a summary table of receptor-ligand interactions detailed in FIGS. 3-9. (+) indicates that the ligand elicited a clear dose dependent response from the receptor in vitro; (−) indicates that the ligand did not elicit a response specific, dose dependent response from the receptor in vitro; and shaded cells indicate the interactions detailed in FIGS. 3-9.

DETAILED DESCRIPTION

The presently disclosed subject matter relates to methods for screening and identifying compounds that modulate the activity and/or expression of bitter taste receptors. The presently disclosed subject matter further relates to making palatable, nutritionally-complete pet food products and medicines, wherein the raw materials of the pet food and/or finalized pet food product or medicine is screened to determine if it contains compounds that modulate the bitter taste receptors.

Furthermore, such screening methods can be used to select raw materials and/or finalized pet food products that do not comprise bitter receptor activating compounds. Compounds identified through said methods can be used to modify the palatability of pet food products and medicines by increasing or decreasing a bitter taste. Said compounds can also be used to increase a bitter taste of an object, and thereby reduce palatability and ingestion by a dog.

1. Definitions

The terms used in this specification generally have their ordinary meanings in the art, within the context of this invention and in the specific context where each term is used. Certain terms are discussed below, or elsewhere in the specification, to provide additional guidance to the practitioner in describing the methods and compositions of the invention and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, "taste" refers to a sensation caused by activation of receptor cells in a subject's taste buds. In certain embodiments, taste can be selected from the group consisting of sweet, sour, salt, bitter, kokumi and umami. In certain embodiments, "taste" can include free fatty acid taste. See, e.g., Cartoni et al., J. of Neuroscience, 30(25): 8376-8382 (2010), the contents of which are incorporated herein by reference. In certain embodiments, a taste is elicited in a subject by a "tastant." In certain embodiments, a tastant can be a synthetic tastant. In certain embodiments, the tastant is obtained or prepared from a natural source.

As used herein, "taste profile" refers to a combination of tastes, such as, for example, one or more of a sweet, sour, salt, bitter, umami, kokumi and free fatty acid taste. In certain embodiments, a taste profile is produced by one or more tastant that is present in a composition at the same or different concentrations. In certain embodiments, a taste profile refers to the intensity of a taste or combination of tastes, for example, a sweet, sour, salt, bitter, umami, kokumi and free fatty acid taste, as detected by a subject or any assay known in the art. In certain embodiments, modifying, changing or varying the combination of tastants in a taste profile can change the sensory experience of a subject.

As used herein, "flavor" refers to one or more sensory stimuli, such as, for example, one or more of taste (gustatory), smell (olfactory), touch (tactile) and temperature (thermal) stimuli. In certain non-limiting embodiments, the sensory experience of a subject exposed to a flavor can be classified as a characteristic experience for the particular flavor. For example, a flavor can be identified by the subject as being, but not limited to, a floral, citrus, berry, nutty, caramel, chocolate, peppery, smoky, cheesy, meaty, etc., flavor. As used herein, a flavor composition can be selected from a liquid, solution, dry powder, spray, paste, suspension and any combination thereof. The flavor can be a natural composition, an artificial composition, a nature identical, or any combination thereof.

As used interchangeably herein, "aroma" and "smell" refer to an olfactory response to a stimulus. For example, and not by way of limitation, an aroma can be produced by aromatic substances that are perceived by the odor receptors of the olfactory system.

As used herein, "flavor profile" refers to a combination of sensory stimuli, for example, tastes, such as sweet, sour, bitter, salty, umami, kokumi and free fatty acid tastes, and/or olfactory, tactile and/or thermal stimuli. In certain embodiments, the flavor profile comprises one or more flavors which contribute to the sensory experience of a subject. In certain embodiments, modifying, changing or varying the combination of stimuli in a flavor profile can change the sensory experience of a subject.

As used herein "admixing," for example, "admixing the flavor composition or combinations thereof of the present application with a food product," refers to the process where the flavor composition, or individual components of the flavor composition, is mixed with or added to the completed product or mixed with some or all of the components of the product during product formation or some combination of these steps. When used in the context of admixing, the term "product" refers to the product or any of its components. This admixing step can include a process selected from the step of adding the flavor composition to the product, spraying the flavor composition on the product, coating the flavor composition on the product, suspending the product in the flavor composition, painting the flavor composition on the product, pasting the flavor composition on the product, encapsulating the product with the flavor composition, mixing the flavor composition with the product and any combination thereof. The flavor composition can be a solution, liquid, dry powder, spray, paste, suspension and any combination thereof.

As used herein, "palatability" can refer to the overall willingness of a human or non-human animal, for example, a companion animal, to eat a certain food product. Increasing the "palatability" of a food product can lead to an increase in the enjoyment and acceptance of the food by the human or non-human animal to ensure the human or non-human animal eats a "healthy amount" of the food. Decreasing the "palatability" of a food product can lead to a decrease in the enjoyment and acceptance of the food by the human or non-human animal. The term "healthy amount" of a food as used herein refers to an amount that enables the human or non-human animal to maintain or achieve an intake contributing to its overall general health in terms of micronutrients, macronutrients and calories, for example, such as set out in the "Mars Petcare Essential Nutrient Standards." In certain embodiments, "palatability" can mean a relative preference of a human or non-human animal for one food product over another. For example, when a human or non-human animal shows a preference for one of two or more food products, the preferred food product is more "palatable," and has "enhanced palatability." In certain embodiments, the relative palatability of one food product compared to one or more other food products can be determined, for example, in side-by-side, free-choice comparisons, e.g., by relative consumption of the food products, or other appropriate measures of preference indicative of palatability. Palatability can be determined by a standard testing protocol in which the animal has equal access to both food products such as a test called "two-bowl test" or "versus test." Such preference can arise from any of the animal's senses, but can be related to, inter alia, taste, aftertaste, smell, mouth feel and/or texture.

The term "pet food" or "pet food product" or "final pet food product" means a product or composition that is intended for consumption by a companion animal, such as cats, dogs, guinea pigs, rabbits, birds and horses. For example, but not by way of limitation, the companion animal can be a "domestic" dog, e.g., *Canis lupus familiaris*. In certain embodiments, the companion animal can be a "domestic" cat such as *Felis domesticus*. A "pet food" or "pet food product" includes any food, feed, snack, food supplement, liquid, beverage, treat, toy (chewable and/or consumable toys), meal substitute or meal replacement.

The term "human food" or "human food product" or "final human food product" means a product or composition that is intended for consumption by a human. A "human food" or "human food product" includes any food, feed, snack, food supplement, liquid, beverage, treat, meal substitute or meal replacement.

In certain embodiments, a "food product" includes human and/or pet food products.

As used herein "nutritionally-complete" refers to pet food product that contains all known required nutrients for the intended recipient of the pet food product, in appropriate amounts and proportions based, for example, on recommendations of recognized or competent authorities in the field of companion animal nutrition. Such foods are therefore capable of serving as a sole source of dietary intake to maintain life, without the addition of supplemental nutritional sources.

The term "raw material" means a plant and/or animal material before being processed or manufactured into a final pet food product. In certain embodiments, a "raw material" is not significantly processed in order to separate it into individual elements prior to analysis (e.g., by extraction, purification, fractionation and/or concentration). A "raw material" includes a protein source for a pet food product. In certain embodiments, the raw material is a novel protein source that does not compete with the human food sources (i.e., a protein source that is not commonly eaten by humans). In certain embodiments, the raw material is a by-product of the human food chain. In certain non-limiting embodiments, the "raw material" is processed, for example, in order to separate it into individual elements prior to analysis (e.g., by extraction, purification, fractionation and/or concentration), prior to being analyzed according to the methods described herein.

As used herein "flavor composition" refers to at least one compound or biologically acceptable salt thereof that modulates, including enhancing, multiplying, potentiating, decreasing, suppressing, or inducing, the tastes, smells, flavors and/or textures of a natural or synthetic tastant, flavoring agent, taste profile, flavor profile and/or texture profile in an animal or a human. In certain embodiments, the flavor composition comprises a combination of compounds or biologically acceptable salts thereof. In certain embodiments, the flavor composition includes one or more excipients.

As used herein, "taste deterrent," "taste deterrent product," or "taste deterrent composition" refers to a product or composition containing at least one compound or biologically acceptable salt thereof that provides a bitter taste to an object. In certain embodiments, the taste deterrent discourages an animal from chewing, licking, or consuming an object, for example, a food or liquid product. In certain embodiments, the object is, for example but not limited to, clothing, shoes, carpet, furniture, household items, pesticides, herbicides, or poisonous compounds. In certain embodiments, the object is another animal or the animal itself. In other embodiment, the object is toxic to the animal, or would be detrimental to the animal's health upon ingestion.

As used herein, the terms "modulates" or "modifies" refers to an increase or decrease in the amount, quality or effect of a particular activity of a receptor and/or an increase or decrease in the expression, activity or function of a receptor. "Modulators," as used herein, refer to any inhibitory or activating compounds identified using in silico, in vitro and/or in vivo assays for, e.g., agonists, antagonists, allosteric modulators and their homologs, including fragments, variants and mimetics.

"Inhibitors" or "antagonists," as used herein, refer to modulating compounds that reduce, decrease, block, prevent, delay activation, inactivate, desensitize or down regulate the biological activity and/or expression of a receptor or pathway of interest. The term "antagonist" includes full, partial, and neutral antagonists as well as inverse agonists.

"Inducers," "activators" or "agonists," as used herein, refer to modulating compounds that increase, induce, stimulate, open, activate, facilitate, enhance activation, sensitize or upregulate a receptor or pathway of interest. The term "agonist" includes full and partial agonists.

"Allosteric modulators" as used herein, refer to "positive allosteric modulators" and "negative allosteric modulators." "Positive allosteric modulators" refer to modulating compounds that increase, induce, stimulate, open, activate, facilitate, enhance activation, sensitize or up regulate a receptor or pathway of interest caused by the binding of a different compound to the receptor. "Negative allosteric modulators" refer to modulating compounds that reduce, decrease, block, prevent, delay activation, inactivate, desensitize or down regulate the biological activity and/or expression of a receptor or pathway of interest caused by the binding of a different compound to the receptor.

As used herein, the terms "vector" and "expression vector" refer to DNA molecules that are either linear or circular, into which another DNA sequence fragment of appropriate size can be integrated. Such DNA fragment(s) can include additional segments that provide for transcription of a gene encoded by the DNA sequence fragment. The additional segments can include and are not limited to: promoters, transcription terminators, enhancers, internal ribosome entry sites, untranslated regions, polyadenylation signals, selectable markers, origins of replication and such like. Expression vectors are often derived from plasmids, cosmids, viral vectors and yeast artificial chromosomes. Vectors are often recombinant molecules containing DNA sequences from several sources.

The term "operably linked," when applied to DNA sequences, for example in an expression vector, indicates that the sequences are arranged so that they function cooperatively in order to achieve their intended purposes, i.e., a promoter sequence allows for initiation of transcription that proceeds through a linked coding sequence as far as the termination signal.

The term "nucleic acid molecule" and "nucleotide sequence," as used herein, refers to a single or double stranded covalently-linked sequence of nucleotides in which the 3' and 5' ends on each nucleotide are joined by phosphodiester bonds. The nucleic acid molecule can include deoxyribonucleotide bases or ribonucleotide bases, and can be manufactured synthetically in vitro or isolated from natural sources.

The terms "polypeptide," "peptide," "amino acid sequence" and "protein," used interchangeably herein, refer to a molecule formed from the linking of at least two amino acids. The link between one amino acid residue and the next is an amide bond and is sometimes referred to as a peptide bond. A polypeptide can be obtained by a suitable method known in the art, including isolation from natural sources, expression in a recombinant expression system, chemical synthesis or enzymatic synthesis. The terms can apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid," as used herein, refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate and O-phosphoserine. Amino acid analogs and derivatives can refer to compounds that have the same basic chemical structure as a naturally occurring amino acid, i.e., a carbon that is bound to a hydrogen, a carboxyl group, an amino group and an R group, e.g., homoserine, norleucine, methionine sulfoxide and methionine methyl sulfonium. Such analogs can have modified R groups (e.g., norleucine) or modified peptide backbones, but retain the same basic chemical structure as a naturally occurring amino acid. Amino acid mimetics means chemical compounds that have a structure that is different from the general chemical structure of an amino acid, but that function in a manner similar to a naturally occurring amino acid.

The terms "isolated" or "purified", used interchangeably herein, refers to a nucleic acid, a polypeptide, or other biological moiety that is removed from components with which it is naturally associated. The term "isolated" can refer to a polypeptide that is separate and discrete from the whole organism with which the molecule is found in nature or is present in the substantial absence of other biological macromolecules of the same type. The term "isolated" with respect to a polynucleotide can refer to a nucleic acid molecule devoid, in whole or part, of sequences normally associated with it in nature; or a sequence, as it exists in nature, but having heterologous sequences in association therewith; or a molecule disassociated from the chromosome.

As used herein, the term "recombinant" can be used to describe a nucleic acid molecule and refers to a polynucleotide of genomic, RNA, DNA, cDNA, viral, semisynthetic or synthetic origin which, by virtue of its origin or manipulation is not associated with all or a portion of the polynucleotide with which it is associated in nature.

The term "fusion," as used herein, refers to joining of different peptide or protein segments by genetic or chemical methods wherein the joined ends of the peptide or protein segments may be directly adjacent to each other or may be separated by linker or spacer moieties such as amino acid residues or other linking groups.

2. Bitter Taste Receptors

The presently disclosed subject matter provides bitter taste receptors for use in the disclosed methods. The bitter taste receptors of the present disclosure can include mammalian bitter taste receptors such as, but not limited to, canine bitter taste receptors.

In certain non-limiting embodiments, the bitter taste receptor is a canine bitter taste receptor, for example, canine bitter taste receptor T2R1, T2R2, T2R3, T2R4, T2R5, T2R7, T2R10, T2R12, T2R38, T2R39, T2R40, T2R41, T2R42, T2R43, T2R62, T2R67, or combinations thereof.

In certain embodiments, a bitter taste receptor for use in the presently disclosed methods encompasses a canine bitter taste receptor having the nucleotide sequence set forth in SEQ ID NO:1, 2, 3, 4, 5, 6, 7, 8, 9, 10, 11, 12, 13, 14, 15, or 16 and/or the amino acid sequence set forth in SEQ ID NO:17, 18, 19, 20, 21, 22, 23, 24, 25, 26, 27, 28, 29, 30, 31, or 32, including fragments thereof (e.g., functional fragments thereof) and variants thereof.

In certain non-limiting embodiments, a bitter taste receptor for use in the presently disclosed methods does not include a feline bitter taste receptor.

In certain embodiments, the bitter taste receptor for use in the presently disclosed subject matter can include a receptor encoded by a nucleotide sequence that is at least 85%, at least 90%, at least 91%, at least 92%, at least 93%, at least 94%, at least 95%, at least 96%, at least 97%, at least 98% or at least 99% homologous to any one of SEQ ID NOs:1-16 (homology, as that term is used herein, may be measured using standard software such as BLAST or FASTA).

In certain embodiments, the bitter taste receptor for use in the presently disclosed methods can include a receptor comprising an amino acid sequence that is between about 33 and 99%, between about 34 and 99%, between about 35 and 99%, between about 40 and 99%, between about 45 and 99%, between about 50 and 99%, between about 55 and 99%, between about 60 and 99%, between about 61 and 99%, between about 65 and 99%, between about 70 and 99%, between about 72 and 99%, between about 75 and 99%, between about 79 and 99%, between about 80 and 99%, between about 84 and 99%, between about 85 and 99%, between about 87 and 99%, between about 89 and 99%, between about 90 and 99%, between about 95 and 99%, or between about 97 and 99% homologous to any one of SEQ ID NOs:17-32 (homology, as that term is used herein, may be measured using standard software such as BLAST or FASTA).

In certain embodiments, the bitter taste receptor for use in the presently disclosed methods can include a receptor comprising an amino acid sequence that is at least about 33%, 34%, 35%, 40%, 45%, 50%, 55%, 60%, 61%, 65%, 70%, 72%, 75%, 79%, 80%, 84%, 85%, 87%, 89%, 90%, 91%, 92%, 93%, 94%, 95%, 96%, 97%, 98%, or 99% homologous to any one of SEQ ID NOs:17-32 (homology, as that term is used herein, may be measured using standard software such as BLAST or FASTA).

In certain embodiments, the bitter taste receptor is a canine T2R1 comprising an amino acid sequence as set forth in SEQ ID NO:17, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:1, or a sequence at least 99, 98, 97, 96, 95, 90, 85 or 80 percent homologous thereto (homology, as that term is used herein, may be measured using standard software such as BLAST or FASTA).

In certain embodiments, the bitter taste receptor is a canine T2R2 comprising an amino acid sequence as set forth in SEQ ID NO:18, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:2, or a sequence at least 99, 98, 97, 96, 95, 90, 85 or 80 percent homologous thereto (homology, as that term is used herein, may be measured using standard software such as BLAST or FASTA).

In certain embodiments, the bitter taste receptor is a canine T2R3 comprising an amino acid sequence as set forth in SEQ ID NO:19, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:3, or a sequence at least 99, 98, 97, 96, 95, 90, 85 or 80 percent homologous thereto (homology, as that term is used herein, may be measured using standard software such as BLAST or FASTA).

In certain embodiments, the bitter taste receptor is a canine T2R4 comprising an amino acid sequence as set forth in SEQ ID NOs:20, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:4, or a sequence at least 99, 98, 97, 96, 95, 90, 85 or 80 percent homologous thereto (homology, as that term is used herein, may be measured using standard software such as BLAST or FASTA).

In certain embodiments, the bitter taste receptor is a canine T2R5 comprising an amino acid sequence as set forth in SEQ ID NO:21, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:5, or a sequence at least 99, 98, 97, 96, 95, 90, 85 or 80 percent homologous thereto (homology, as that term is used herein, may be measured using standard software such as BLAST or FASTA).

In certain embodiments, the bitter taste receptor is a canine T2R7 comprising an amino acid sequence as set forth in SEQ ID NO:22, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:6, or a sequence at least 99, 98, 97, 96, 95, 90, 85 or 80 percent homologous thereto (homology, as that term is used herein, may be measured using standard software such as BLAST or FASTA).

In certain embodiments, the bitter taste receptor is a canine T2R10 comprising an amino acid sequence as set forth in SEQ ID NO:23, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:7, or a sequence at least 99, 98, 97, 96, 95, 90, 85 or 80 percent homologous thereto (homology, as that term is used herein, may be measured using standard software such as BLAST or FASTA).

In certain embodiments, the bitter taste receptor is a canine T2R12 comprising an amino acid sequence as set forth in SEQ ID NO:24, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:8, or a sequence at least 99, 98, 97, 96, 95, 90, 85 or 80 percent homologous thereto (homology, as that term is used herein, may be measured using standard software such as BLAST or FASTA).

In certain embodiments, the bitter taste receptor is a canine T2R38 comprising an amino acid sequence as set forth in SEQ ID NO:25, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:9, or a sequence at least 99, 98, 97, 96, 95, 90, 85 or 80 percent homologous thereto (homology, as that term is used herein, may be measured using standard software such as BLAST or FASTA).

In certain embodiments, the bitter taste receptor is a canine T2R39 comprising an amino acid sequence as set forth in SEQ ID NO:26, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:10, or a sequence at least 99, 98, 97, 96, 95, 90, 85 or 80 percent homologous thereto (homology, as that term is used herein, may be measured using standard software such as BLAST or FASTA).

In certain embodiments, the bitter taste receptor is a canine T2R40 comprising an amino acid sequence as set forth in SEQ ID NO:27, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:11, or a sequence at least 99, 98, 97, 96, 95, 90, 85 or 80 percent homologous thereto (homology, as that term is used herein, may be measured using standard software such as BLAST or FASTA).

In certain embodiments, the bitter taste receptor is a canine T2R41 comprising an amino acid sequence as set forth in SEQ ID NO:28, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:12, or a sequence at least 99, 98, 97, 96, 95, 90, 85 or 80 percent homologous thereto (homology, as that term is used herein, may be measured using standard software such as BLAST or FASTA).

In certain embodiments, the bitter taste receptor is a canine T2R42 comprising an amino acid sequence as set forth in SEQ ID NO:29, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:13, or a sequence at least 99, 98, 97, 96, 95, 90, 85 or 80 percent homologous thereto (homology, as that term is used herein, may be measured using standard software such as BLAST or FASTA).

In certain embodiments, the bitter taste receptor is a canine T2R43 comprising an amino acid sequence as set forth in SEQ ID NO:30, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:14, or a sequence at least 99, 98, 97, 96, 95, 90, 85 or 80 percent homologous thereto (homology, as that term is used herein, may be measured using standard software such as BLAST or FASTA).

In certain embodiments, the bitter taste receptor is a canine T2R62 comprising an amino acid sequence as set forth in SEQ ID NO:31, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:15, or a sequence at least 99, 98, 97, 96, 95, 90, 85 or 80 percent homologous thereto (homology, as that term is used herein, may be measured using standard software such as BLAST or FASTA).

In certain embodiments, the bitter taste receptor is a canine T2R67 comprising an amino acid sequence as set forth in SEQ ID NO:32, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:16, or a sequence at least 99, 98, 97, 96, 95, 90, 85 or 80 percent homologous thereto (homology, as that term is used herein, may be measured using standard software such as BLAST or FASTA).

In certain embodiments, homology is described as a percent identity between two sequences. The percent identity of two amino acid sequences or of two nucleotide sequences can be determined by aligning the sequences for optimal comparison purposes (e.g., gaps can be introduced in the first sequence for best alignment with the sequence) and comparing the amino acid residues or nucleotides at corresponding positions. The percent identity can be determined by the number of identical amino acid residues or nucleotides in the sequences being compared (e.g., % identity=number of identical positions/total number of positions×100).

The determination of percent identity between two sequences can be determined using a mathematical algorithm known to those of skill in the art. A non-limiting example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877, the disclosures of which are incorporated herein by reference in their entireties. The NBLAST and XBLAST programs of Altschul, et al. (1990) J. Mol. Biol. 215:403-410 have incorporated such an algorithm. BLAST nucleotide searches can be performed with the NBLAST program, for example, score=100, wordlength=12, to obtain nucleotide sequences homologous to nucleotide sequences of the invention. BLAST protein searches can be performed with the XBLAST program, for example, score=50, wordlength=3, to obtain amino acid sequences homologous to amino acid sequence of the invention. To obtain gapped alignments for comparison purposes, Gapped BLAST can be utilized as described in Altschul et al. (1997) Nucleic Acids Res. 25:3389-3402, the disclosure of which is incorporated herein by reference in its entirety. Alternatively, PSI-Blast can be used to perform an iterated search, which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. An additional non-limiting example of a mathematical algorithm utilized for the comparison of sequences is the algorithm of Myers and Miller, CABIOS (1989), the disclosure of which is incorporated herein by reference in its entirety. The ALIGN program (version 2.0), which is part of the CGC sequence alignment software package, has incorporated such an algorithm. Other non-limiting examples of algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8, the disclosures of which are incorporated herein by reference in their entireties. Within FASTA, ktup is a control option that sets the sensitivity and speed of the search.

In certain embodiments, the disclosed subject matter provides for the use of an isolated or purified bitter taste receptor and/or variants and fragments thereof. The disclosed subject matter also encompasses the use of sequence variants. In certain embodiments, variation can occur in either or both the coding and non-coding regions of a nucleotide sequence of a bitter taste receptor. Variants can include a substantially homologous protein encoded by the same genetic locus in an organism, i.e., an allelic variant. Variants also encompass proteins derived from other genetic loci in an organism, e.g., canine, but having substantial homology to the bitter taste receptor, i.e., a homolog. Variants can also include proteins substantially homologous to the bitter taste receptor but derived from another organism, i.e., an ortholog. Variants also include proteins that are substantially homologous to the bitter taste receptor that are produced by chemical synthesis. Variants also include proteins that are substantially homologous to the bitter taste receptor that are produced by recombinant methods.

Orthologs, homologs and allelic variants can be identified using methods well known in the art. These variants can include a nucleotide sequence encoding a receptor that is at least about 60-65%, about 65-70%, about 70-75, about 80-85%, about 90-95%, about 95-99% or more homologous to the nucleotide sequence shown in any one of SEQ ID NOs:1-16, or fragments thereof. Such nucleic acid molecules can readily be identified as being able to hybridize under stringent conditions, to the nucleotide sequence shown in any one of SEQ ID NOs:1-16, or a fragment thereof. In certain embodiments, two polypeptides (or regions thereof) are substantially homologous when the amino acid sequences are at least about 60-65%, about 65-70%, about 70-75, about 80-85%, about 90-95%, about 95-99% or more homologous to the amino acid sequences shown in any one of SEQ ID NOs:17-32, or a fragment thereof. A substantially homologous amino acid sequence, according to the disclosed subject matter, will be encoded by a nucleic acid sequence hybridizing to the nucleic acid sequence, or portion thereof, of the nucleotide sequence shown in any one of SEQ ID NOs:1-16 under stringent conditions.

The bitter taste receptors for use in the methods of the disclosed subject matter include bitter taste receptors having additions, deletions or substitutions of amino acid residues (variants) which do not substantially alter the biological activity of the receptor. Those individual sites or regions of the bitter taste receptors which may be altered without affecting biological activity can be determined by examination of the structure of the bitter taste receptor extracellular domain, for example. Alternatively and/or additionally, one can empirically determine those regions of the receptor which would tolerate amino acid substitutions by alanine scanning mutagenesis (Cunningham et al., Science 244, 1081-1085 (1989), the disclosure of which is hereby incorporated by reference in its entirety). In the alanine scanning mutagenesis method, selected amino acid residues are individually substituted with a neutral amino acid (e.g., alanine) in order to determine the effects on biological activity.

It is generally recognized that conservative amino acid changes are least likely to perturb the structure and/or function of a polypeptide. Accordingly, the disclosed subject matter encompasses one or more conservative amino acid changes within a bitter taste receptor. Conservative amino acid changes generally involve substitution of one amino acid with another that is similar in structure and/or function (e.g., amino acids with side chains similar in size, charge and shape). Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a bitter taste receptor can be replaced with other amino acid residues from the same side chain family and the altered protein can be tested for retained function using the functional assays described herein. Modifications can be introduced into a bitter taste receptor of the present disclosure by standard techniques known in the art, such as site-directed mutagenesis and PCR-mediated mutagenesis. If such substitutions result in a retention in biological activity, then more substantial changes can be introduced and/or other additions/deletions may be made and the resulting products screened. In certain embodiments, deletions or additions can be from 5-10 residues, alternatively from 2-5 amino acid residues or from 1-2 residues, and values in between.

The disclosed subject matter also provides for fusion proteins that comprise a bitter taste receptor, or fragment thereof. In certain embodiments, the disclosed subject matter provides for fusion proteins of a bitter taste receptor, or functional fragments thereof, and an immunoglobulin heavy chain constant region. In certain embodiments, a fusion protein of the present disclosure can include a detectable marker, a functional group such as a carrier, a label, a stabilizing sequence or a mechanism by which bitter taste receptor agonist binding can be detected. Non-limiting embodiments of a label include a FLAG tag, a His tag, a MYC tag, a maltose binding protein and others known in the art. The presently disclosed subject matter also provides nucleic acids encoding such fusion proteins, vectors containing fusion protein-encoding nucleic acids and host cells comprising such nucleic acids or vectors. In certain embodiments, fusions can be made at the amino terminus (N-terminus) of a bitter taste receptor or at the carboxy terminus (C-terminus) of a bitter taste receptor.

In certain embodiments, the bitter taste receptors disclosed herein can contain additional amino acids at the N-terminus and/or at the C-terminus end of the sequences, e.g., when used in the methods of the disclosed subject matter. In certain embodiments, the additional amino acids can assist with immobilizing the polypeptide for screening purposes, or allow the polypeptide to be part of a fusion protein, as disclosed above, for ease of detection of biological activity.

3. Methods for Identifying Bitter Taste Receptor Modulating Compounds

The present disclosure further provides methods for identifying compounds that modulate the activity and/or expression of a bitter taste receptor. For example, and not by way of limitation, the modulator can be an agonist (for example, a full or partial agonist), or an antagonist, or an inverse agonist, or an allosteric modulator. The presently disclosed subject matter provides in silico and in vitro methods for identifying compounds that modulate the activity and/or expression of a bitter taste receptor, disclosed above.

3.1 In Silico Methods

The presently disclosed subject matter further provides in silico methods for identifying compounds that can potentially interact with a bitter taste receptor and/or modulate the activity and/or expression of a bitter taste receptor.

In certain embodiments, the method can include predicting the three-dimensional structure (3D) of a bitter taste receptor and screening the predicted 3D structure with putative bitter taste receptor modulating compounds (i.e., test compounds). The method can further include predicting whether the putative compound would interact with the binding site of the receptor by analyzing the potential interactions with the putative compound and the amino acids of the receptor. The method can further include identifying a test compound that can bind to and/or modulate the biological activity of the bitter taste receptor by determining whether the 3D structure of the compound fits within the binding site of the 3D structure of the receptor.

In certain embodiments, the bitter taste receptor for use in the disclosed method can be a canine T2R1, T2R2, T2R3, T2R4, T2R5, T2R7, T2R10, T2R12, T2R38, T2R39, T2R40, T2R41, T2R42, T2R43, T2R62, T2R67, or combinations thereof.

In other embodiments, the bitter taste receptor for use in the disclosed method can have the amino acid sequence of any one of SEQ ID NO:17-32, or a fragment or variant thereof. In certain embodiments, the bitter taste receptor for use in the presently disclosed subject matter can include a receptor comprising an amino acid sequence having at least about 33%, 34%, 35%, 40%, 45%, 50%, 55%, 60%, 61%, 65%, 70%, 72%, 75%, 79%, 80%, 84%, 85%, 87%, 89%, 90%, 91%, 92%, 93%, 94%, 95%, 96%, 97%, 98%, or 99% identity to any one of SEQ ID NO:17-32, or a fragment or variant thereof. In certain embodiments, the bitter taste receptor for use in the disclosed method can be encoded by a nucleotide sequence of any one of SEQ ID NO:1-16, or a fragment or variant thereof. In certain embodiments, the bitter taste receptor for use in the presently disclosed subject matter can include a receptor encoded by a nucleotide sequence having at least 85%, at least 90%, at least 91%, at least 92%, at least 93%, at least 94%, at least 95%, at least 96%, at least 97%, at least 98% or at least 99% identity to any one of SEQ ID NO:1-16, or a fragment or variant thereof.

Non-limiting examples of compounds (e.g., potential bitter taste receptor modulators) that can be tested using the disclosed methods include any small chemical compound, or any biological entity, such as peptides, salts, amino acids and bitter compound known in the art, e.g. denatonium benzoate. In certain embodiments, the test compound can be a small chemical molecule.

In certain embodiments, structural models of a bitter taste receptor can be built using crystal structures of other GPCRs as templates for homology modeling. For example, and not by way of limitation, structural models can be generated using the crystal structures of Group 1 GPCRs. Bitter receptors belong to a separate subclass of GPCR's for which crystal structures have not been solved yet. In certain embodiments, a structural model of a bitter taste receptor can be based on a known or a combination of known crystal structures of GPCRs. (See, e.g., Lee et al., Eur J Pharmacol. 2015 May 14. pii: S0014-2999(15)30012-1, which is incorporated by reference in its entirety herein). In certain embodiments, a structural model of a bitter taste receptor can be generated based on the crystal structure of a β2 adrenergic receptor, 3SN6 from Protein Data Bank (PDB). (See, e.g., Rasmussen et al., Nature. 2011 Jul. 19; 477 (7366):549-55, which is incorporated by reference in its entirety herein). In certain embodiments, a structural model of the 7 transmembrane domain (7TM) of a bitter taste receptor can be generated based on the crystal structures of existing GPCR crystal structure 3 SN6 from PDB.

Any suitable modeling software known in the art can be used. In certain embodiments, the Modeller software package can be used to generate the three-dimensional protein structure.

In certain embodiments, the in silico methods of identifying a compound that binds to a T2R comprises determining whether a test compound interacts with one or more amino acids of a T2R binding pocket, as described herein.

Compounds that are identified by the disclosed in silico methods can be further tested using the in vitro and in vivo methods disclosed herein.

3.2 T2R Transmembrane Compound Binding Site

The present application provides for methods of screening for compounds that modulate the activity of a bitter taste receptor, for example, a canine T2R receptor, wherein the compounds interact with one or more amino acids of the bitter taste receptor. In certain embodiments, the binding site of a bitter taste receptor comprises amino acids within the 7TM domain of the receptor, and can be identified by generating an interaction map of the receptor using in silico modeling, as described herein. In one non-limiting example, the presence of an amino acid in the 7TM interaction map means that the residue is in the vicinity of the ligand binding environment, an interacts with the ligand.

In certain embodiments, the interaction between an amino acid in the 7TM interaction map and the ligand is a pi-pi interaction.

In certain embodiments, the interaction between an amino acid in the 7TM interaction map and the ligand is a hydrogen bond interaction.

In certain embodiments, the interaction between an amino acid in the 7TM interaction map and the ligand is a hydrophobic interaction.

In certain embodiments, the interaction between an amino acid in the 7TM interaction map and the ligand is a van de Waals interaction.

In certain embodiments, the amino acid in the 7TM interaction map is a polar amino acid, wherein the amino acid interacts with the ligand as a hydrogen bond donor and/or acceptor.

In certain embodiments, the interaction between a compound and one or more amino acids of the T2R receptors described herein can comprises one or more hydrogen bond, covalent bond, non-covalent bond, salt bridge, physical interaction, and combinations thereof. The interactions can also be any interaction characteristic of a ligand receptor interaction known in the art. Such interactions can be determined by, for example, site directed mutagenesis, x-ray crystallography, x-ray or other spectroscopic methods, Nuclear Magnetic Resonance (NMR), cross-linking assessment, mass spectroscopy or electrophoresis, cryo-microscopy, displacement assays based on known agonists, structural determination and combinations thereof. In certain embodiments, the interactions are determined in silico, for example, by theoretical means such as docking a compound into a canine T2R binding pocket using molecular docking, molecular modeling, molecular simulation, or other means known to persons of ordinary skill in the art. In certain embodiments, the T2R receptor is a canine T2R, for example, but not limited to, T2R1, T2R2, T2R3, T2R4, T2R5, T2R7, T2R10, T2R12, T2R38, T2R39, T2R40, T2R41, T2R42, T2R43, T2R62, and T2R67.

In certain embodiments, the T2R is a T2R present in canine but not present in feline animals, for example, T2R5, T2R39, T2R40, T2R41, and/or T2R62.

In certain embodiments, the compounds interact with one or more T2R receptors described herein according to any combination of interactions described herein, for example, one, two, three or more of the interactions.

In certain embodiments, the compounds bind to at least one of the receptors described herein. In certain embodiment, the compounds bind selectively to only one of the receptors described herein.

In one embodiment, the bitter taste receptor is a canine T2R1. In certain embodiments, the amino acids that the compounds interact with comprise Asn89 and/or Tyr239, for example, by polar or hydrogen bonding, as exemplified by in silico modeling of Menthol in T2R1 (FIG. 3). Alternatively, or in addition, in certain embodiments, the amino acids that the compounds interact with comprise any one, two, three or more of the T2R1 residues Asn89, Tyr239, Ile167, Gln174, Glu169, Phe257, Ala242, Phe177, His238, Cys260, Phe264, Leu234, Cys235, Phe85, Leu261, Leu178, Leu181, Val86, and Phe82, for example, by polar, hydrogen bond, salt bridge, van der Waals, pi, or other interactions, as exemplified by in silico modeling of Menthol in T2R1 (FIG. 3).

In one embodiment, the bitter taste receptor is a canine T2R2, which is shared by dogs and cats, but not humans, where it is a pseudogene. In certain embodiments, the amino acids that the compounds interact with comprise one or more of T2R2 residues Ser94, Trp90, Lys268, Tyr245, and/or Glu180, for example, by hydrogen bonding or salt bridge interactions, as exemplified by in silico modeling of Ofloxacin in T2R2 (FIG. 4). Alternatively, or in addition, in certain embodiments, the amino acids that the compounds interact with comprise T2R2 residues Arg176 and/or Met91, either alone or in conjunction with interactions listed above, for example, by polar, hydrogen bonding, or charged interactions, as exemplified by in silico modeling of Ofloxacin in T2R2 (FIG. 4). Alternatively, or in addition, in certain embodiments, the amino acids that the compounds interact with comprise any one, two, three or more of the T2R2 residues Ser94, Trp90, Lys268, Tyr245, Glu180, Arg176, Met91, Asn185, Val184, Met181, Phe249, Pro155, Gln177, Lys174, Phe264, Phe93, Leu59, Met271, Phe246, and Leu188, for example, by polar, hydrogen bond, salt bridge, van der Waals, pi, or other interactions, as exemplified by in silico modeling of Ofloxacin in T2R2 (FIG. 4).

In one embodiment, the bitter taste receptor is a canine T2R3. In certain embodiments, the amino acids that the compounds interact with comprise T2R3 residues Asn93 and/or Asp86, for example, by hydrogen bonding or salt bridge interactions, as exemplified by in silico modeling of Chloroquine in T2R3 (FIG. 5). Alternatively, or in addition, in certain embodiments, the amino acids that the compounds interact with comprise any one or more of the T2R3 residues Tyr246, Phe247, Thr186, Asn189, Trp89, Asp86, and Arg175, either alone or in conjunction with interactions listed above, for example, by polar, hydrogen bonding, or charged interactions, as exemplified by in silico modeling of Chloroquine in T2R3 (FIG. 5). Alternatively, or in addition, in certain embodiments, the amino acids that the compounds interact with comprise any one, two, three or more of the T2R3 residues Asn93, Asp86, Tyr246, Phe247, Thr186, Asn189, Trp89, Asp86, Arg175, Phe250, Gly185, Phe243, Thr90, Asn176, Val149, Ile154, Lys174, Met82, Ile85, Lys173, and Met69, for example, by polar, hydrogen bond, salt bridge, van der Waals, pi, or other interactions, as exemplified by in silico modeling of Chloroquine in T2R3 (FIG. 5).

In one embodiment, the bitter taste receptor is a canine T2R4. In certain embodiments, the amino acids that the compounds interact with comprise any one or more of T2R4 residues Ser186, Asp93, and Tyr240, for example, by hydrogen bonding or salt bridge interactions, as exemplified by in silico modeling of Colchicine in T2R4 (FIG. 6). Alternatively, or in addition, in certain embodiments, the amino acids that the compounds interact with comprise any one or more of T2R4 residues Ser94, Leu97, Asn95, Leu92, Ser96, Trp98, Val187, and Thr247, either alone or in conjunction with interactions listed above, for example, by polar, hydrogen bonding, or charged interactions, as exemplified by in silico modeling of Colchicine in T2R4 (FIG. 6). Alternatively, or in addition, in certain embodiments, the amino acids that the compounds interact with comprise any one, two, three or more of the T2R4 residues Ser186, Asp93, Tyr240, Ser94, Leu97, Asn95, Leu92, Ser96, Trp98, Val187, Thr247, Tyr243, Trp89, Met58, Ser269, Pro273, Ser270, Gln189, Thr144, Leu188, Val183, Leu182, Ser244, and Met90, for example, by polar, hydrogen bond, salt bridge, van der Waals, pi, or other interactions, as exemplified by in silico modeling of Colchicine in T2R4 (FIG. 6).

In one embodiment, the bitter taste receptor is a canine T2R5, which is present in dogs and humans, but not cats. In certain embodiments, the amino acids that the compounds interact with comprise T2R5 residue Ser89, for example, by hydrogen bonding or salt bridge interactions, as exemplified by in silico modeling of 1,10 Phenanthroline in T2R5 (FIG. 7). Alternatively, or in addition, in certain embodiments, the amino acids that the compounds interact with comprise any one, two, three or more of the T2R5 residues Ser89, Pro264, Leu58, Val88, Gln90, Ile86, Leu173, Trp165, Thr258, Ala261, Tyr234, Glu257, Met260, and Trp85, for example, by polar, hydrogen bond, salt bridge, van der Waals, pi, or other interactions, as exemplified by in silico modeling of 1,10 Phenanthroline in T2R5 (FIG. 7).

In one embodiment, the bitter taste receptor is a canine T2R10. In certain embodiments, the amino acids that the compounds interact with comprise T2R10 residues Lys258 and/or Leu180 (backbone), for example, by hydrogen bonding or salt bridge interactions, as exemplified by in silico modeling of Cucurbitacin B in T2R10 (FIG. 8). Alternatively, or in addition, in certain embodiments, the amino acids that the compounds interact with comprise one or more of T2R10 residues Lys170, Glu172, and Asn181, either alone or in conjunction with interactions listed above, for example, by polar, hydrogen bonding, or charged interactions, as exemplified by in silico modeling of Cucurbitacin B in T2R10 (FIG. 8). Alternatively, or in addition, in certain embodiments, the amino acids that the compounds interact with comprise any one, two, three or more of the T2R10 residues Lys258, Leu180, Lys170, Glu172, Asn181, Phe261, Met265, Ile262, Gln169, Lys69, Met168, Ile245, Val90, Phe242, Gln94, Val184, Asn93, Trp89, and Tyr241, for example, by polar, hydrogen bond, salt bridge, van der Waals, pi, or other interactions, as exemplified by in silico modeling of Cucurbitacin B in T2R10 (FIG. 8).

In one embodiment, the bitter taste receptor is a canine T2R43. In certain embodiments, the amino acids that the compounds interact with comprise one or more of T2R43 residues Tyr241, Trp88, and Thr181, for example, by hydrogen bonding interactions, as exemplified by in silico modeling of Propylthiouracil in T2R43 (FIG. 9). Alternatively, or in addition, in certain embodiments, the amino acids that the compounds interact with comprise one or more of T2R43 residues Met177, Asn92, Asn184, and Phe185, either alone or in conjunction with interactions listed above, for example, by polar or hydrogen bonding interactions, as exemplified by in silico modeling of Propylthiouracil in T2R43 (FIG. 9). Alternatively, or in addition, in certain embodiments, the amino acids that the compounds interact with comprise any one, two, three or more of the T2R43 residues Tyr241, Trp88, Thr181, Met177, Asn92, Asn184, Phe185, Gln152, His143, Phe261, Ala172, His85, Asp170, Lys265, Phe242, Leu245, Thr89, and Phe180, for example, by polar, hydrogen bond, salt bridge, van der Waals, pi, or other interactions, as exemplified by in silico modeling of Propylthiouracil in T2R43 (FIG. 9).

In certain embodiments, the compounds interact with any one or more of the canine T2R receptors described herein, wherein the compounds interact with one or more amino acid residues present in the 7TM domains of said receptors. The EC2 loop of said receptors is at the entrance to the active site pocket of the receptors. In certain embodiments, amino acid residues present in the EC2 loop of the bitter receptors interact with the compounds described herein.

3.3 In Vitro Methods

The presently disclosed subject matter further provides in vitro methods for identifying raw materials for generating pet food, food products, or compounds that can modulate the activity and/or expression of a bitter taste receptor.

Bitter taste receptors for use in the presently disclosed methods can include isolated or recombinant bitter taste receptors or cells expressing a bitter taste receptor, disclosed herein. In certain embodiments, the bitter taste receptor for use in the disclosed methods can comprise the amino acid sequence of any one of SEQ ID NO:17-32, or a fragment or variant thereof. In certain embodiments, the bitter taste receptor for use in the disclosed method can have at least about 33%, 34%, 35%, 40%, 45%, 50%, 55%, 60%, 61%, 65%, 70%, 72%, 75%, 79%, 80%, 84%, 85%, 87%, 89%, 90%, 91%, 92%, 93%, 94%, 95%, 96%, 97%, 98%, or 99% identity to the amino acid sequence of any one of SEQ ID NO:17-32, or a fragment or variant thereof. In certain embodiments, the bitter taste receptor for use in the disclosed method can be encoded by a nucleotide sequence comprising any one of SEQ ID NO:1-16, or a fragment or variant thereof. In certain embodiments, the bitter taste receptor for use in the presently disclosed subject matter can include a receptor encoded by a nucleotide sequence having at least 85%, at least 90%, at least 91%, at least 92%, at least 93%, at least 94%, at least 95%, at least 96%, at least 97%, at least 98% or at least 99% identity to any one of SEQ ID NO:1-16, or a fragment or variant thereof.

In certain embodiments, the method for identifying compounds that modulate the activity and/or expression of a bitter taste receptor comprises measuring the biological activity of a bitter taste receptor in the absence and/or presence of a test compound. In certain embodiments, the method can include measuring the biological activity of a bitter taste receptor in the presence of varying concentrations of the test compound. The method can further include identifying the test compounds that result in a modulation of the activity and/or expression of the bitter taste receptor compared to the activity and/or expression of the bitter taste receptor in the absence of the test compound.

In certain embodiments, the method can further include analyzing two or more, three or more or four or more test compounds in combination. In certain embodiments, the two or more, three or more or four or more test compounds can be from different classes of compounds, e.g., amino acids and small chemical compounds. For example, and not by way of limitation, the method can include analyzing the effect of one or more small chemical test compounds on the biological activity and/or expression of a bitter taste receptor in the presence of one or more amino acid test compounds. In certain embodiments, the method for identifying the effect of a compound on the activity and/or expression of a bitter taste receptor comprises analyzing the effect of a test compound on the biological activity and/or expression of a bitter taste receptor in the presence of a bitter taste receptor ligand, for example, a bitter tastant or bitter receptor agonist.

In certain embodiments, the method for identifying compounds that can modulate the activity and/or expression of a bitter taste receptor comprises expressing a bitter taste receptor in a cell line and measuring the biological activity of the receptor in the presence and/or absence of a test compound. The method can further comprise identifying test compounds that modulate the activity of the receptor by determining if there is a difference in receptor activation in the presence of a test compound compared to the activity of the receptor in the absence of the test compound. In certain embodiments, the method can include measuring the biological activity of the bitter taste receptor in the presence of varying concentrations of the test compound. In certain embodiments, the selectivity of the putative bitter taste receptor modulator can be evaluated by comparing its effects on other GPCRs or taste receptors, e.g., umami, fatty acid, kokumi (CaSR), T1R, etc. receptors.

In certain embodiments, the compounds identified according to the methods described herein increase or decrease the biological activity of a bitter taste receptor by at least about 5%, 10%, 15%, 20%, 25%, 30%, 35%, 40%, 45%, 50%, 55%, 60%, 65%, 70%, 75%, 80%, 85%, 90%, 95%, 100%, or more, compared to the biological activity of the bitter taste receptor when the compound is not present.

In certain embodiments, the method for identifying compounds that modulate the activity and/or expression of a bitter taste receptor comprises determining whether a compound modulates the receptor directly, for example, as an agonist or antagonist. In certain embodiments, the method comprises determining whether a compound indirectly modulates the activity of the receptor (e.g., as an allosteric modulator), for example, by enhancing or decreasing the effect of other compounds on activating or inhibiting receptor activity.

Activation of the receptor in the presently disclosed methods can be detected through the use of a labelling compound and/or agent. In certain embodiments, the activity of the bitter taste receptor can be determined by the detection of secondary messengers such as, but not limited to, cAMP, cGMP, IP3, DAG or calcium. In certain embodiments, the activity of the bitter taste receptor can be determined by the detection of the intracellular calcium levels. Monitoring can be by way of, but not limited to, luminescence or fluorescence detection, such as by a calcium sensitive fluorescent dye or luminescent photoprotein. In certain embodiments, monitoring can be by way of luminescence. In certain embodiments, the intracellular calcium levels can be determined using a cellular dye, e.g., a fluorescent calcium indicator such as Calcium 4. In certain embodiments, the intracellular calcium levels can be determined by measuring the level of calcium binding to a calcium-binding protein, for example, calmodulin. Alternatively and/or additionally, the activity of the bitter taste receptor can be determined by the detection of the phosphorylation, transcript levels and/or protein levels of one or more downstream protein targets of the bitter taste receptor.

The cell line used in the presently disclosed methods can include any cell type that is capable of expressing a bitter taste receptor (e.g., stable or transient expression). Non-limiting examples of cells that can be used in the disclosed methods include HeLa cells, Chinese hamster ovary cells (CHO cells), African green monkey kidney cells (COS cells), *Xenopus* oocytes, HEK-293 cells and murine 3T3 fibroblasts. In certain embodiments, the method can include expressing a bitter taste receptor in HEK-293 cells. In certain embodiments, the method can include expressing a bitter taste receptor in COS cells. In certain embodiments, the cells constitutively express the bitter taste receptor. In certain embodiments, the cells transiently express the bitter taste receptor. In another embodiment, expression of the bitter taste receptor by the cells is inducible.

In certain embodiments, the cell expresses a calcium-binding photoprotein, wherein the photoprotein luminesces upon binding calcium. In certain embodiments, the calcium binding photoprotein comprises the protein clytin. In certain embodiments the clytin is a recombinant clytin. In certain embodiments, the clytin comprises an isolated clytin, for example, a clytin isolated from *Clytia gregarium*. In certain embodiments, the calcium-binding photoprotein comprises the protein aequorin, for example, a recombinant aequorin or an isolated aequorin, such as an aequorin isolated from *Aequorea victoria*. In certain embodiments, the calcium-binding photoprotein comprises the protein obelin, for example, a recombinant obelin or an isolated obelin, such as an obelin isolated from *Obelia longissima.*

In certain embodiments, expression of a bitter taste receptor in a cell can be performed by introducing a nucleic acid encoding a bitter taste receptor into the cell. For example, and not by way of limitation, a nucleic acid having the nucleotide sequence set forth in any one of SEQ ID NO: 1-16, or a fragment thereof, can be introduced into a cell. In certain embodiments, the introduction of a nucleic acid into a cell can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92 (1985), the disclosures of which are hereby incorporated by reference in their entireties) and can be used in accordance with the disclosed subject matter. In certain embodiments, the technique can provide for the stable transfer of the nucleic acid to the cell, so that the nucleic acid is expressible by the cell and inheritable and expressible by its progeny. In certain embodiments, the technique can provide for a transient transfer of the nucleic acid to the cell, so that the nucleic acid is expressible by the cell, wherein the concentration of the nucleic acid and the expression decrease in subsequent generations of the cell's progeny.

In certain embodiments, the methods can include identifying compounds that bind to a bitter taste receptor. The methods can comprise contacting a bitter taste receptor with a test compound and measuring binding between the compound and the bitter taste receptor. For example, and not by way of limitation, the methods can include providing an isolated or purified bitter taste receptor in a cell-free system, and contacting the receptor with a test compound in the cell-free system to determine if the test compound binds to the bitter taste receptor. In certain embodiments, the method can comprise contacting a bitter taste receptor expressed on the surface of a cell with a candidate compound and detecting binding of the candidate compound to the bitter taste receptor. The binding can be measured directly, e.g., by using a labeled test compound, or can be measured indirectly. In certain embodiments, the detection comprises detecting a physiological event in the cell caused by the binding of the compound to the bitter taste receptor, e.g., an increase in the intracellular calcium levels. For example, and not by way of limitation, detection can be performed by way of fluorescence detection, such as a calcium sensitive fluorescent dye, by detection of luminescence, or any other method of detection known in the art.

In other non-limiting embodiments, the in vitro assay comprises cells expressing a bitter receptor that is native to the cells. Examples of such cells expressing a native bitter receptor include, for example but not limited to, dog and/or cat taste cells (e.g., primary taste receptor cells). In certain embodiments, the dog and/or cat taste cells expressing a bitter receptor are isolated from a dog and/or cat and cultured in vitro. In certain embodiments, the taste receptor cells can be immortalized, for example, such that the cells isolated from a dog and/or cat can be propagated in culture.

In certain embodiments, expression of a bitter taste receptor in a cell can be induced through gene editing, for example, through use of the CRISPR gene editing system to incorporate a bitter taste receptor gene into the genome of a cell, or to edit or modify a bitter taste receptor gene native to the cell.

In certain embodiments, the in vitro methods of identifying a compound that binds to a T2R comprises determining whether a test compound interacts with one or more amino acids of a T2R binding pocket, as described herein.

In certain embodiments, compounds identified as modulators of a bitter taste receptor can be further tested in other analytical methods including, but not limited to, in vivo assays, to confirm or quantitate their modulating activity.

In certain embodiments, the methods of identifying a bitter taste receptor modulator can comprise comparing the effect of a test compound to a bitter taste receptor agonist or antagonist. For example, a test compound that increases or decreases the activity of the receptor in the presence of an agonist when compared to the activity of the receptor when contacted with a bitter taste receptor agonist alone can be selected as a bitter taste receptor modulating compound.

Bitter receptor agonists that can be used according to said methods can comprise one or more compounds described by Table 1.

TABLE 1
| Canine Bitter Taste Receptor Agonists | |
|---|---|
| Compound: | Chemical structure: |
| Menthol | 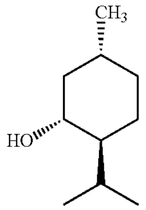 |
| Ofloxacin | 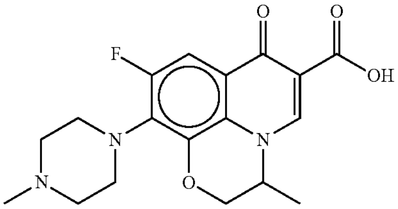 |
| Chloroquine | 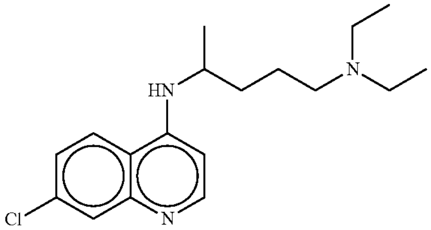 |
| Colchicine | 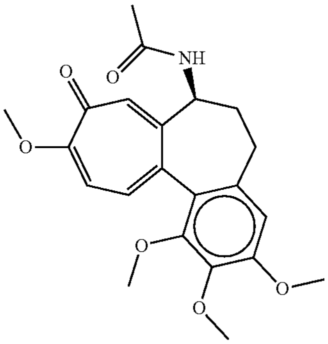 |
| 1,10-phenanthroline | 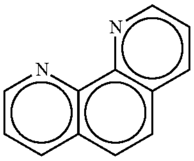 |
| Cucurbitacin B | 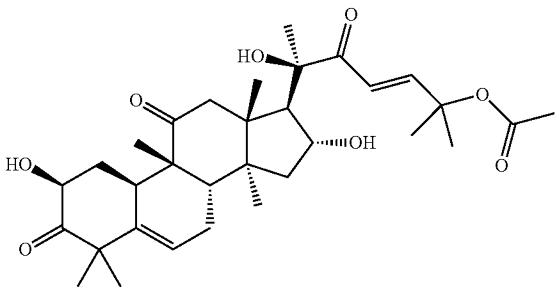 [SMILES: CC(=O)OC(C)(C)/C=C/C(=O)[C@](C)(O)[C@H]1[C@H](O)C[C@@]2(C)[C@@H]3CC=C4[C@@H](C[C@H](O)C(=O)C4(C)C)[C@]3(C)C(=O)C[C@]12C] |

TABLE 1-continued

| Canine Bitter Taste Receptor Agonists | |
|---|---|
| Compound: | Chemical structure: |
| Propylthiouracil | 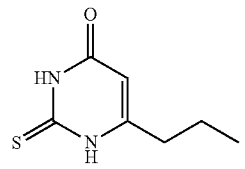 |

In certain embodiments, the bitter taste receptor modulators of the present disclosure comprise a salt of the bitter taste receptor modulator, for example, but not limited to, an acetate salt or a formate salt. In certain embodiments, the bitter taste receptor modulator salt comprises an anion (−) (for example, but not limited to, $Cl^-$, $O^{2-}$, $CO_3^{2-}$, $HCO_3^-$, $OH^-$, $NO_3^-$, $PO_4^{3-}$, $SO_4^{2-}$, $CH_3COO^-$, $HCOO^-$ and $C_2O_4^{2-}$) bonded via an ionic bond with a cation (+) (for example, but not limited to, $Al^{3+}$, $Ca^{2+}$, $Na^+$, $K^+$, $Cu^{2+}$, $H^+$, $Fe^{3+}$, $Mg^{2+}$, $NH_4^+$ and $H_3O^+$). In other embodiments, the bitter taste receptor agonist salt comprises a cation (+) bonded via an ionic bond with an anion (−).

In certain embodiments, the bitter taste receptor modulators of the present application are identified through in silico modeling of a bitter taste receptor, e.g., a canine bitter taste receptor, wherein the bitter taste receptor modulators of the present application comprise a structure that fits within a binding site of the bitter taste receptor. In certain embodiments, the in silico method comprises the in silico methods described above and in the Examples section of the present application.

In certain embodiments, the bitter taste receptor modulators of the present application are identified through an in vitro method, wherein the bitter taste receptor modulator compounds modulate a bitter taste receptor, disclosed herein, expressed by cells in vitro. In certain embodiments, the in vitro method comprises the in vitro methods described above and in the Examples section of the present application.

4. Pet Food Products

The present application provides for screening methods that can be used to identify suitable raw materials to produce a palatable and nutritious pet food product. The presently disclosed screening methods can also be used to determine if a finished pet food product would be palatable to the pet (e.g., a dog). For example, the in vitro methods described herein can be used to screen raw materials and finished pet food products to identify whether the raw materials or finished pet food products comprise compounds that modulate bitter receptor activity and/or expression. In certain embodiments, raw materials and finished pet food products that do not increase the activity and/or expression of a bitter receptor can be selected for use in, or as, a pet food product for consumption. Non-limiting examples of suitable pet food products include wet food products, dry food products, moist food products, pet food supplements (e.g., vitamins), pet beverage products, snack and treats and pet food categories described herein.

One of the goals of the pet care industry is to identify sustainable protein sources for pets that do not compete with the human food chain. As such, there is an ongoing search for novel protein sources that fit these criteria. The presently disclosed screening method can be used to identify which of the novel protein sources would be considered palatable to the pet, or at least have no effect on the palatability of the other ingredients of the pet food. In certain embodiments, the novel protein source (i.e., raw material) is meat, fish, cheese, beans, yeast, yeast extracts, bacteria, algae, fungi, nuts, seeds or other plant material, or combinations thereof. In certain embodiments, the raw material is meat.

In certain embodiments, the protein source can be derived from a variety of plant sources. Non-limiting examples of plant sources include corn, maize, rice, soy, wheat, etc. For example, and not by way of limitation, the plant-derived protein can include lupin protein, wheat protein, soy protein and combinations thereof. Alternatively or additionally, the protein source can be derived from a variety of animal sources, for example, a multicellular eukaryotic organism from the kingdom animalia. Non-limiting examples of animal protein include beef, pork, poultry, lamb or fish including, for example, muscle meat, meat byproduct, meat meal or fish meal. Other non-limiting examples of animal sources include insects, or other organism from the phylum arthropoda.

In certain embodiments, the protein source can be derived from yeast or any other single-cell eukaryotic organisms, mold, mushroom or fungi.

In certain embodiments, the protein source can be derived from bacteria, archaea, or any other archaebacteria, eubacteria, or prokaryotic organism.

In certain embodiments, the protein source can be derived from algae, kelp, seaweed, or any other single or multicellular photosynthetic organism or protist.

In certain embodiments, the presently disclosed subject matter includes accepting or rejecting a raw material for the production of pet food based on the raw material's ability to enhance, increase, decrease and/or modulate the activity and/or expression of a bitter taste receptor. In certain embodiments, the raw material is rejected if the raw material results in the enhancement or increase in the activity and/or expression of at least one bitter taste receptor. In certain embodiments, the raw material is rejected if the raw material results in the enhancement or increase in the activity and/or expression of at least two, at least three, at least four, at least five, at least six, at least seven, at least eight, at least nine, at least ten, at least eleven, at least twelve, at least thirteen, at least fourteen, at least fifteen, and/or at least sixteen bitter taste receptors. In certain embodiments, the raw material is accepted if it does not modulate the activity of at least one bitter taste receptor. In certain embodiments, the raw material is selected if it inhibits or blocks the activity and/or expression of at least one bitter taste receptor. In certain embodiments, the bitter receptor is selected from any one or more of canine T2R1, T2R2, T2R3, T2R4, T2R5, T2R7, T2R10, T2R12, T2R38, T2R39, T2R40, T2R41, T2R42, T2R43, T2R62, and/or T2R67.

In certain non-limiting embodiments, a raw material that results in the enhancement or increase in the activity and/or expression of at least one bitter taste receptor can be admixed with a compound that inhibits or reduces the activity and/or expression of the at least one bitter receptor, wherein the admixture is accepted for the production of pet food.

During the production of pet food, some of the materials may change form due to mechanical forces, thermal forces, or chemical reactions. The presently disclosed screening method can be used to identify pet food products that form compounds that are unpalatable to an animal, for example, a canine, for example, a compound that enhances or increases the activity and/or expression of a bitter receptor.

In certain embodiments, the presently disclosed subject matter includes accepting or rejecting a pet food product based on the product's ability to enhance, increase, decrease and/or modulate the activity and/or expression of a bitter taste receptor. In certain embodiments, the pet food product is rejected if the product results in the enhancement or increase in the activity and/or expression of at least one bitter taste receptor. In certain embodiments, the pet food product is rejected if the product results in the enhancement or increase in the activity and/or expression of at least two, at least three, at least four, at least five, at least six, at least seven, at least eight, at least nine, at least ten, at least eleven, at least twelve, at least thirteen, at least fourteen, at least fifteen, and/or at least sixteen bitter taste receptors. In certain embodiments, the pet food product is accepted if it does not modulate the activity of at least one bitter taste receptor. In certain embodiments, the pet food product is selected if it inhibits or blocks the activity and/or expression of at least one bitter taste receptor. In certain embodiments, the bitter receptor is selected from any one or more of canine T2R1, T2R2, T2R3, T2R4, T2R5, T2R7, T2R10, T2R12, T2R38, T2R39, T2R40, T2R41, T2R42, T2R43, T2R62, and/or T2R67.

The flavor compositions of the present disclosed subject matter can also be used in a wide variety of pet food products. The combination of the flavoring composition(s) of the presently disclosed subject matter together with a pet food product and optional ingredients, when desired, provides a flavoring agent that possesses unexpected taste and imparts, for example, a desirable bitter sensory experience. The flavor compositions disclosed herein can be added prior to, during or after formulation processing or packaging of the pet food product, and the components of the flavor composition can be added sequentially or simultaneously.

In certain embodiments, the pet food product is a nutritionally complete dry, wet or semi-moist food product. A dry or low moisture-containing nutritionally-complete pet food product can comprise less than about 15% moisture. A wet or high moisture-containing nutritionally-complete pet food product can comprise greater than about 50% moisture. Such food products can include from about 10% to about 90% fat, from about 10% to about 70% protein and from about 5% to about 80% carbohydrates, e.g., dietary fiber and ash, on a percent energy basis.

In certain embodiments, the pet food product is a nutritionally complete dry, wet or semi-moist food product. In certain embodiments, the pet food product includes from about 60% fat, from about 30% protein and from about 10% carbohydrates, e.g., dietary fiber and ash, on a percent energy basis.

In certain embodiments, the pet food product is a nutritionally complete moist food product. A moist, e.g., semi-moist or semi-dry or soft dry or soft moist or intermediate or medium moisture containing nutritionally-complete pet food product comprises from about 15 to about 50% moisture.

In certain embodiments, the pet food product is a pet food snack product. Non-limiting examples of pet food snack products include snack bars, pet chews, crunchy treats, cereal bars, snacks, biscuits and sweet products.

In certain embodiments of the present disclosure, the taste and/or palatability attributes of a pet food product or medicine prepared according to the methods described herein can be measured by an in vivo tasting method that uses a panelist of taste testers. For example, but not by way of limitation, the panel can contain canine panelists. In certain embodiments, the palatability of a pet food product containing, for example, a screened raw material or a screened pet food product can be determined by the consumption of the pet food product alone (e.g., the one bowl test, monadic ranking). In certain embodiments, the palatability of a screened raw material or a screened pet food product can be determined by the preferential consumption of the pet food product or raw material, versus a pet food product that is known to be palatable to the animal (e.g., the two bowl test for testing preference, difference and/or choice).

In certain embodiments, the palatability and/or bitter blocking taste of a compound identified according to the methods described herein can be determined by the preferential consumption of a water solution containing said compound versus a water solution that does not contain the compound or contains a different flavor composition, for example, a bitter receptor agonist (e.g., the two bottle test). The intake ratio for each pet food product or water solution can be determined by measuring the amount of one ration consumed divided by the total consumption. The consumption ratio (CR) can then be calculated to compare the consumption of one ration in terms of the other ration to determine the preferential consumption of one food product or water solution over the other. Alternatively or additionally, the difference in intake (g) can be used to assess the average difference in intake between the two solutions in a two bottle test or between two pet food products in a two bowl test at a selected significance level, for example, at the 5% significance level to determine an average difference in intake with a 95% confidence interval. In certain embodiments, the confidence interval can be about 90%. However, any significance level may be used, for example, a 1, 2, 3, 4, 5, 10, 15, 20, 25 or 50% significance level.

In certain embodiments, percentage preference scores, e.g., the percentage preference for one solution or food product by an animal, is the percentage of the total liquid or food product ingested during the test that that solution or food product accounts for, can also be calculated.

5. Taste Deterrents

The present disclosure provides methods for maintaining the health of an animal by imparting a bitter taste and/or decreasing the palatability of an object or surface. In certain embodiments, the method comprises applying, coating or contacting a taste deterrent product comprising a compound identified according to the methods described herein to the object or surface, and thereby preventing ingestion of said object or surface by an animal. Accordingly, detrimental effects on the animal's health that could result from ingestion of said object or surface are avoided. In certain embodiments, the object or surface is harmful to the health of the animal or toxic to the animal.

EXAMPLES

The presently disclosed subject matter will be better understood by reference to the following Examples, which are provided as exemplary of the invention, and not by way of limitation.

Example 1—In Silico Model of Interactions Between Canine T2R Receptors and Putative Binding Compounds The present example describes the computational modeling of canine bitter taste receptors (T2Rs) to identify putative bitter taste receptor modulators.

Homology models of canine T2R receptors were based on crystal structure of 3 SN6 from Protein Data Bank (PDB). 3 SN6 is the crystal structure of β2 adrenergic receptor from Group A GPCR with bound agonist (BI-167107 from Boehringer Ingelheim). (Rasmussen et al., Nature, 477: 549-555 (2011)). The models were built using the I-TASSER Suite of programs (Yang et al., Nat Methods, 12: 7-8 (2015)) and Modeller (Eswar et al., Curr Protoc Bioinformatics, 15: 5.6.1-5.6.30 (2006)), which is part of the Discovery Studio (DS) suite of programs from Accelrys (Discovery Studio (DS) is suite of interactive modeling and simulation programs from the Accelrys corporation).

The bitter compounds were docked into the active site of canine bitter receptors. The docking program BioDock from BioPredict, Inc., was used but other state of the art docking programs could be used for this purpose.

The results of in silico modeling are presented in FIGS. 3-9.

Example 2—Identification of Canine Bitter Receptor (T2R) Modulators Using In Vitro Assays The present example describes an in vitro assay for identifying compounds that modulate the activation of the canine bitter taste receptor (T2R).

Compounds identified by in silico modeling with a bitter taste receptor, as detailed above in Example 1, as putative bitter taste receptor modulators will be selected for further testing in vitro. In vitro functional characterization of the selected modulators will be used to evaluate the effectiveness of a putative modulator compound in activating or inhibiting the bitter taste receptor.

HEK293 cells (or other suitable expression system) that stably or transiently express a canine bitter taste receptor (e.g., canine T2R1, T2R2, T2R3, T2R4, T2R5, T2R7, T2R10, T2R12, T2R38, T2R39, T2R40, T2R41, T2R42, T2R43, T2R62, or T2R67) will be exposed to putative compounds to modulate the activity and/or expression of the bitter taste receptor.

An exemplary method of an in vitro assay is as follows. All transient transfections will be performed with, for example, Lipofectamine2000 (Invitrogen) according to the manufactures protocol. 10 μl Lipofectamine2000 will be diluted in 500 μl DMEM (Life Technologies) and incubated for 5 minutes at room temperature. 3 μg of plasmid DNA (1 μg/μl) will be diluted in 500 μl DMEM and added to the Lipofectamine2000 mix to obtain a final volume of 1000 μl. After additional 30 minutes of incubation at room temperature, the DNA-Lipofectamine complex will be added to 1000 μl of a cell suspension containing 1,400,000 cells/ml. Subsequently, 25 μl of the complete mixture will be seeded into each well of a black 384 well polystyrene assay plate. At 3 hours post-transfection the transfection mix will be removed from the cells and fresh DMEM containing 10% FBS and 1% P/S will be added. At 27 to 30 hours post-transfection the medium will be removed from the cells and 20 μl loading buffer that includes a calcium sensitive fluorescent or luminescent dye (Tyrode's buffer+2 μM Fluo4-AM (Invitrogen)+2.5 mM probenecid (Invitrogen) for fluorescence or Coelenterazine (Biosynth)+Tyrode's buffer for luminescence) will be added for 1 hour (fluorescence) or 3 hours (luminescence) at 37° C. The cells will then be washed 2 times every 20 minutes with Tyrode's buffer using an automated plate washer (Biochrom Asys Plate Washer) for the fluorescent protocol. No wash step will be required for the luminescent protocol.

Activation of the bitter taste receptor will then be detected, for example, by detecting a change in intracellular calcium levels using the calcium sensitive fluorescent dye, the calcium sensitive luminescent photoprotein, or by any detection system known in the art. Cells that do not express the bitter taste receptor (MOCK control) will be used as a control. Examples of such data capturing systems include FLIPR® Tetra or a FlexStation® 3 system. However, other imaging techniques and systems can be used, for example, microscopic imaging of the treated cells.

For each putative bitter taste receptor modulator, dose response curves will be generated with at least 8 concentrations in triplicate and the $EC_{50}$ value of the putative bitter taste receptor modulator will be determined. Graphs will be plotted, for example, in SigmaPlot V12 (Systat Software) with error bars representing standard error. The term half maximal effective concentration ($EC_{50}$) refers to the concentration of a compound which induces a response halfway between the baseline and the maximum after a specified exposure time.

Example 3—Identification of Canine Bitter Receptor (T2R) Modulators Using In Vitro Assays The present example describes an in vitro assay for identifying compounds that modulate the activation of the canine bitter taste receptor (T2R) by a T2R ligand.

Compounds identified by in silico modeling with a bitter taste receptor, as detailed above in Example 1, as putative bitter taste receptor modulators will be selected for further testing in vitro. In vitro functional characterization of the selected modulators will be used to evaluate the effectiveness of a putative modulator compound in modulating the activation of the bitter taste receptor by a bitter taste receptor ligand.

HEK293 cells (or other suitable expression system) that stably or transiently express a canine bitter taste receptor (e.g., canine T2R1, T2R2, T2R3, T2R4, T2R5, T2R7, T2R10, T2R12, T2R38, T2R39, T2R40, T2R41, T2R42, T2R43, T2R62, or T2R67) will be exposed to putative modulator compounds and a bitter taste receptor ligand (e.g., an agonist) to modulate the activity and/or expression of the bitter taste receptor.

An exemplary method of an in vitro assay is as follows. All transient transfections will be performed with, for example, Lipofectamine2000 (Invitrogen) according to the manufactures protocol. 10 μl Lipofectamine2000 will be diluted in 500 μl DMEM (Life Technologies) and incubated for 5 minutes at room temperature. 3 μg of plasmid DNA (1 μg/μl) will be diluted in 500 μl DMEM and added to the Lipofectamine2000 mix to obtain a final volume of 1000 μl.

After additional 30 minutes of incubation at room temperature, the DNA-Lipofectamine complex will be added to 1000 μl of a cell suspension containing 1,400,000 cells/ml. Subsequently, 25 μl of the complete mixture will be seeded into each well of a black 384 well polystyrene assay plate. At 3 hours post-transfection the transfection mix will be removed from the cells and fresh DMEM containing 10% FBS and 1% P/S will be added. At 27 to 30 hours post-transfection the medium will be removed from the cells and 20 μl loading buffer that includes a calcium sensitive fluorescent dye or luminescent substrate (Tyrode's buffer+2 μM Fluo4-AM (Invitrogen)+2.5 mM probenecid (Invitrogen) for fluorescence or Coelenterazine (Biosynth)+Tyrode's buffer for luminescence) will be added for 1 hour (fluorescence) or 3 hours (luminescence) at 37° C. The cells will then be washed 2 times every 20 minutes with Tyrode's buffer using an automated plate washer (Biochrom Asys Plate Washer) for the fluorescent protocol. No wash step will be required for the luminescent protocol.

Activation of the bitter taste receptor will then be detected, for example, by detecting a change in intracellular calcium levels using the calcium sensitive fluorescent dye, the calcium sensitive luminescent photoprotein, or by any detection system known in the art. Cells that do not express the bitter taste receptor (MOCK control) will be used as a control. Examples of such data capturing systems include FLIPR® Tetra or a FlexStation® 3 system. However, other imaging techniques and systems can be used, for example, microscopic imaging of the treated cells.

For each putative bitter taste receptor modulator, dose response curves will be generated with at least 8 concentrations in triplicate and the $EC_{50}$ value of the putative bitter taste receptor modulator will be determined. Graphs will be plotted, for example, in SigmaPlot V12 (Systat Software) with error bars representing standard error.

Example 4—BLAST Search Homology Comparison of Canine T2R Receptors and Human T2R Receptors A BLAST search was conducted to compare certain canine T2R amino acid sequences with human T2R amino acid sequences. BlastP was used with parameters set as follows: Matrix Blosum 62; gap existence cost 11; gap extension cost 1; and use of compositional score matrix adjustment.

T2R2 is shared by dog and cat, but not human. A BLAST search comparison of the canine T2R2 amino acid sequence with human T2R amino acid sequences shows that the canine T2R2 was equidistant from every human T2R bitter receptor tested (Table 2).

TABLE 2

BLAST Search Homology Comparison of Canine T2R2 to Human T2R

| Description | Max score | Total score | Query Cover | E value | Sequence Identity |
|---|---|---|---|---|---|
| taste receptor type 2 member 7 [*Homo sapiens*] | 172 | 172 | 93% | 3e−50 | 35% |
| taste receptor type 2 member 9 [*Homo sapiens*] | 158 | 158 | 97% | 9e−45 | 33% |
| taste receptor type 2 member 10 [*Homo sapiens*] | 143 | 143 | 97% | 4e−39 | 32% |
| taste receptor type 2 member 8 [*Homo sapiens*] | 141 | 141 | 97% | 1e−38 | 33% |

TABLE 2-continued

BLAST Search Homology Comparison of Canine T2R2 to Human T2R

| Description | Max score | Total score | Query Cover | E value | Sequence Identity |
|---|---|---|---|---|---|
| taste receptor type 2 member 41 [*Homo sapiens*] | 134 | 134 | 93% | 9e−36 | 31% |
| taste receptor type 2 member 13 [*Homo sapiens*] | 133 | 133 | 97% | 1e−35 | 29% |
| taste receptor type 2 member 1 [*Homo sapiens*] | 129 | 129 | 95% | 5e−34 | 32% |
| taste receptor type 2 member 42 [*Homo sapiens*] | 129 | 129 | 97% | 6e−34 | 34% |
| taste receptor type 2 member 39 [*Homo sapiens*] | 120 | 120 | 96% | 1e−30 | 29% |
| taste receptor type 2 member 5 [*Homo sapiens*] | 117 | 117 | 97% | 1e−29 | 31% |
| taste receptor type 2 member 60 [*Homo sapiens*] | 115 | 115 | 91% | 6e−29 | 30% |
| taste receptor type 2 member 43 [*Homo sapiens*] | 115 | 115 | 93% | 7e−29 | 32% |
| taste receptor type 2 member 30 [*Homo sapiens*] | 115 | 115 | 96% | 9e−29 | 32% |
| taste receptor type 2 member 45 [*Homo sapiens*] | 113 | 113 | 96% | 3e−28 | 31% |
| taste receptor type 2 member 40 [*Homo sapiens*] | 112 | 112 | 96% | 1e−27 | 30% |
| taste receptor type 2 member 3 [*Homo sapiens*] | 111 | 111 | 95% | 2e−27 | 32% |
| taste receptor type 2 member 16 [*Homo sapiens*] | 109 | 109 | 95% | 6e−27 | 28% |
| taste receptor type 2 member 31 [*Homo sapiens*] | 107 | 107 | 92% | 3e−26 | 33% |
| taste receptor type 2 member 46 [*Homo sapiens*] | 104 | 104 | 96% | 4e−25 | 30% |
| taste receptor type 2 member 19 [*Homo sapiens*] | 102 | 102 | 94% | 2e−24 | 28% |
| taste receptor type 2 member 38 [*Homo sapiens*] | 102 | 102 | 95% | 2e−24 | 28% |
| taste receptor type 2 member 50 [*Homo sapiens*] | 100 | 100 | 76% | 8e−24 | 31% |
| taste receptor type 2 member 20 [*Homo sapiens*] | 100 | 100 | 96% | 1e−23 | 29% |
| taste receptor type 2 member 4 [*Homo sapiens*] | 99.8 | 99.8 | 94% | 2e−23 | 29% |
| taste receptor type 2 member 14 [*Homo sapiens*] | 99.4 | 99.4 | 94% | 2e−23 | 28% |

T2R12 is shared by dog and cat, but not human. A BLAST search comparison of the canine T2R12 amino acid sequence with human T2R amino acid sequences shows that the canine T2R12 was equidistant from every human T2R bitter receptor tested (Table 3).

TABLE 3

BLAST Search Homology Comparison of Canine T2R12 to Human T2R

| Description | Max score | Total score | Query Cover | E value | Sequence Identity |
|---|---|---|---|---|---|
| taste receptor type 2 member 7 [*Homo sapiens*] | 196 | 196 | 98% | 3e−59 | 40% |
| taste receptor type 2 member 8 [*Homo sapiens*] | 188 | 188 | 96% | 2e−56 | 41% |
| taste receptor type 2 member 9 [*Homo sapiens*] | 168 | 168 | 100% | 1e−48 | 39% |
| taste receptor type 2 member 10 [*Homo sapiens*] | 160 | 160 | 99% | 1e−45 | 38% |
| taste receptor type 2 member 30 [*Homo sapiens*] | 157 | 157 | 95% | 2e−44 | 39% |
| taste receptor type 2 member 46 [*Homo sapiens*] | 150 | 150 | 97% | 5e−42 | 36% |
| taste receptor type 2 member 13 [*Homo sapiens*] | 150 | 150 | 99% | 6e−42 | 35% |

TABLE 3-continued

BLAST Search Homology Comparison of Canine T2R12 to Human T2R

| Description | Max score | Total score | Query Cover | E value | Sequence Identity |
|---|---|---|---|---|---|
| taste receptor type 2 member 14 [*Homo sapiens*] | 150 | 150 | 99% | 8e−42 | 38% |
| taste receptor type 2 member 43 [*Homo sapiens*] | 149 | 149 | 94% | 2e−41 | 38% |
| taste receptor type 2 member 45 [*Homo sapiens*] | 147 | 147 | 97% | 9e−41 | 34% |
| taste receptor type 2 member 3 [*Homo sapiens*] | 136 | 136 | 100% | 1e−36 | 37% |
| taste receptor type 2 member 31 [*Homo sapiens*] | 133 | 133 | 94% | 2e−35 | 36% |
| taste receptor type 2 member 20 [*Homo sapiens*] | 130 | 130 | 97% | 2e−34 | 35% |
| taste receptor type 2 member 19 [*Homo sapiens*] | 127 | 127 | 97% | 3e−33 | 36% |
| taste receptor type 2 member 42 [*Homo sapiens*] | 126 | 126 | 98% | 1e−32 | 35% |
| taste receptor type 2 member 50 [*Homo sapiens*] | 122 | 122 | 94% | 2e−31 | 35% |
| taste receptor type 2 member 4 [*Homo sapiens*] | 95.5 | 95.5 | 94% | 4e−22 | 30% |
| taste receptor type 2 member 1 [*Homo sapiens*] | 95.1 | 95.1 | 93% | 7e−22 | 31% |
| taste receptor type 2 member 41 [*Homo sapiens*] | 89.7 | 89.7 | 91% | 4e−20 | 32% |
| taste receptor type 2 member 5 [*Homo sapiens*] | 86.3 | 86.3 | 96% | 7e−19 | 27% |
| taste receptor type 2 member 39 [*Homo sapiens*] | 85.9 | 85.9 | 95% | 1e−18 | 29% |
| taste receptor type 2 member 38 [*Homo sapiens*] | 85.5 | 85.5 | 98% | 2e−18 | 30% |
| taste receptor type 2 member 40 [*Homo sapiens*] | 78.2 | 78.2 | 96% | 5e−16 | 30% |
| taste receptor type 2 member 60 [*Homo sapiens*] | 72.4 | 72.4 | 91% | 6e−14 | 26% |
| taste receptor type 2 member 16 [*Homo sapiens*] | 57.0 | 57.0 | 81% | 1e−08 | 27% |

Canine T2R62 is unique to dog when compared to humans and felines. In particular, canine T2R62 comprises an amino acid sequence that is different from all human bitter receptors (Table 4).

TABLE 4

BLAST Search Homology Comparison of Canine T2R62 to Human T2R

| Description | Max score | Total score | Query Cover | E value | Sequence Identity |
|---|---|---|---|---|---|
| taste receptor type 2 member 16 [*Homo sapiens*] | 203 | 203 | 98% | 1e−62 | 39% |
| taste receptor type 2 member 41 [*Homo sapiens*] | 184 | 184 | 90% | 7e−55 | 40% |
| taste receptor type 2 member 60 [*Homo sapiens*] | 157 | 157 | 93% | 1e−44 | 36% |
| taste receptor type 2 member 9 [*Homo sapiens*] | 115 | 115 | 99% | 3e−29 | 32% |
| taste receptor type 2 member 1 [*Homo sapiens*] | 115 | 115 | 97% | 3e−29 | 31% |
| taste receptor type 2 member 46 [*Homo sapiens*] | 115 | 115 | 98% | 5e−29 | 30% |
| taste receptor type 2 member 13 [*Homo sapiens*] | 115 | 115 | 96% | 5e−29 | 30% |
| taste receptor type 2 member 7 [*Homo sapiens*] | 115 | 115 | 98% | 5e−29 | 30% |

Example 5—Identification of Canine Bitter Receptor (T2R) Modulators Using In Vitro Assays Compounds identified by in silico modeling with a bitter taste receptor, as detailed above in Example 1, were selected for further testing in vitro. In vitro functional characterization of the selected modulators was used to evaluate the effectiveness of the putative modulator compounds in modulating the activation of the bitter taste receptors.

HEK293 cells that transiently expressed a canine bitter taste receptor selected from canine T2R1, T2R2, T2R3, T2R4, T2R5, T2R10, and T2R43, were exposed to compounds to determine whether the compounds modulated the activity of the bitter taste receptors.

All transient transfections were performed with Lipofectamine2000 (Invitrogen) according to the manufactures protocol. 10 μl Lipofectamine2000 were diluted in 500 μl DMEM (Life Technologies) and incubated for 5 minutes at room temperature. 3 μg of plasmid DNA (1 μg/μl) was diluted in 500 μl DMEM and added to the Lipofectamine2000 mix to obtain a final volume of 1000 μl. After an additional 30 minutes of incubation at room temperature, the DNA-Lipofectamine complex was added to 1000 μl of a cell suspension containing 1,400,000 cells/ml. Subsequently, 25 μl of the complete mixture was seeded into each well of a black 384 well polystyrene assay plate. At 3 hours post-transfection the transfection mix was removed from the cells and fresh DMEM containing 10% FBS and 1% P/S was added. At 27 to 30 hours post-transfection the medium was removed from the cells and 20 μl loading buffer that included a calcium sensitive fluorescent dye or luminescent substrate (Tyrode's buffer+2 μM Fluo4-AM (Invitrogen)+2.5 mM probenecid (Invitrogen) for fluorescence or Coelenterazine (Biosynth)+Tyrode's buffer for luminescence) were added for 1 hour (fluorescence) or 3 hours (luminescence) at 37° C. The cells were then washed 2 times every 20 minutes with Tyrode's buffer using an automated plate washer (Biochrom Asys Plate Washer) for the fluorescent protocol. No wash step was required for the luminescent protocol.

Activation of the bitter taste receptor was determined by detecting a change in intracellular calcium levels as measured by fluorescence or luminescence of the calcium sensitive fluorescent dye or luminescent photoprotein. Cells that did not express the bitter taste receptor (MOCK control) were used as a control. A FLIPR® Tetra system was used to measure fluorescence or luminescence.

For each putative bitter taste receptor modulator, dose response curves were generated with at least 8 concentrations in triplicate and the EC50 value of the putative bitter taste receptor modulator was determined as shown in FIGS. 3-9. Graphs were plotted in SigmaPlot V12 (Systat Software) with error bars representing standard error.

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Patents, patent applications, publications, product descriptions and protocols are cited throughout this application the disclosures of which are incorporated herein by reference in their entireties for all purposes.

We claim:

1. A method for producing a pet food product, the method comprising:

(a) measuring a first intracellular calcium level of a cell expressing a bitter taste receptor;

(b) contacting a test compound with the cell;

(c) measuring a second intracellular calcium level of the cell;

(d) selecting the test compound as capable of reducing the bitter taste when the second intracellular calcium level is lesser than the first intracellular calcium level; and (e) admixing the test compound with a pet food product to thereby reduce bitter taste;

wherein the bitter taste receptor is a T2R2 comprising the amino acid sequence set forth in SEQ ID NO: 18.

2. The method of claim 1 further comprising detecting an in silico interaction between the test agent and one or more amino acids in a 7 transmembrane domain (7TM) domain of the bitter taste receptor; and identifying the test compound as capable of increasing the activity of the bitter taste receptor if the interaction is detected.

3. The method of claim 2, wherein the one or more amino acids of the bitter taste receptor detected in silico are selected from the group consisting of Ser94, Trp90, Lys268, Tyr245, Glu180, Arg176, Met91, Asn185, Val184, Met181, Phe249, Pro155, Gln177, Lys174, Phe264, Phe93, Leu59, Met271, Phe246, and Leu188.

4. The method for claim 1, wherein the cell expresses a second bitter taste receptor selected from the group consisting of T2R1 comprising the amino acid sequence set forth in SEQ ID NO: 17, T2R3 comprising the amino acid sequence set forth in SEQ ID NO: 19, T2R4 comprising the amino acid sequence set forth in SEQ ID NO: 20, T2R5 comprising the amino acid sequence set forth in SEQ ID NO: 21, T2R7 comprising the amino acid sequence set forth in SEQ ID NO: 22, T2R10 comprising the amino acid sequence set forth in SEQ ID NO: 23, T2R12 comprising the amino acid sequence set forth in SEQ ID NO: 24, T2R38 comprising the amino acid sequence set forth in SEQ ID NO: 25, T2R39 comprising the amino acid sequence set forth in SEQ ID NO: 26, T2R40 comprising the amino acid sequence set forth in SEQ ID NO: 27, T2R41 comprising the amino acid sequence set forth in SEQ ID NO: 28, T2R42 comprising the amino acid sequence set forth in SEQ ID NO: 29, T2R43 comprising the amino acid sequence set forth in SEQ ID NO: 30, T2R62 comprising the amino acid sequence set forth in SEQ ID NO: 31, and T2R67 comprising the amino acid sequence set forth in SEQ ID NO: 32.

5. The method of claim 4 further comprising:

detecting an in silico interaction between the test agent and one or more amino acids in a 7 transmembrane domain (7TM) domain of the second bitter taste receptor; and identifying the test compound as capable of increasing the activity of the second bitter taste receptor if the interaction is detected.

6. The method of claim 5, wherein the one or more amino acids of the bitter taste receptor detected in silico are selected from the group consisting of Asn89, Tyr239, Ile167, Gln174, Glu169, Phe257, Ala242, Phe177, His238, Cys260, Phe264, Leu234, Cys235, Phe85, Leu261, Leu178, Leu181, Val86, and Phe82.

7. The method of claim 5, wherein the one or more amino acids of the bitter taste receptor detected in silico are selected from the group consisting of Asn93, Asp86, Tyr246, Phe247, Thr186, Asn189, Trp89, Arg175, Phe250, Gly185, Phe243, Thr90, Asn176, Val149, Ile154, Lys174, Met82, Ile85, Lys173, and Met69.

8. The method of claim 5, wherein the one or more amino acids of the bitter taste receptor detected in silico are selected from the group consisting of Ser186, Asp93, Tyr240, Ser94, Leu97, Asn95, Leu92, Ser96, Trp98, Vail 87, Thr247, Tyr243, T 89, Met58, Ser269, Pro273, Ser270, Gln189, Thr144, Leu188, Val183, Leu182, Ser244, and Met90.

9. The method of claim 5, wherein the one or more amino acids of the bitter taste receptor detected in silico are selected from the group consisting of Ser89, Pro264, Leu58, Val88, Gln90, Ile86, Leu173, Trp165, Thr258, Ala261, Tyr234, Glu257, Met260, and Trp85.

10. The method of claim 5, wherein the one or more amino acids of the bitter taste receptor detected in silico are selected from the group consisting of Lys258, Leu180, Lys170, Glu172, Asn181, Phe261, Met265, Ile262, Gln169, Lys69, Met168, Ile245, Val90, Phe242, Gln94, Vail 84, Asn93, Trp89, and Tyr241.

11. The method of claim 5, wherein the one or more amino acids of the bitter taste receptor detected in silico are selected from the group consisting of Tyr241, Trp88, Thr181, Met177, Asn92, Asn184, Phe185, Gln152, His143, Phe261, Ala172, His85, Asp170, Lys265, Phe242, Leu245, Thr89, and Phe180.

* * * * *